(12) United States Patent
Besharim et al.

(10) Patent No.: US 7,089,928 B2
(45) Date of Patent: Aug. 15, 2006

(54) APPARATUS FOR SELF-GUIDED INTUBATION

(75) Inventors: Shlomo Besharim, Be'er Sheva (IL); Eliyahu Besharim, Be'er Sheva (IL)

(73) Assignee: Intumed Ltd., Be'er Sheva (IL)

( * ) Notice: Subject to any disclaimer, the term of this patent is extended or adjusted under 35 U.S.C. 154(b) by 636 days.

(21) Appl. No.: 10/107,597

(22) Filed: Mar. 27, 2002

(65) Prior Publication Data

US 2002/0173799 A1    Nov. 21, 2002

Related U.S. Application Data

(63) Continuation of application No. PCT/IL01/01121, filed on Dec. 5, 2001.

(30) Foreign Application Priority Data

Dec. 6, 2000    (IL) ..................................... 140136

(51) Int. Cl.
*A61M 16/00*    (2006.01)

(52) U.S. Cl. .................. 128/200.26; 606/108; 600/117

(58) Field of Classification Search .................... 606/1, 606/108, 130; 128/910, 200.24, 209.18, 128/207.14–207.18, 899; 604/910, 264; 600/454, 547, 585, 101, 117, 118, 429, 424
See application file for complete search history.

(56) References Cited

U.S. PATENT DOCUMENTS

| | | |
|---|---|---|
| 4,651,746 A | 3/1987 | Wall |
| 4,672,960 A | 6/1987 | Frankel |
| 4,691,701 A | 9/1987 | Williams |
| 4,728,499 A | 3/1988 | Fehder |
| 4,790,327 A | 12/1988 | Despotis |
| 4,827,925 A | 5/1989 | Vilasi .................... 128/207.14 |
| 4,910,590 A | 3/1990 | Gillies et al. |
| 5,018,509 A | 5/1991 | Suzuki et al. |
| 5,109,830 A | 5/1992 | Cho |
| 5,172,225 A | 12/1992 | Takahashi |
| 5,184,603 A | 2/1993 | Stone |
| 5,188,111 A | 2/1993 | Yates et al. |
| 5,203,320 A | 4/1993 | Augustine |
| 5,235,970 A | 8/1993 | Augustine |
| 5,257,636 A | 11/1993 | White |
| 5,282,472 A | 2/1994 | Companion et al. ... 128/662.06 |
| 5,307,804 A | 5/1994 | Bonnet |
| 5,331,967 A | 7/1994 | Akerson |

(Continued)

FOREIGN PATENT DOCUMENTS

EP    1 174 076    1/2002

OTHER PUBLICATIONS http://www.airwaycam.com/system.html.

*Primary Examiner*—Glen K. Dawson
(74) *Attorney, Agent, or Firm*—Ladas & Parry LLP

(57) ABSTRACT

An automatically operative medical insertion device and method including an insertable element which is adapted to be inserted within a living organism in vivo, a surface following element, physically associated with the insertable element and being arranged to follow a physical surface within the living organism in vivo, a driving subsystem operative to at least partially automatically direct the insertable element along the physical surface and a navigation subsystem operative to control the driving subsystem based at least partially on a perceived location of the surface following element along a reference pathway stored in the navigation subsystem.

108 Claims, 41 Drawing Sheets

U.S. PATENT DOCUMENTS

| | | | |
|---|---|---|---|
| 5,347,987 A | 9/1994 | Feldstein et al. | |
| 5,400,771 A | 3/1995 | Pirak et al. | |
| 5,445,161 A | 8/1995 | Huang | |
| 5,469,840 A * | 11/1995 | Tanii et al. | 600/117 |
| 5,506,912 A | 4/1996 | Nagasaki et al. | |
| 5,558,082 A | 9/1996 | Spencer | |
| 5,571,114 A | 11/1996 | Devanaboyina | 606/108 |
| 5,584,795 A | 12/1996 | Valenti | |
| 5,592,939 A | 1/1997 | Martinelli | |
| 5,681,260 A * | 10/1997 | Ueda et al. | 600/114 |
| 5,704,987 A | 1/1998 | Huynh et al. | |
| 5,720,275 A | 2/1998 | Patil et al. | |
| 5,885,248 A | 3/1999 | Denton | |
| 5,951,461 A | 9/1999 | Nyo et al. | |
| 5,951,571 A | 9/1999 | Audette | |
| 5,957,844 A | 9/1999 | Dekel et al. | |
| 5,971,997 A | 10/1999 | Guthrie et al. | |
| 5,976,072 A | 11/1999 | Greenberg | |
| 5,993,424 A | 11/1999 | Lorenzo et al. | |
| 6,015,414 A * | 1/2000 | Werp et al. | 606/108 |
| 6,053,166 A | 4/2000 | Gomez | |
| 6,079,409 A | 6/2000 | Brain | |
| 6,079,731 A | 6/2000 | Emig et al. | |
| 6,083,213 A | 7/2000 | Voda | |
| 6,090,040 A | 7/2000 | Metro | |
| 6,096,004 A | 8/2000 | Meglan et al. | 604/95 |
| 6,096,050 A | 8/2000 | Audette | |
| 6,129,683 A | 10/2000 | Sutton et al. | |
| 6,132,372 A | 10/2000 | Essen-Moller | |
| 6,135,948 A | 10/2000 | Lee | |
| 6,142,144 A | 11/2000 | Pacey | |
| 6,146,402 A | 11/2000 | Munoz | |
| 6,152,909 A | 11/2000 | Bagaoisan et al. | |
| 6,161,537 A | 12/2000 | Gravenstein et al. | |
| 6,164,277 A | 12/2000 | Merideth | |
| 6,167,145 A | 12/2000 | Foley et al. | |
| 6,173,199 B1 | 1/2001 | Gabriel | |
| 6,174,281 B1 | 1/2001 | Abramowitz | |
| 6,189,533 B1 | 2/2001 | Simon et al. | |
| 6,190,382 B1 | 2/2001 | Ormsby et al. | |
| 6,190,395 B1 | 2/2001 | Williams | |
| 6,196,225 B1 | 3/2001 | Allgeyer | |
| 6,202,646 B1 | 3/2001 | Camodeca et al. | |
| 6,203,497 B1 | 3/2001 | Dekel et al. | |
| 6,211,904 B1 | 4/2001 | Adair et al. | |
| 6,226,548 B1 | 5/2001 | Foley et al. | |
| 6,235,038 B1 | 5/2001 | Hunter et al. | |
| 6,236,875 B1 | 5/2001 | Bucholz et al. | |
| 6,248,112 B1 | 6/2001 | Gambale et al. | |
| 6,332,865 B1 | 12/2001 | Borody et al. | 600/114 |
| 6,398,755 B1 * | 6/2002 | Belef et al. | 604/95.01 |
| 6,475,223 B1 * | 11/2002 | Werp et al. | 606/108 |
| 6,485,482 B1 * | 11/2002 | Belef | 604/528 |

\* cited by examiner

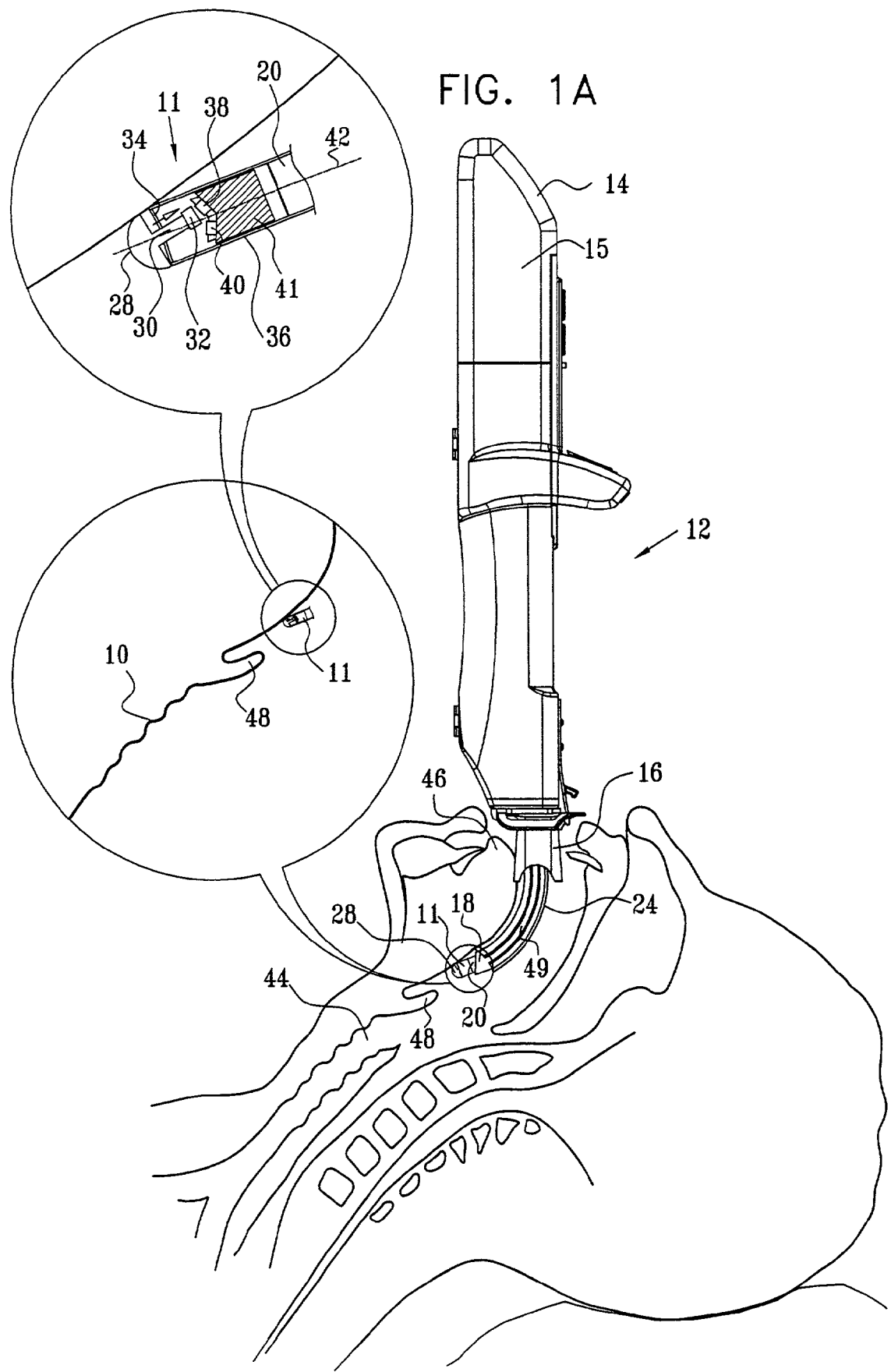

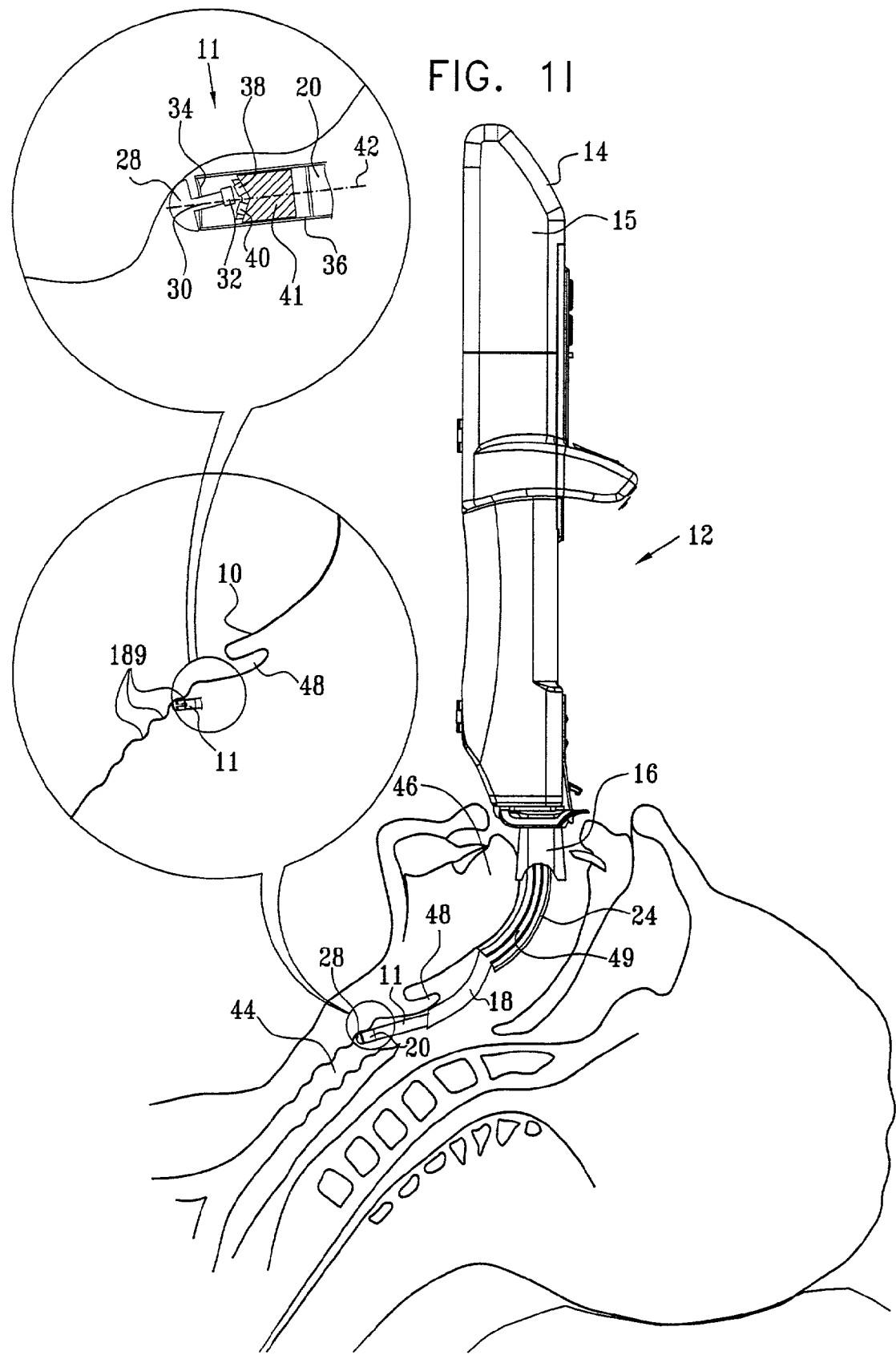

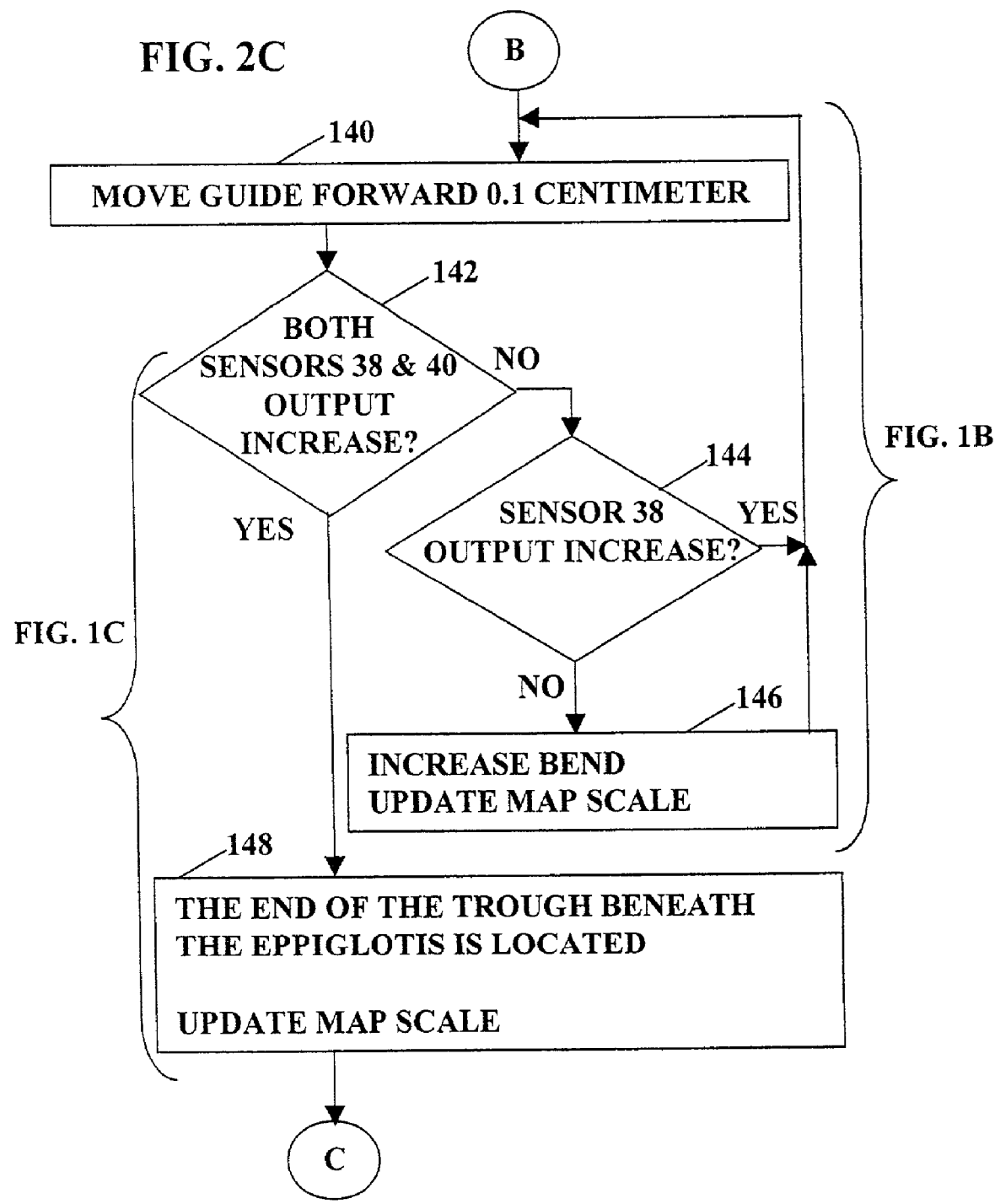

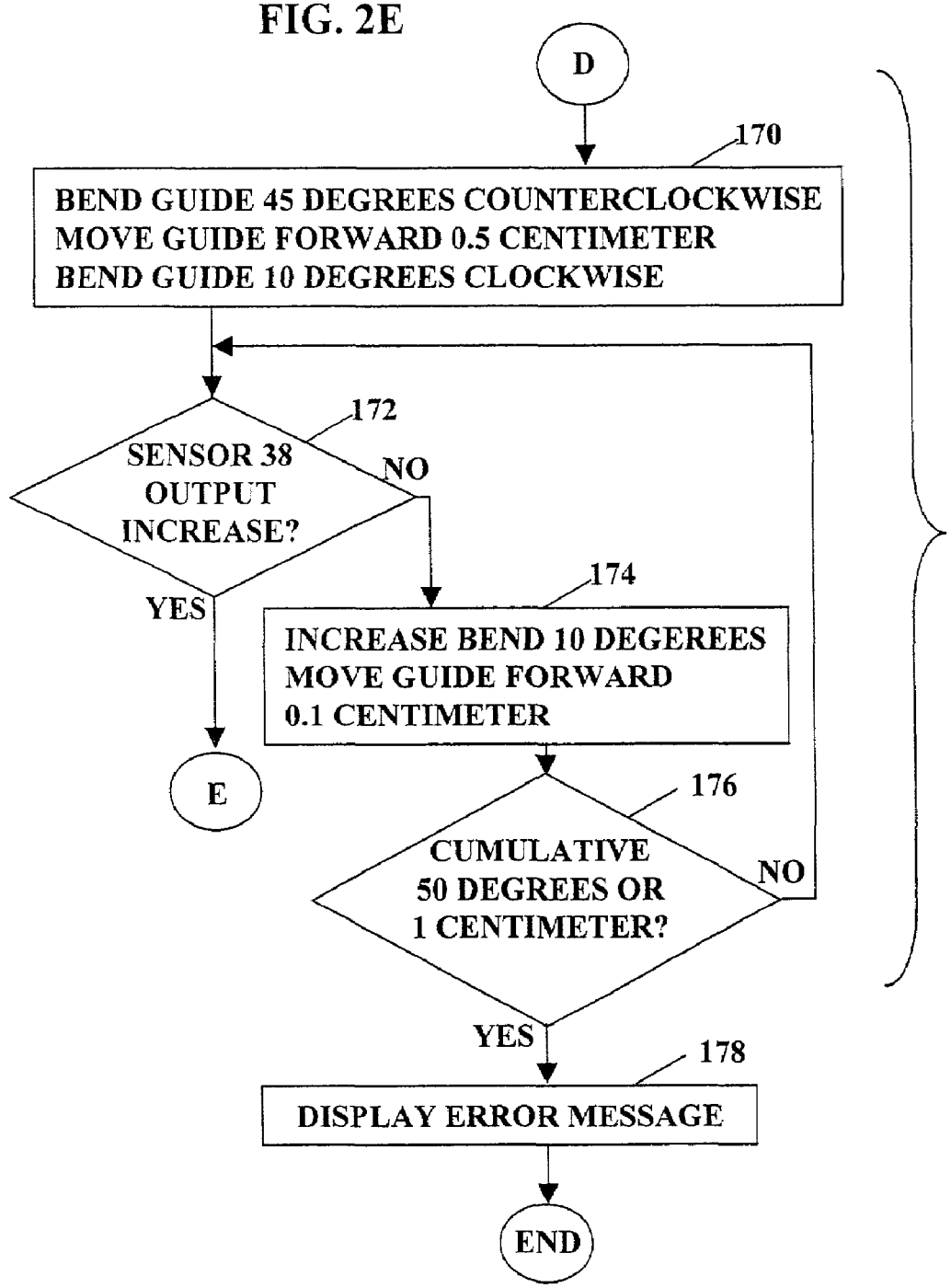

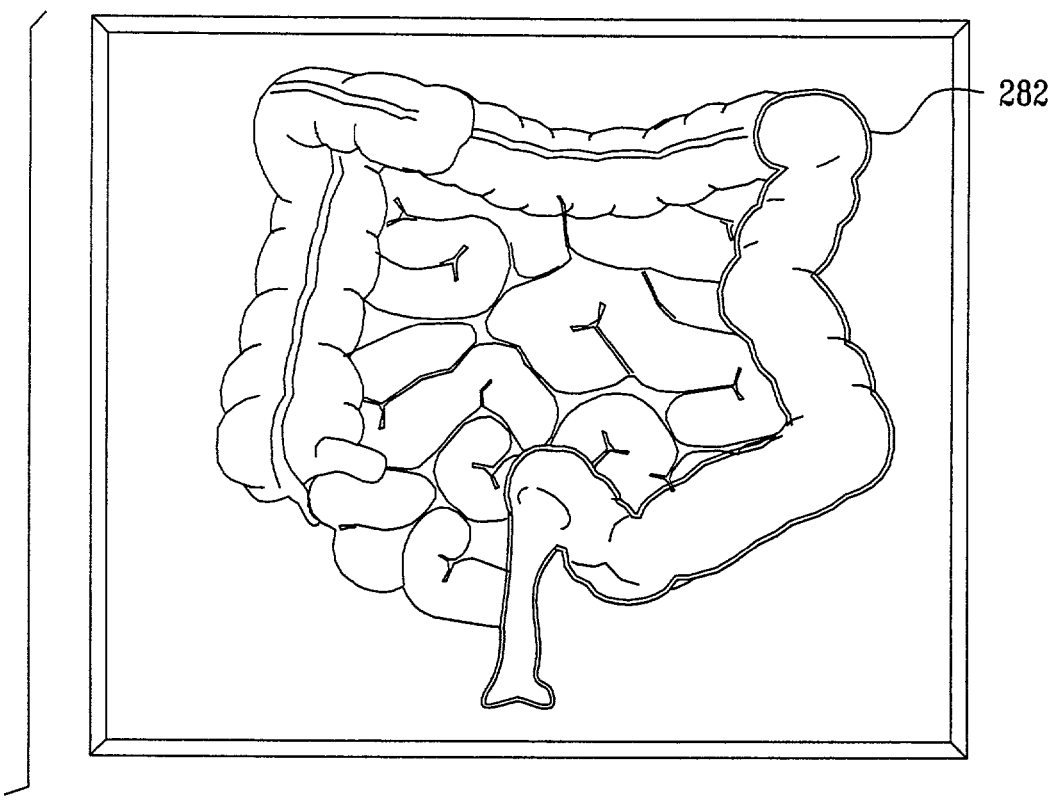
FIG. 6B
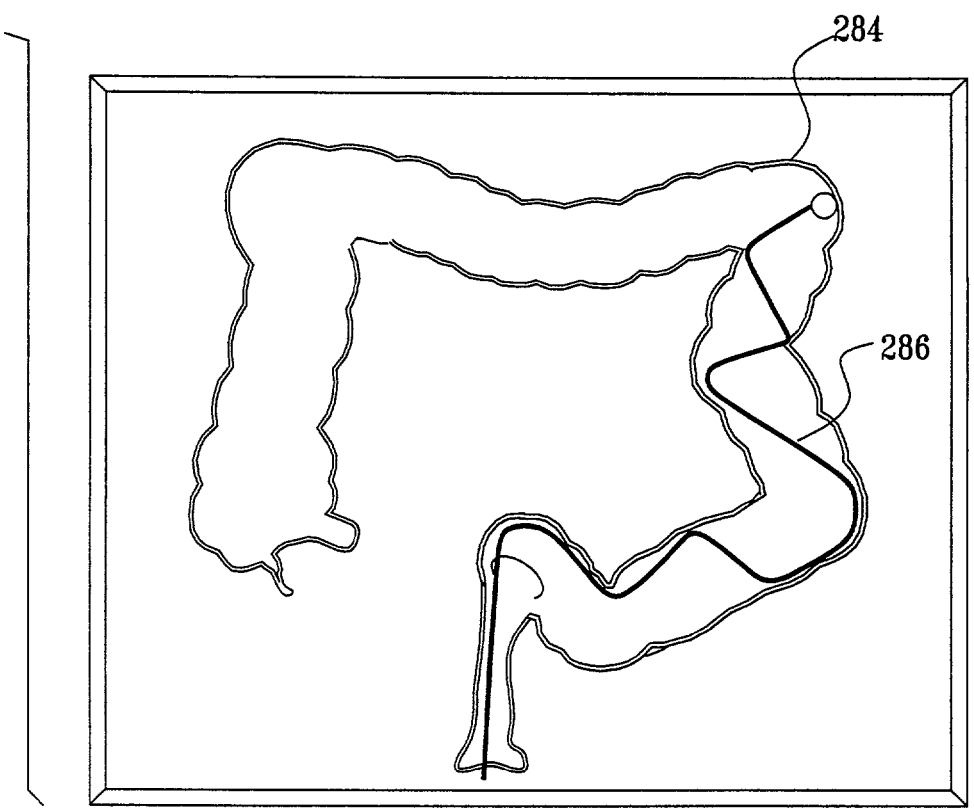

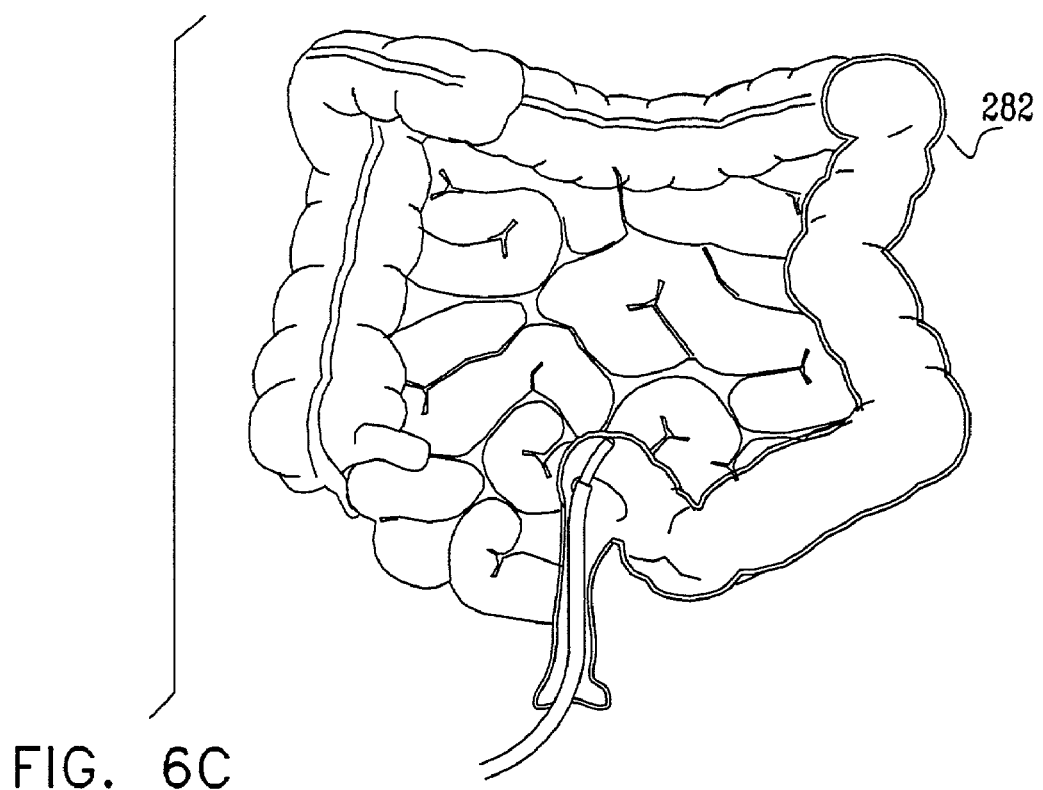
FIG. 6C
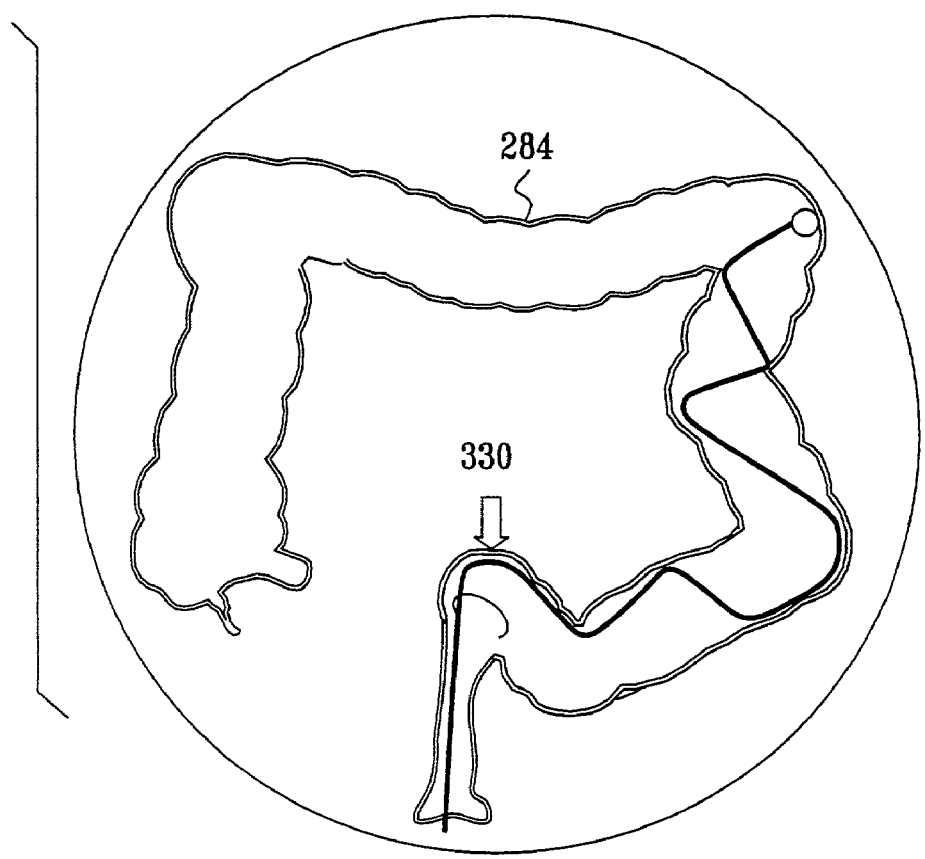

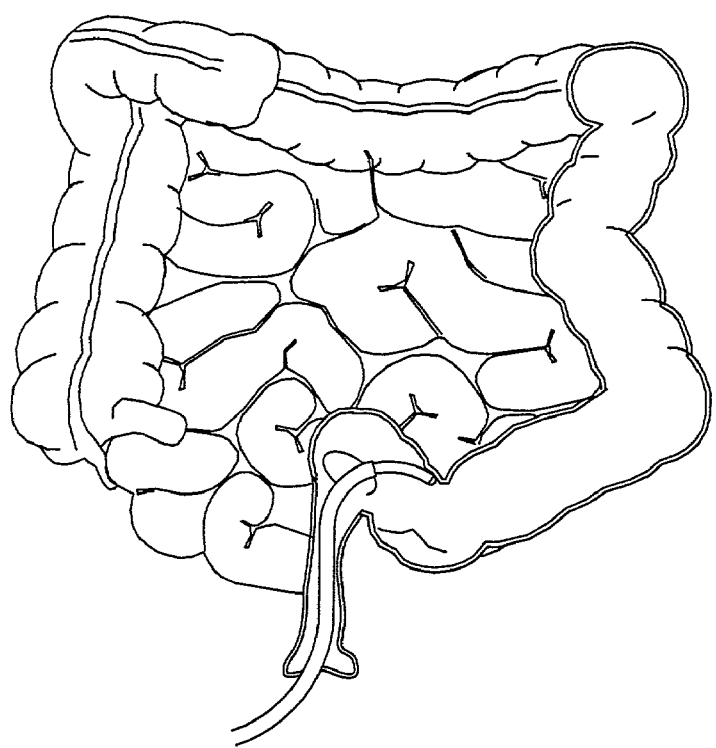
FIG. 6D
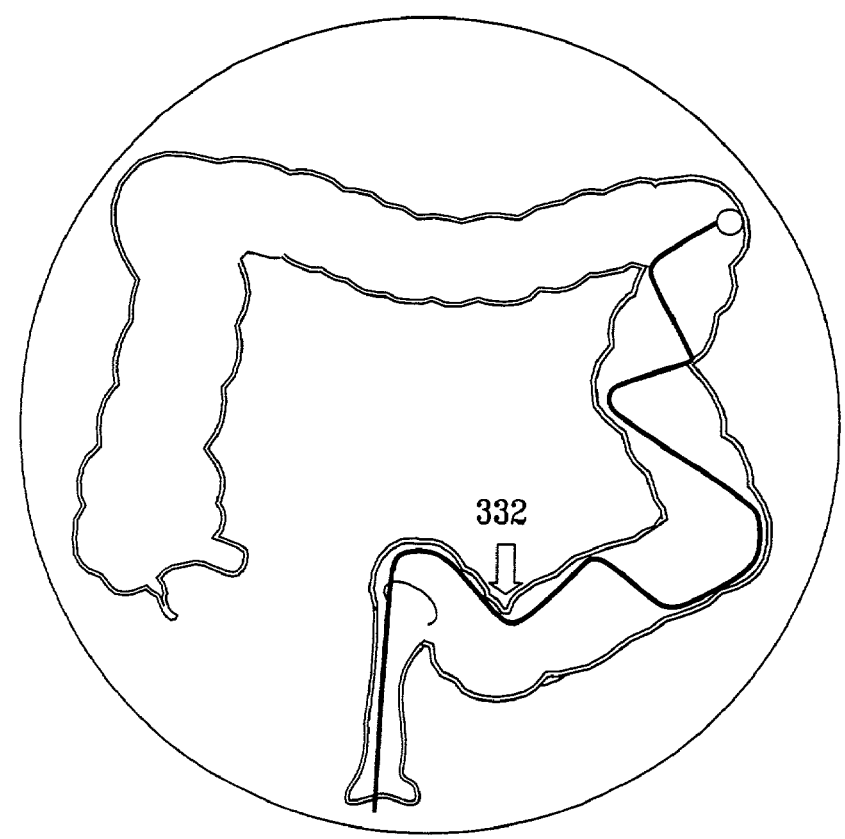

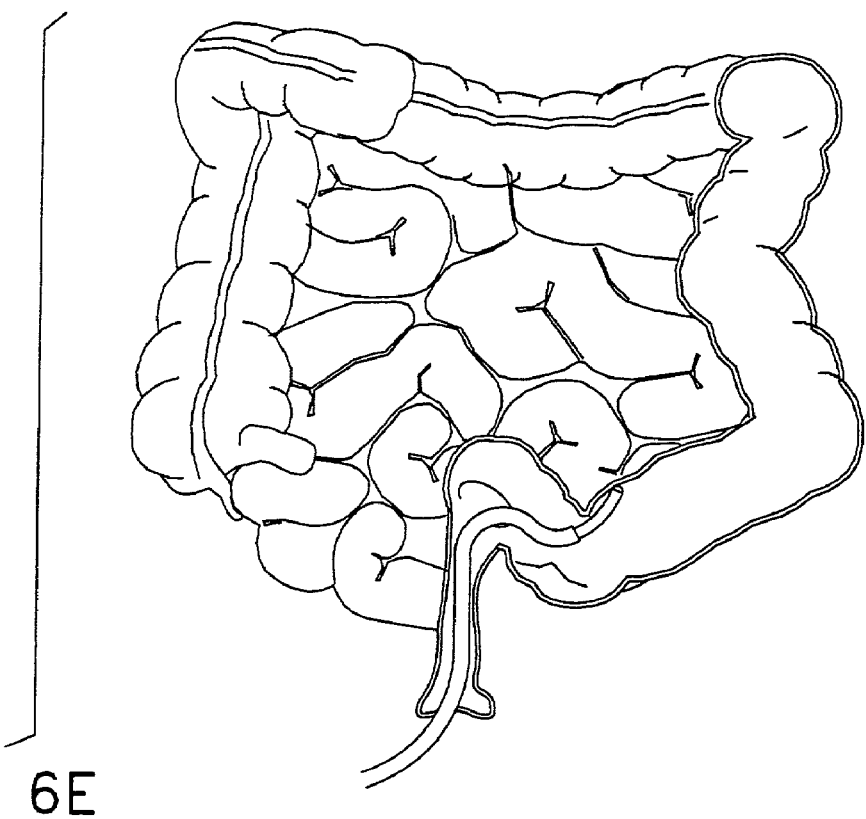
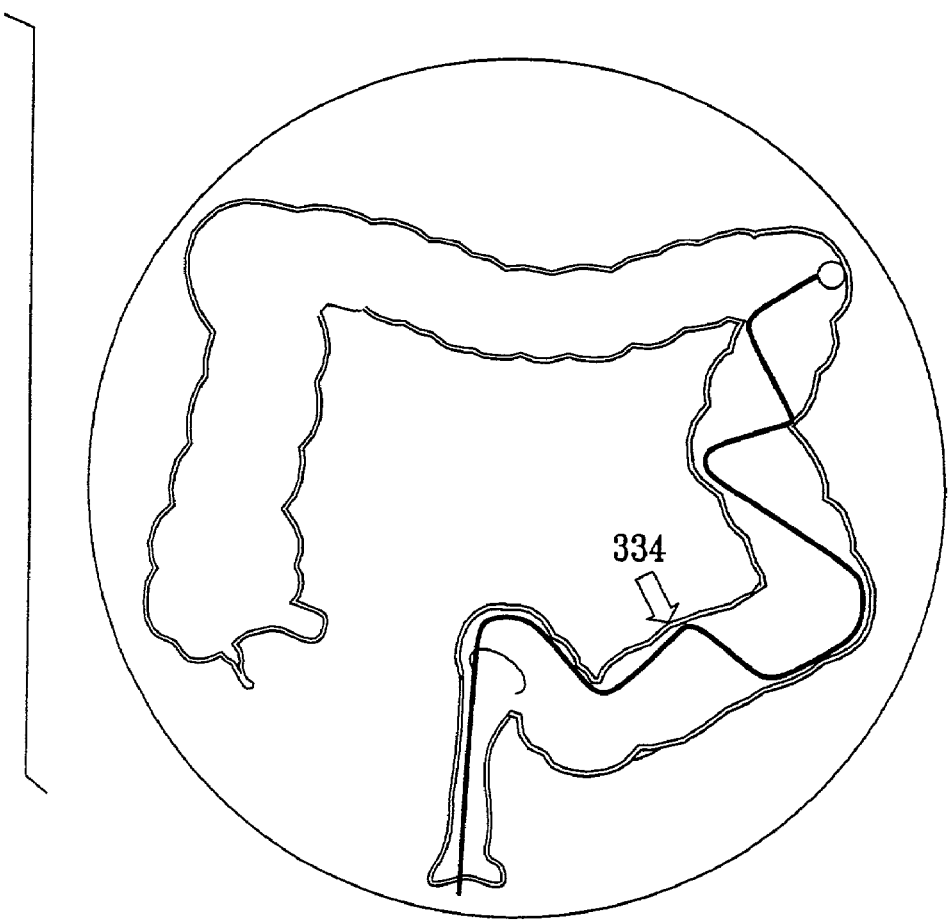
FIG. 6E

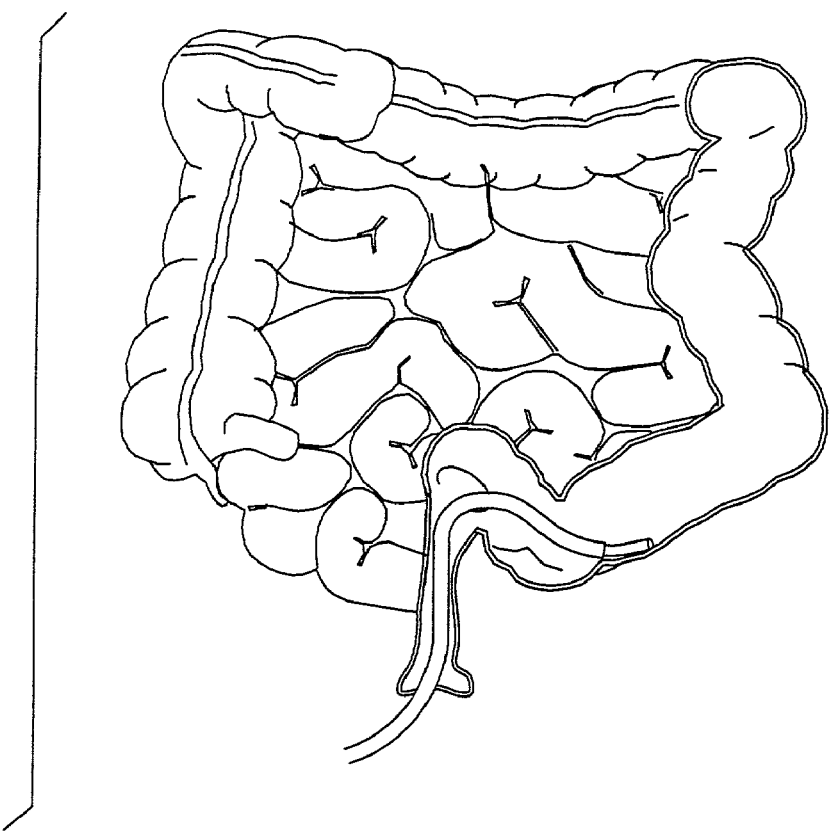
FIG. 6F
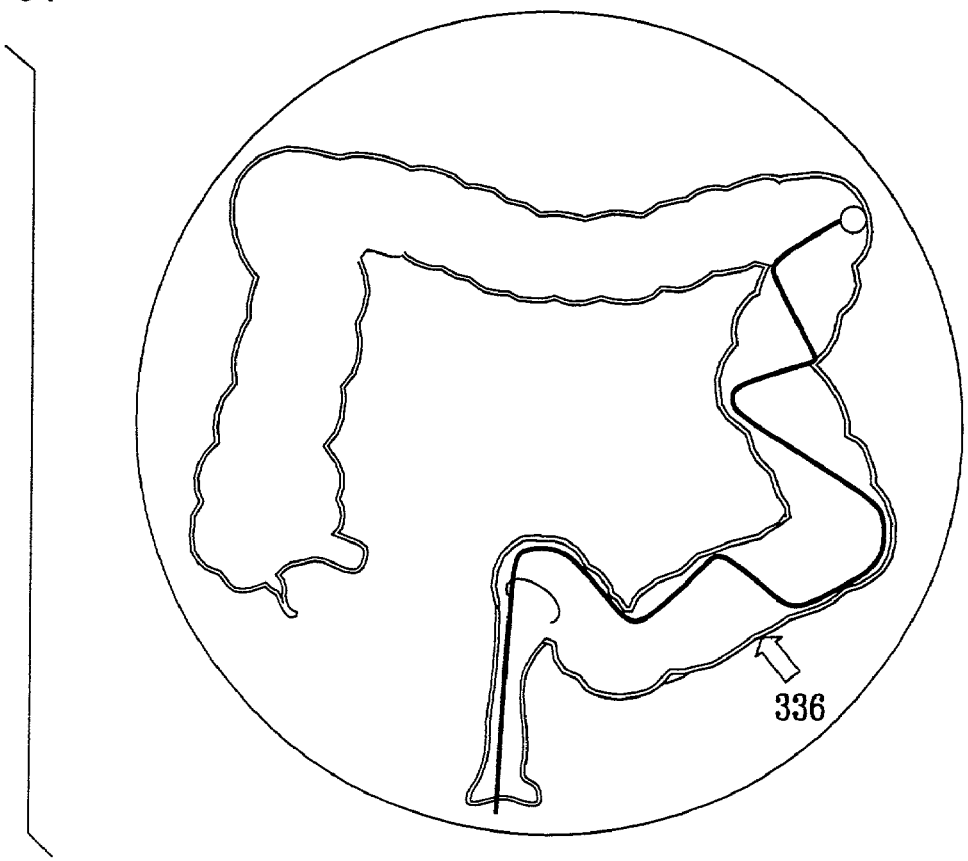
336

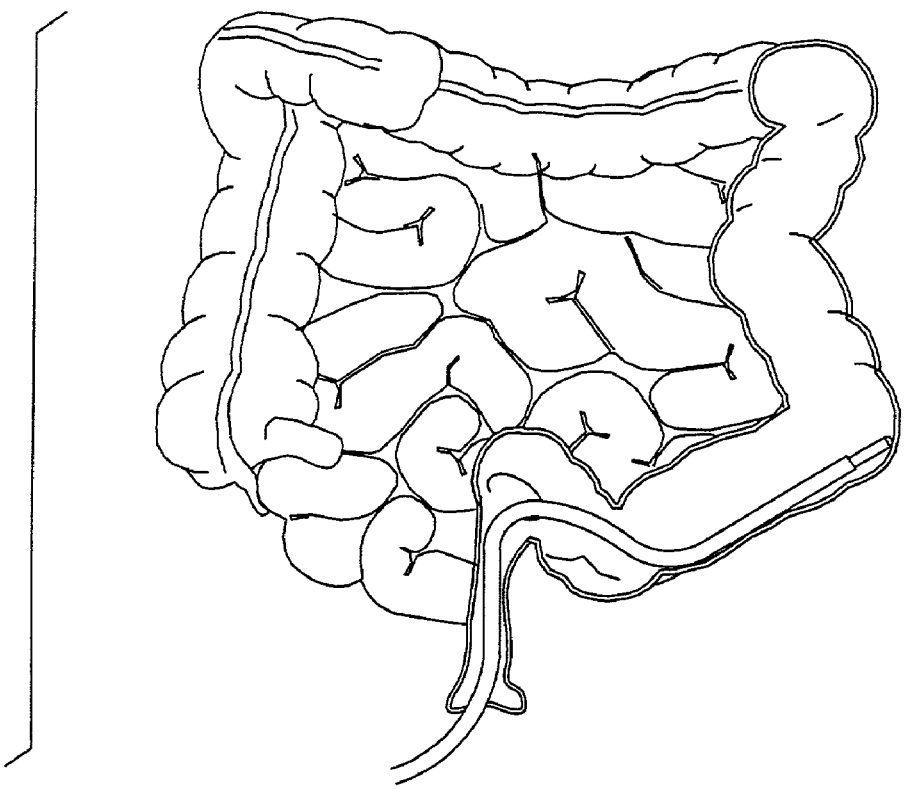
FIG. 6G
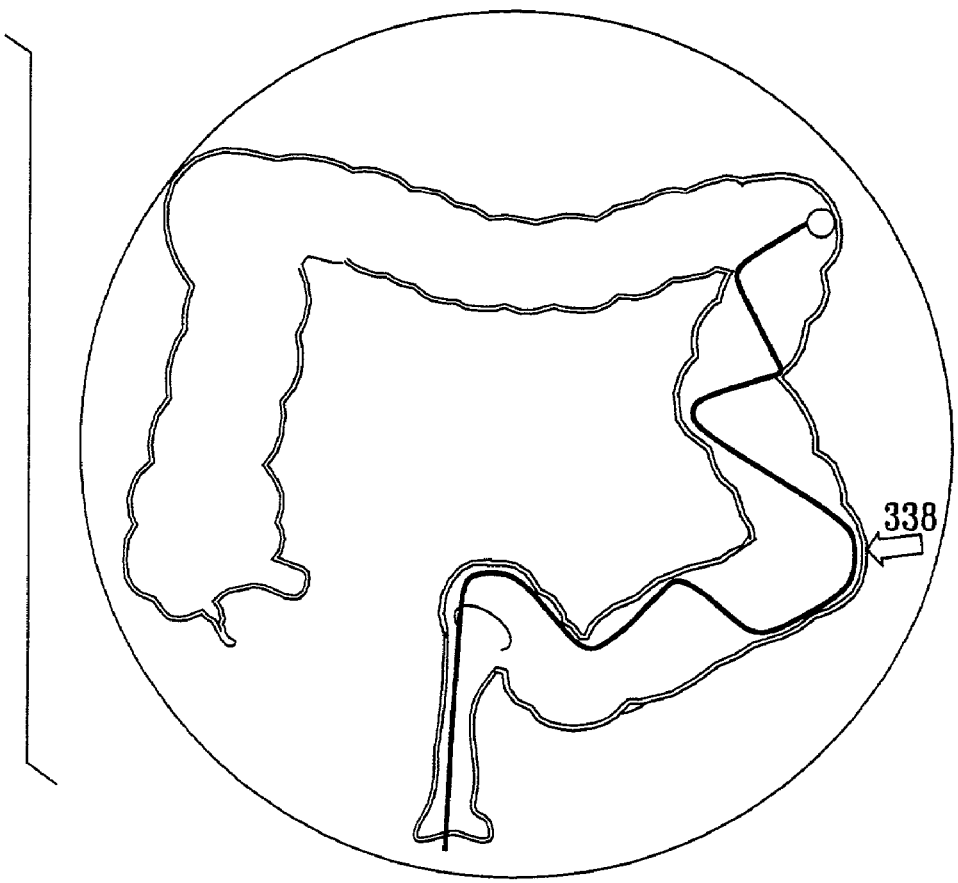

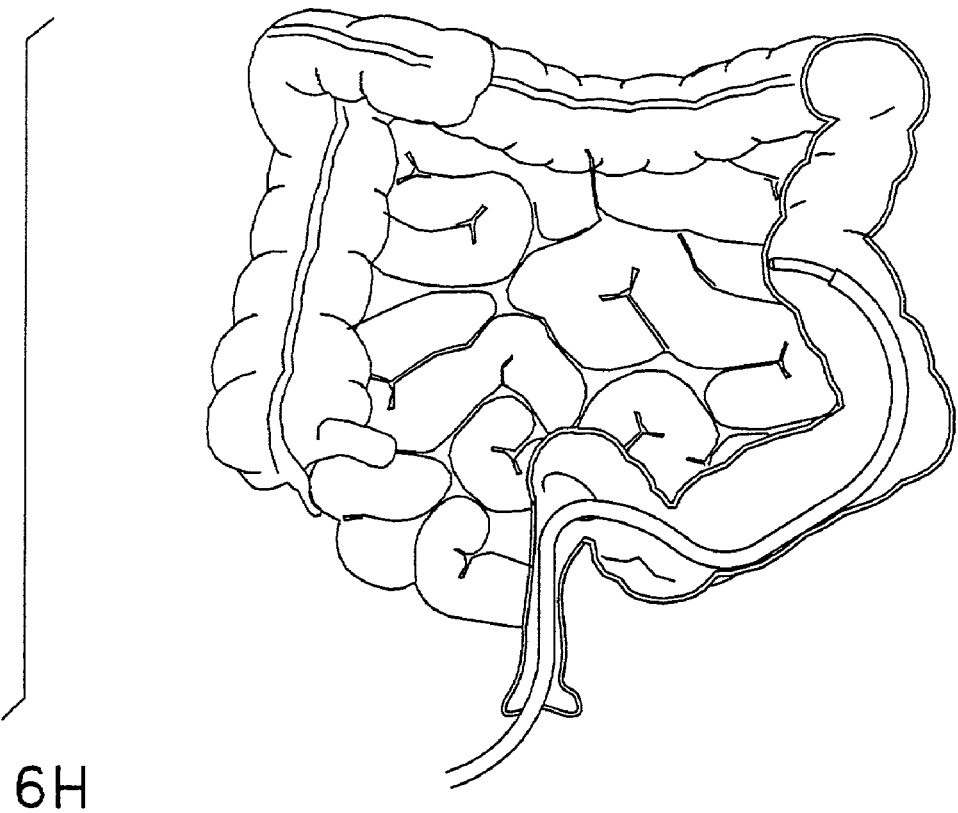
FIG. 6H
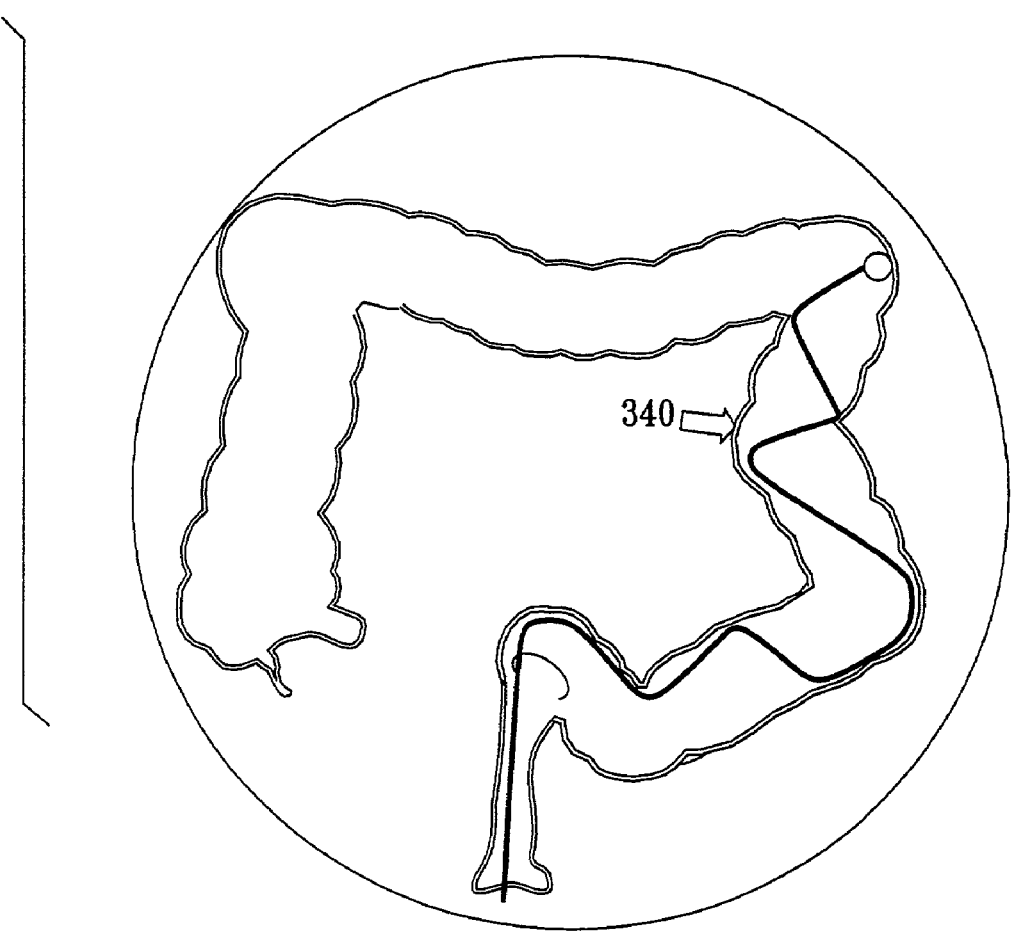
340

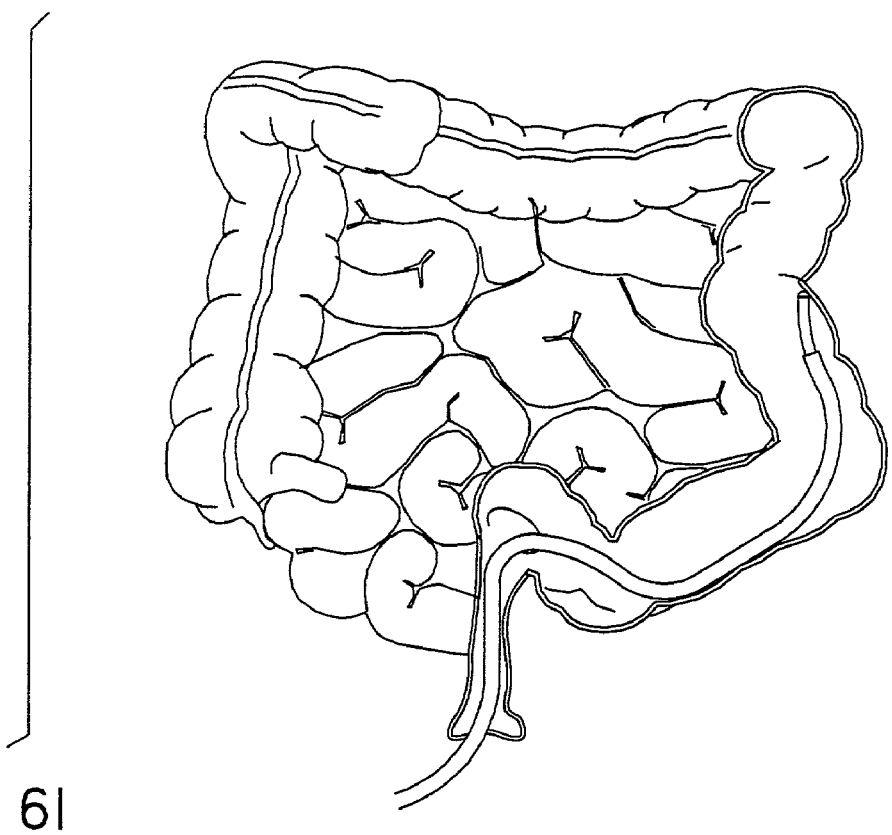
FIG. 61
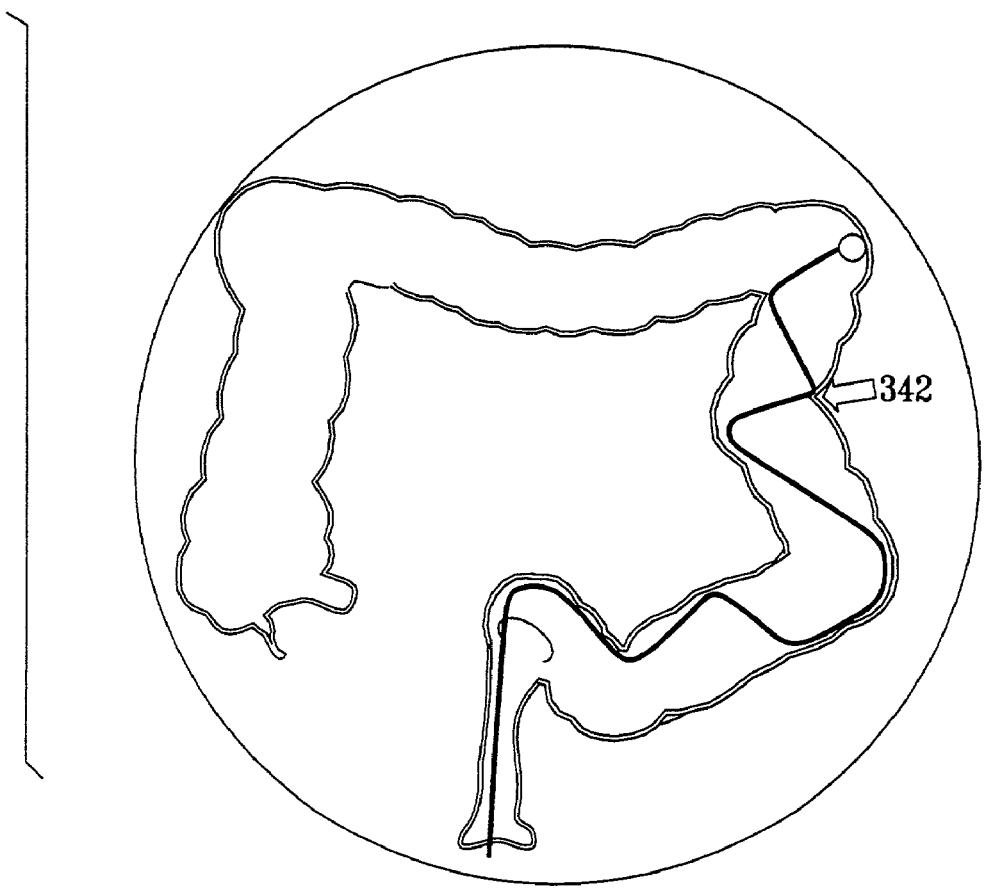

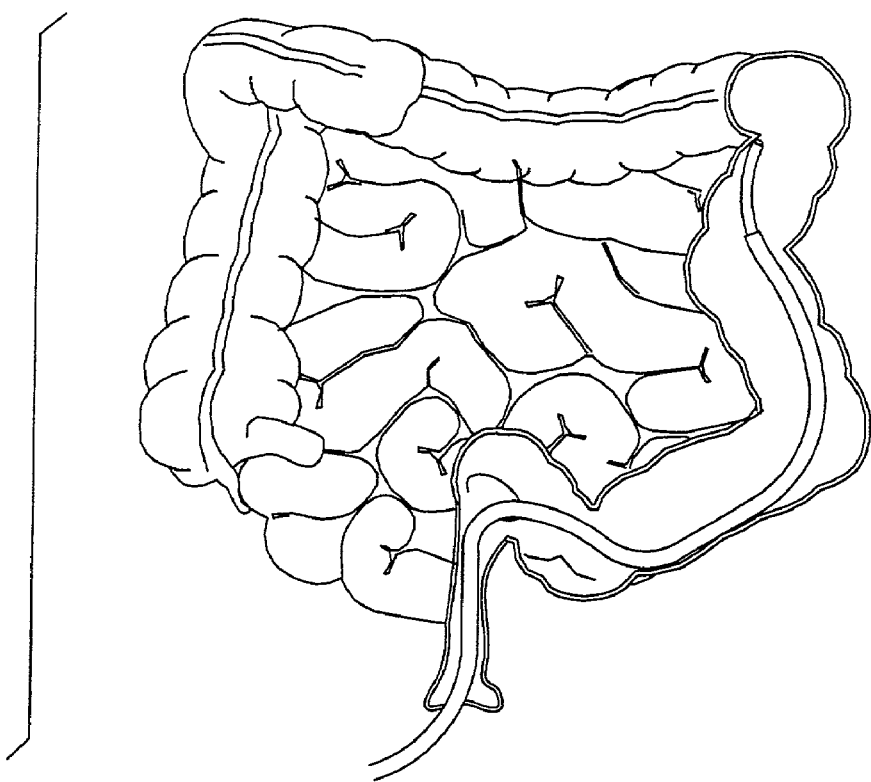
FIG. 6J
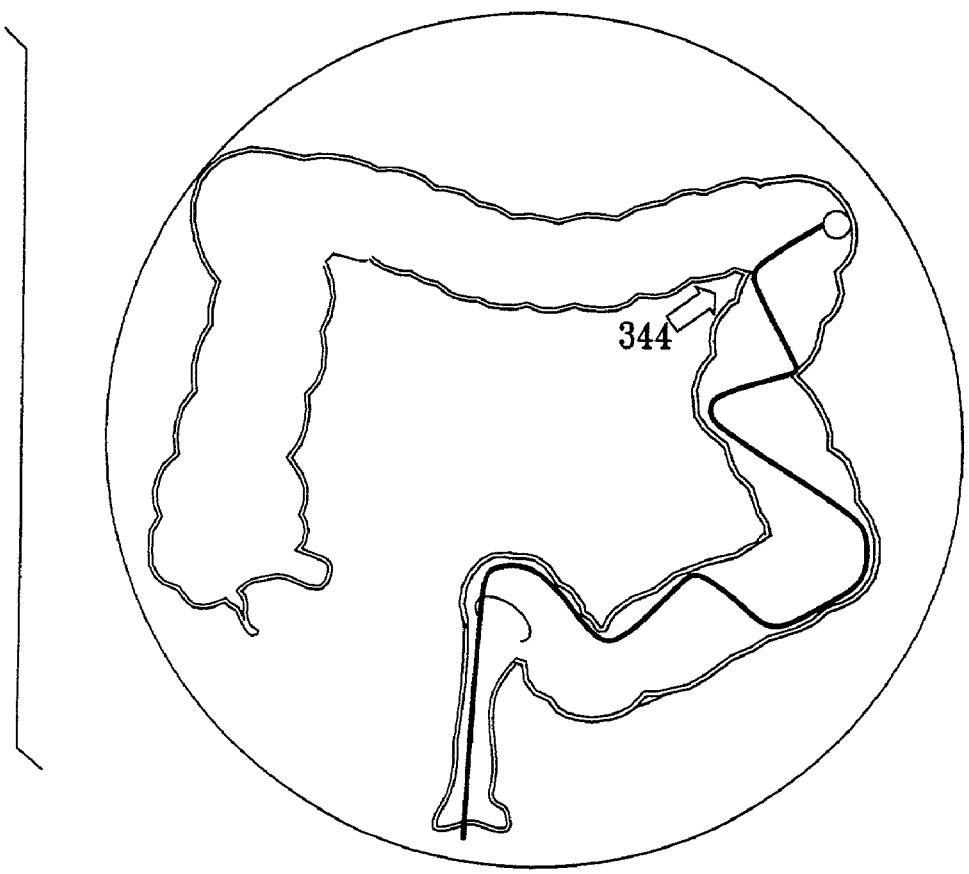

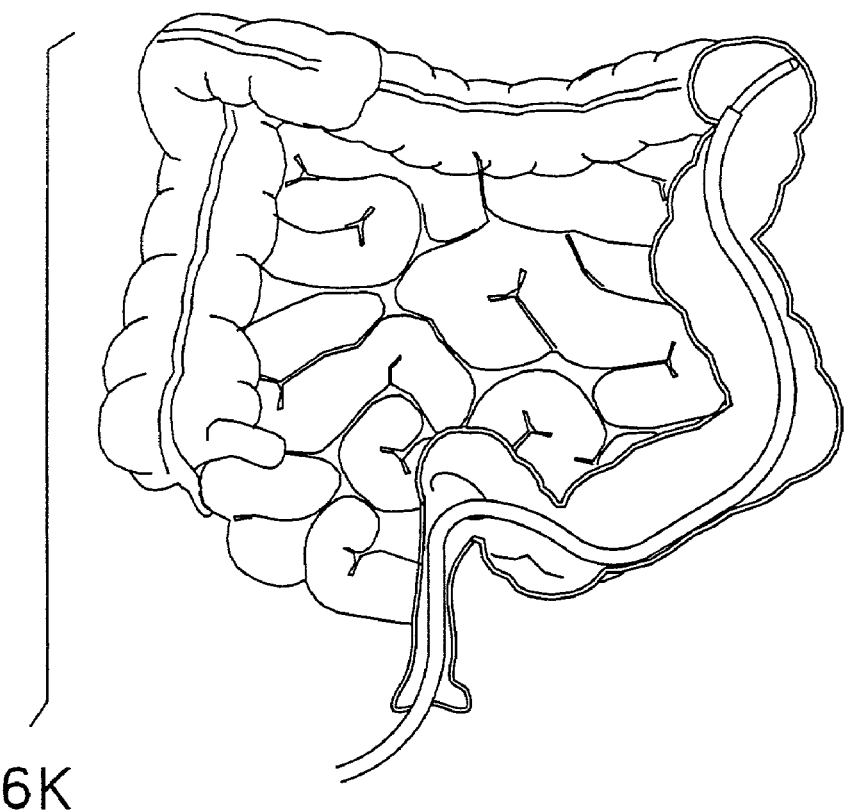
FIG. 6K
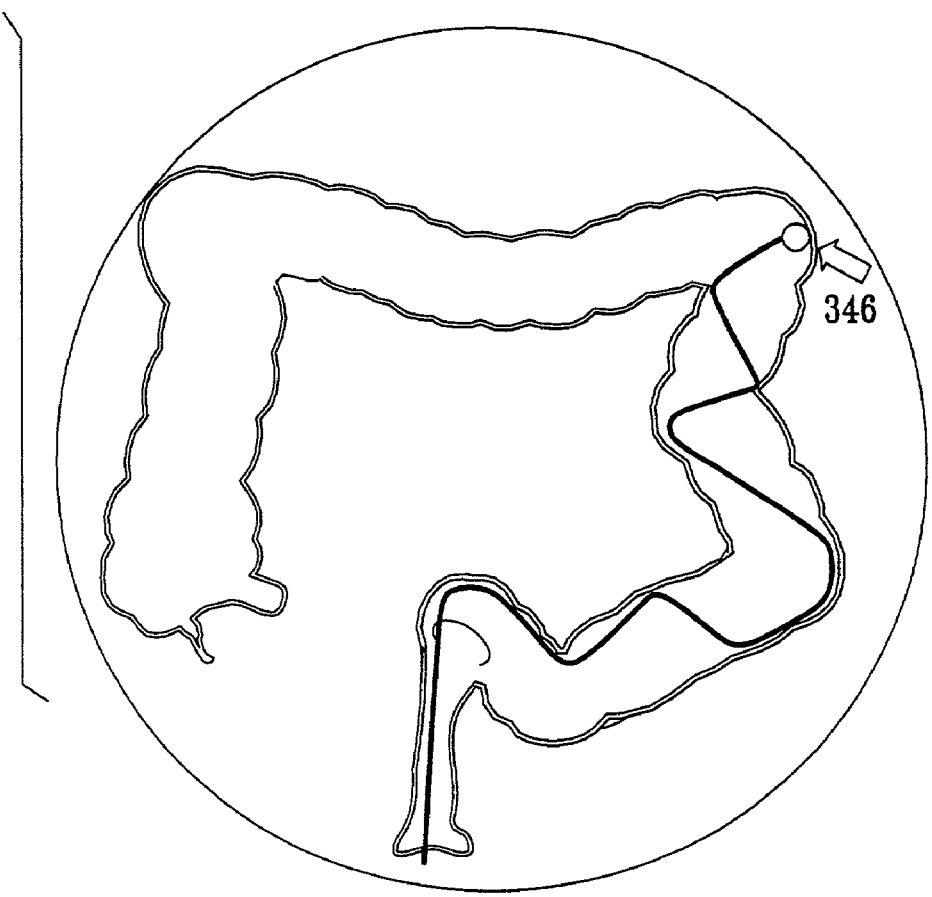
346

FIG 7

| ROW NO. | INITIAL BEND | | INITIAL INSERTION | INITIAL SENSOR MEASUREMENTS | | | | INSERT DISTANCE | FINAL SENSOR MEASUREMENTS | | | |
|---|---|---|---|---|---|---|---|---|---|---|---|---|
| | FRONT | RIGHT | | FRONT | BACK | RIGHT | LEFT | | FRONT | BACK | RIGHT | LEFT |
| 1 | 0 | -45 | 0.5 | 0 | 0 | 0 | 3 | 5 | 9 | 9 | 9 | 9 |
| 2 | 0 | 45 | 0.1 | 0 | 0 | 0 | 4 | 2.5 | 0 | 0 | 0 | 0 |
| 3 | 0 | -110 | 0.1 | 0 | 0 | 0 | 2 | 1 | 0 | 0 | 0 | 3 |
| 4 | 0 | 45 | 1.0 | 0 | 0 | 4 | 0 | 6 | 0 | 0 | 7 | 0 |
| 5 | 0 | 20 | 0.5 | 0 | 0 | 4 | 0 | 4 | 3 | 3 | 7 | 7 |
| 6 | 0 | -60 | 1.0 | 0 | 0 | 0 | 0 | 3 | 9 | 9 | 9 | 9 |
| 7 | 0 | 45 | 2.5 | 0 | 0 | 0 | 0 | 1 | 0 | 0 | 2 | 0 |
| 8 | 0 | 0 | 2.5 | 0 | 0 | 0 | 0 | 1 | 0 | 0 | 0 | 3 |
| 9 | 0 | 45 | 2.5 | 0 | 0 | 0 | 0 | 1 | 9 | 9 | 9 | 9 |

APPARATUS FOR SELF-GUIDED INTUBATION

This application is a continuation of copending International Application PCT/IL01/01121 filed on Dec. 5, 2001, which designated the U.S., claims the benefit thereof and incorporates the same by reference.

FIELD OF THE INVENTION

The present invention relates to systems and methods for automatic insertion of an element into a living organism in vivo.

REFERENCE TO CO-PENDING APPLICATIONS

Applicants hereby claim priority of Israel Patent Application No. 140,136 filed Dec. 6, 2000, entitled "Apparatus For Self-Guided Intubation".

BACKGROUND OF THE INVENTION

The following patents are believed to represent the current state of the art:

6,248,112; 6,236,875; 6,235,038; 6,226,548; 6,211,904; 6,203,497; 6,202,646; 6,196,225; 6,190,395; 6,190,382; 6,189,533; 6,174,281; 6,173,199; 6,167,145; 6,164,277; 6,161,537; 6,152,909; 6,146,402; 6,142,144; 6,135,948; 6,132,372; 6,129,683; 6,096,050; 6,096,050; 6,090,040; 6,083,213; 6,079,731; 6,079,409; 6,053,166; 5,993,424; 5,976,072; 5,971,997; 5,957,844; 5,951,571; 5,951,461; 5,885,248; 5,720,275; 5,704,987; 5,592,939; 5,584,795; 5,506,912; 5,445,161; 5,400,771; 5,347,987; 5,331,967; 5,307,804; 5,257,636; 5,235,970; 5,203,320; 5,188,111; 5,184,603; 5,172,225; 5,109,830; 5,018,509; 4,910,590; 4,672,960; 4,651,746

Reference is also made to: http://www.airwaycam.com/system.html

SUMMARY OF THE INVENTION

The present invention seeks to provide improved systems and methods for automatic insertion of an element into a living organism in vivo.

There is thus provided in accordance with a preferred embodiment of the present invention an automatically operative medical insertion device including an insertable element which is adapted to be inserted within a living organism in vivo, a surface following element, physically associated with the insertable element and being arranged to follow a physical surface within the living organism in vivo, a driving subsystem operative to at least partially automatically direct the insertable element along the physical surface and a navigation subsystem operative to control the driving subsystem based at least partially on a perceived location of the surface following element along a reference pathway stored in the navigation subsystem.

There is also provided in accordance with a preferred embodiment of the present invention an automatically operative medical insertion method, which includes inserting an insertable element within a living organism in vivo, physically associating a surface following element with the insertable element and causing the surface following element to follow a physical surface within the living organism in vivo, automatically and selectably directing the insertable element along the physical surface and controlling direction of the insertable element based at least partially on a perceived location of the surface following element along a reference pathway stored in the navigation subsystem.

Further in accordance with a preferred embodiment of the present invention the driving subsystem is operative to fully automatically direct the insertable element along the physical surface.

Still further in accordance with a preferred embodiment of the present invention the driving subsystem is operative to automatically and selectably direct the insertable element along the physical surface.

Additionally in accordance with a preferred embodiment of the present invention the navigation subsystem receives surface characteristic information relating to the physical surface from the surface following element and employs the surface characteristic information to perceive the location of the surface following element along the reference pathway.

Preferably, the surface characteristic information includes surface contour information.

Additionally in accordance with a preferred embodiment of the present invention the surface characteristic information includes surface hardness information.

Preferably, the surface contour information is three-dimensional,

Preferably, the surface contour information is two-dimensional.

Further in accordance with a preferred embodiment of the present invention the insertable element is a endotracheal tube and wherein the physical surface includes surfaces of the larynx and trachea.

Still further in accordance with a preferred embodiment of the present invention the insertable element is a gastroscope and wherein the physical surface includes surfaces of the intestine.

Additionally in accordance with a preferred embodiment of the present invention the insertable element is a catheter and wherein the physical surface includes interior surfaces of the circulatory system.

Further in accordance with a preferred embodiment of the present invention the insertion device also includes a reference pathway generator operative to image at least a portion of the living organism and to generate the reference pathway based at least partially on an image generated thereby.

Preferably, the reference pathway includes a standard contour map of a portion of the human anatomy.

Further in accordance with a preferred embodiment of the present invention the standard contour map is precisely adapted to a specific patient.

Still further in accordance with a preferred embodiment of the present invention the standard contour map is automatically precisely adapted to a specific patient.

Further in accordance with a preferred embodiment of the present invention the reference pathway is operator adaptable to designate at least one impediment.

Additionally in accordance with a preferred embodiment of the present invention the insertable element includes a housing in which is disposed the driving subsystem, a mouthpiece, a tube inserted through the mouthpiece and a flexible guide inserted through the tube, the surface following element being mounted at a front end of the guide.

Preferably, the mouthpiece includes a curved pipe through which the tube is inserted and the driving subsystem operates to move the guide in and out of the housing, through the curved pipe and through the tube.

Preferably, the driving subsystem also operates to selectably bend a front end of the guide and to move the insertable element in and out of the living organism.

Additionally, the driving subsystem is also operative to selectably bend a front end of the insertable element.

Further in accordance with a preferred embodiment of the present invention the surface following element includes a tactile sensing element.

Preferably, the surface following element includes a tip sensor including a tip integrally formed at one end of a short rod having a magnet on its other end, the rod extends through the center of a spring disk and is firmly connected thereto, the spring disk being mounted on one end of a cylinder whose other end is mounted on a front end of the insertable element.

Further in accordance with a preferred embodiment of the present invention the tip sensor also includes two Hall effect sensors, which are mounted inside the cylinder on a support and in close proximity to the magnet, the Hall effect sensors being spaced in the plane of the curvature of the curved pipe. Each Hall effect sensor includes electrical terminals operative to provide electric current representing the distance of the magnet therefrom. The tip sensor operates such that when a force is exerted on the tip along an axis of symmetry of the cylinder, the tip is pushed against the spring disk, causing the magnet to approach the Hall effect sensors and when a force is exerted on the tip sideways in the plane of the Hall effect sensors, the tip rotates around a location where the rod engages the spring disk, causing the magnet to rotate away from one of the Hall effect sensors and closer to the other of the Hall effect sensors.

Still further in accordance with a preferred embodiment of the present invention the driving subsystem operates, following partial insertion of the insertable element into the oral cavity, to cause the guide to extend in the direction of the trachea and bend the guide clockwise until the surface following element engages a surface of the tongue, whereby this engagement applies a force to the surface following element.

Additionally in accordance with a preferred embodiment of the present invention the navigation subsystem is operative to measure the changes in the electrical outputs produced by the Hall effect sensors indicating the direction in which the tip is bent.

Moreover in accordance with a preferred embodiment of the present invention the navigation subsystem operates to sense the position of the tip and the past history of tip positions and to determine the location of the tip in the living organism and relative to the reference pathway.

Preferably, the navigation subsystem operates to navigate the tip according to the reference pathway and operates to sense that the tip touches the end of the trough beneath the epiglottis.

Further in accordance with a preferred embodiment of the present invention the navigation subsystem is operative to sense that the tip reaches the tip of the epiglottis.

Still further in accordance with a preferred embodiment of the present invention the navigation subsystem operates to sense that the tip reached the first cartilage of the trachea.

Additionally in accordance with a preferred embodiment of the present invention the navigation subsystem operates to sense that the tip reached the second cartilage of the trachea.

Further in accordance with a preferred embodiment of the present invention the navigation subsystem is operative to sense that the tip reached the third cartilage of the trachea.

Preferably, the navigation subsystem operates to load the reference pathway from a memory.

Further in accordance with a preferred embodiment of the present invention the driving subsystem is operative to push the tube forward.

Still further in accordance with a preferred embodiment of the present invention the driving subsystem includes a first motor which operates to selectably move the insertable element forward or backward, a second motor which operates to selectably bend the insertable element and electronic circuitry operative to control the first motor, the second motor and the surface following element.

Preferably, the electronic circuitry includes a microprocessor operative to execute a program, the program operative to control the first and second motors and the surface following element and to insert and bend the insertable element inside the living organism along the reference pathway Further in accordance with a preferred embodiment of the present invention the driving subsystem is operative to measure the electric current drawn by at least one of the first and second motors to evaluate the position of the surface following element.

Still further in accordance with a preferred embodiment of the present invention the reference pathway is operative to be at least partially prepared before the insertion process is activated.

Preferably, the medical insertion device includes a medical imaging system and wherein the medical imaging system is operative to at least partially prepare the reference pathway.

Preferably, the medical imaging subsystem includes at least one of an ultrasound scanner, an X-ray imager, a CAT scan system and an MRI system.

Further in accordance with a preferred embodiment of the present invention the medical imaging system operates to prepare the reference pathway by marking at least one contour of at least one organ of the living organism.

Additionally in accordance with a preferred embodiment of the present invention the medical imaging system operates to prepare the reference pathway by creating an insertion instruction table including at least one insertion instruction.

Preferably, the insertion instruction includes instruction to at least one of extend, retract and bend the insertable element.

Further in accordance with a preferred embodiment of the present invention the navigation subsystem is operative to control the driving subsystem based at least partially on a perceived location of the surface following element and according to the insertion instruction table stored in the navigation subsystem.

Additionally in accordance with a preferred embodiment of the present invention the operative medical insertion device operates to at least partially store a log of a process of insertion of the insertable element and transmits the log of a process of insertion of the insertable element.

Further in accordance with a preferred embodiment of the present invention the computer operates to aggregate the logs of a process of insertion of the insertable element and to prepare the reference pathway based at least partially on the aggregate.

Still further in accordance with a preferred embodiment of the present invention the computer transmits the reference pathway to the medical insertion device.

Further in accordance with a preferred embodiment of the present invention the insertable element includes a guiding element and a guided element.

Additionally in accordance with a preferred embodiment of the present invention the driving subsystem operates to direct the guiding element and the guided element at least partially together.

Further in accordance with a preferred embodiment of the present invention the driving subsystem operates to direct the guiding element and the guided element at least partially together.

Still further in accordance with a preferred embodiment of the present invention the step of directing includes automatically and selectably directing the insertable element in a combined motion, including longitudinal motion and lateral motion.

There is further provided in accordance with a preferred embodiment of the present invention an automatically operative medical insertion device including an insertable element which is adapted to be inserted within a living organism in vivo, a surface following element, physically associated with the insertable element and being arranged to follow a physical surface within the living organism in vivo, a driving subsystem operative to at least partially automatically direct the insertable element along the physical surface and a navigation subsystem operative to control the driving subsystem based at least partially on a perceived location of the surface following element along a reference pathway stored in the navigation subsystem. The insertable element preferably includes a disposable mouthpiece.

There is further provided in accordance with yet another preferred embodiment of the present invention an automatically operative medical insertion method. The method includes inserting an insertable element within a living organism in vivo, physically associating a surface following element with the insertable element and causing the surface following element to follow a physical surface within the living organism in vivo, automatically and selectably directing the insertable element along the physical surface and controlling direction of the insertable element based at least partially on a perceived location of the surface following element along a reference pathway stored in the navigation subsystem. The insertable element preferably includes a disposable mouthpiece.

It is appreciated that the distances and angles referenced in the specification and claims are typical values and should not be construed in any way as limiting values.

BRIEF DESCRIPTION OF THE DRAWINGS AND APPENDICES

The present invention will be understood and appreciated more fully from the following detailed description, taken in conjunction with the drawings and appendices in which:

FIGS. 1A to 1L are a series of simplified pictorial illustrations of a process of employing a preferred embodiment of the present invention for the intubation of a human;

FIGS. 2A to 2F taken together are a flowchart illustrating a preferred implementation of the present invention, operative for an intubation process as shown in FIGS. 1A to 1L;

Figure 8:
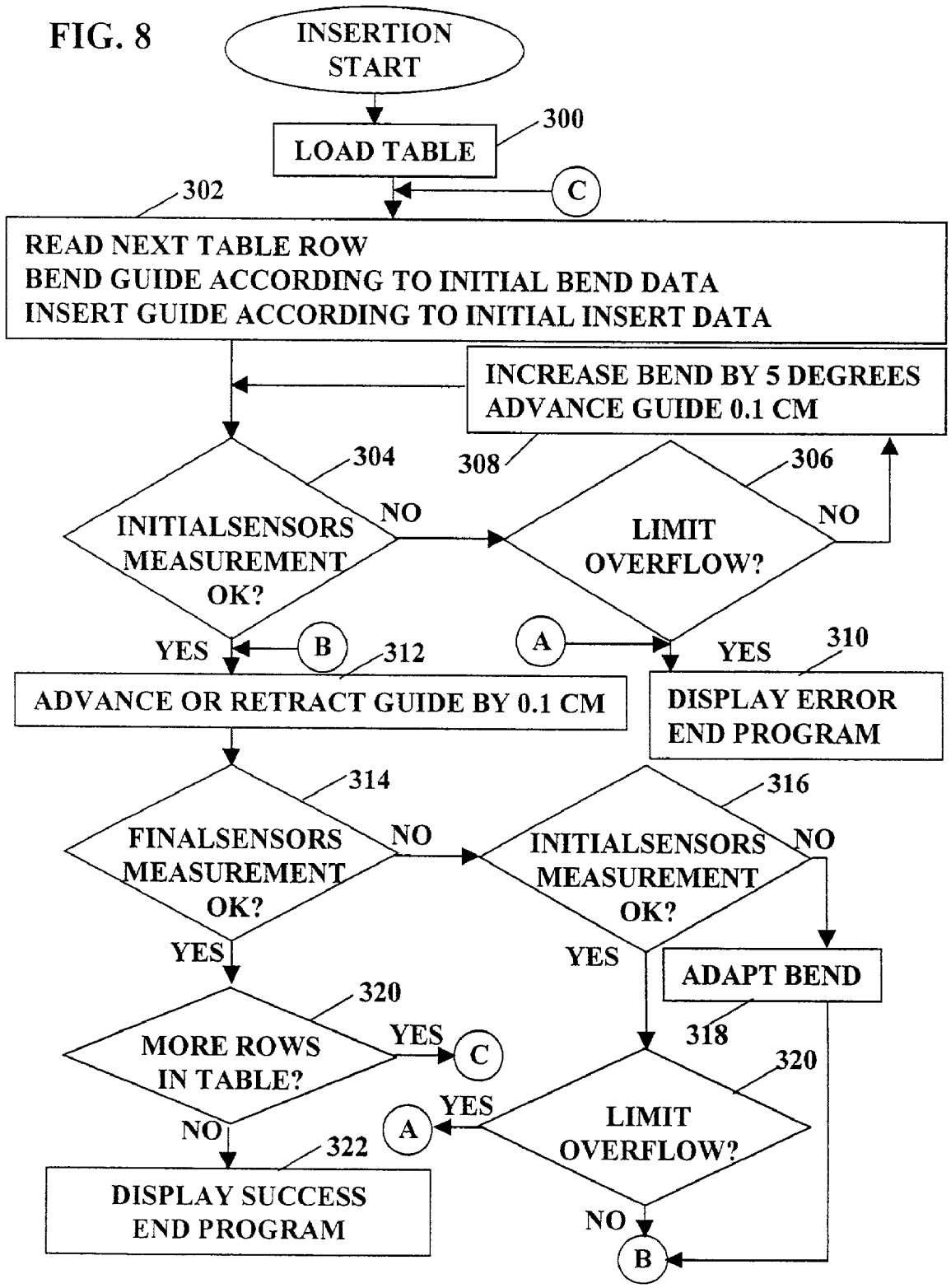

FIGS. 6A to 6K are a series of simplified pictorial illustrations of a process of employing a preferred embodiment of the present invention for insertion of an element into the intestine of a human, FIG. 7 is a preferred embodiment of a table comprising instruction, operative in accordance with a preferred embodiment of the present invention, for insertion of an element into the intestine of a human as shown in FIGS. 5A to 5K;

FIG. 8 is a flowchart illustrating a preferred implementation of the present invention, operative for a process of insertion of an element into the intestine of a human as shown in FIGS. 6A to 6K.

LIST OF APPENDICES

Appendices 1 to 3 are computer listings which, taken together, form a preferred software embodiment of the present invention.

DETAILED DESCRIPTION OF PREFERRED EMBODIMENTS

Reference is now made to FIGS. 1A to 1L, which are a series of simplified pictorial illustrations of a system and methodology for the intubation of a human in accordance with a preferred embodiment of the present invention.

It is appreciated that the general configuration of the mouth and trachea is generally the same for all humans except for differences in scale, such as between an infant, a child and an adult. In a preferred implementation of the present invention, a standard contour map 10 of the human mouth and trachea is employed. The scale of the map 10 may be further precisely adapted to the specific patient, preferably automatically. Alternatively, the scale of the map 10 is adapted to the specific patient semi-automatically. In this alternative the operator can select the scale of the map 10, for example by selecting between a child and an adult. Thereafter the scale of the map 10 is automatically adapted to size of the specific patient as a part of the intubation process. As a further alternative or in addition the operator is enabled to designate one or more typical impediments such as: a tumor, a swelling, an infection and an injury. Selecting an impediment preferably creates a suitable variation of the general map 10.

FIG. 1A shows the map 10 and the location therein where a tip sensor 11 of an intubator engages the mouth and trachea of the patient. It is a particular feature of the present invention that intubation is at least partially automatically effected by utilizing the contour map 10 to monitor the progress of tip sensor 11 and thus to navigate the intubator accordingly.

As seen in FIG. 1A, an intubator assembly 12, suitable for the intubation of a human, is partially inserted into an oral cavity of a patient. The intubator assembly 12 preferably comprises a housing 14 in which is disposed a guide driver 15, a mouthpiece 16, a tube 18 inserted through the mouthpiece 16, a flexible guide 20 inserted through the tube 18, and tip sensor 11 mounted at the distal end of the guide 20. The mouthpiece 16 preferably comprises a rigid curved pipe 24 through which the tube 18 is inserted. Preferably the curved pipe 24 comprises a slit 49 on each side. Alternatively, the curved pipe 24 is eliminated.

It is appreciated that some of the components comprising the intubator assembly 12 may be disposable, for example, the tube 18 and the mouthpiece 16.

The guide driver 15 is operative to move the guide 20 in and out of the housing 14, through the curved pipe 24 and through the tube 18. The guide driver 15 is also operative to selectably bend the distal end of the guide 20 clockwise and counterclockwise in the plane of the curvature of the curved pipe 24 in the sense of FIG. 1A.

Referring now to an enlargement of the tip sensor 11, it is seen that tip sensor 11 preferably comprises a tip 28 preferably integrally formed at one end of a short rod 30 having a magnet 32 on its other end. The rod 30 preferably extends through the center of a spring disk 34 and is firmly connected thereto. The spring disk 34 is preferably mounted on one end of a cylinder 36 whose other end is mounted on the distal end of the guide 20. Preferably, the tip sensor 11 also comprises two Hall effect sensors, 38 and 40, which are mounted inside the cylinder 36 on a support 41 and in close proximity to the magnet 32. The Hall effect sensors 38 and 40 are preferably spaced in the plane of the curvature of the curved pipe 24. Typically, each Hall effect sensor has electrical terminals operative to provide electric current representing the distance of the magnet 32 therefrom.

When a force is exerted on the tip 28 along the axis of symmetry 42 of cylinder 36, the tip 28 is pushed against the spring disk 34, causing the magnet 32 to approach the Hall effect sensors 38 and 40. Since the distance between the magnet 32 and each of the Hall effect sensors 38 and 40 decreases, both Hall effect sensors 38 and 40 produce an increase in their output electric current. When a force is exerted on the tip 28 sideways in the plane of the Hall effect sensors 38 and 40, the tip 28 rotates around the location where the rod 30 engages the spring disk 34, as is shown in FIG. 1A. This causes the magnet 32 to rotate away from the Hall effect sensor 40 and closer to the Hall effect sensor 38. The output electric current of the Hall effect sensor 40 typically decreases and the output electric current of the Hall effect sensor 38 typically correspondingly increases. Thus, it may be appreciated that the tip sensor 11 enables electronic circuitry (not shown) to measure the amplitude and the direction of force exerted on the tip 28 in the plane of the Hall effect sensors 38 and 40 and to compute the orientation of a surface of a tissue against which the sensor tip 28 is depressed, relative to the axis of symmetry 42.

It is appreciated that sensors other than Hall effect sensors can be used to measure the direction and the amplitude of the force exerted on the tip 28, or otherwise to measure the proximity and the orientation of the adjacent surface.

During automatic operation of the system, following partial insertion of the intubator assembly 12 into the oral cavity, as shown in FIG. 1A, the guide driver 15 typically causes the guide 20 to extend in the direction of the trachea 44 and bends the guide 20 clockwise until the tip 28 engages a surface of the tongue 46. This engagement applies a force to tip 28, which causes the tip to rotate counterclockwise wherein the magnet 32 approaches the Hall effect sensor 38. Electronic circuitry (not shown) inside the housing 14, which measures the changes in the electrical outputs produced by the Hall effect sensors 38 and 40, indicates that the tip 28 is bent clockwise.

By sensing the position of the tip and employing the past history of tip positions, the system of the present invention determines the location of the tip sensor 11 in the oral cavity and relative to the map 10. This location is employed in order to navigate the intubator correctly, as described hereinbelow.

Figure 1B:
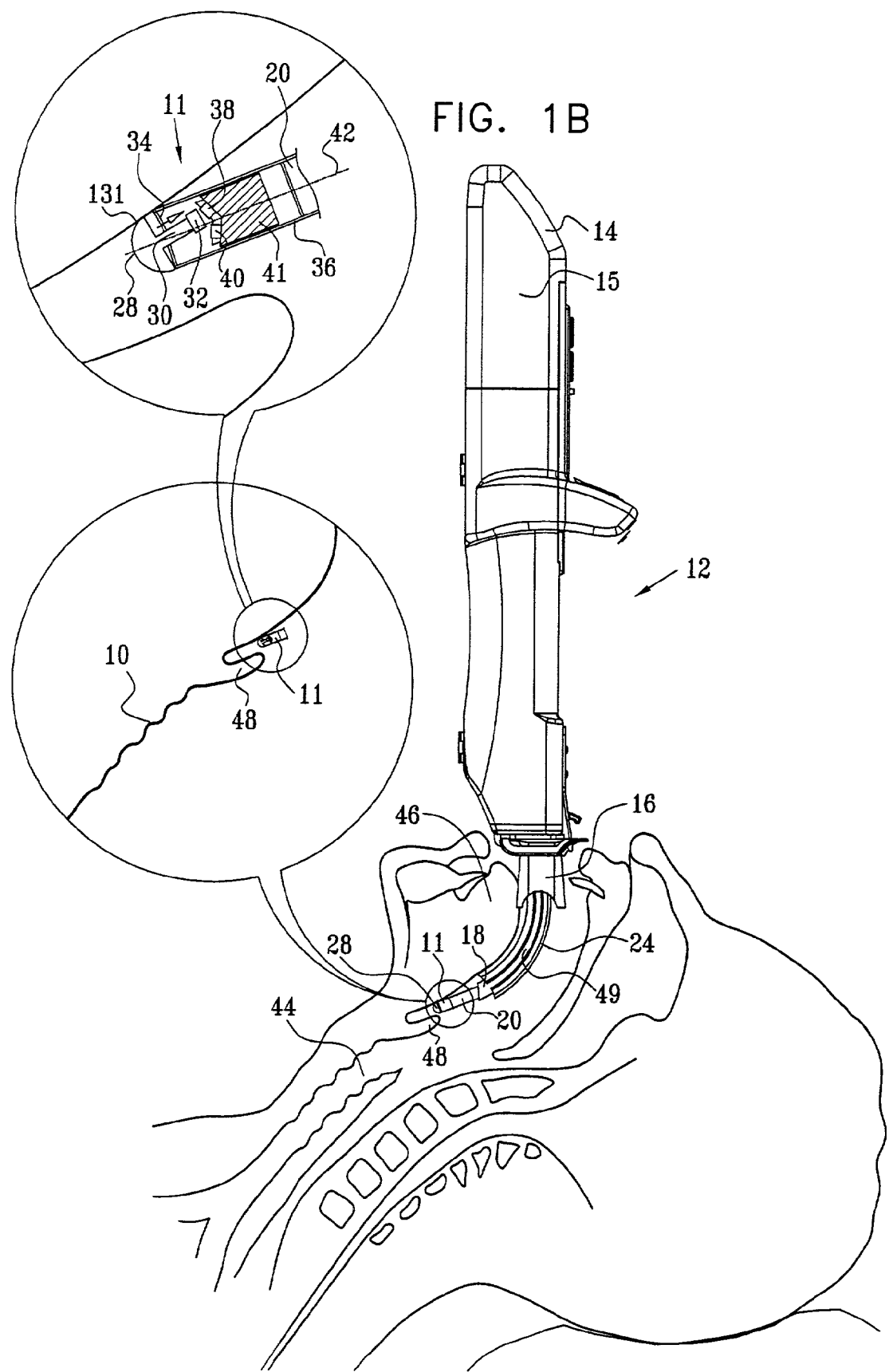

Reference is now made to FIG. 1B, which illustrates a further step in the intubation in accordance with the present invention. FIG. 1B shows the guide 20 extended further and reaching an area between the base of the tongue 46 and the epiglottis 48 of the patient.

Figure 1C:
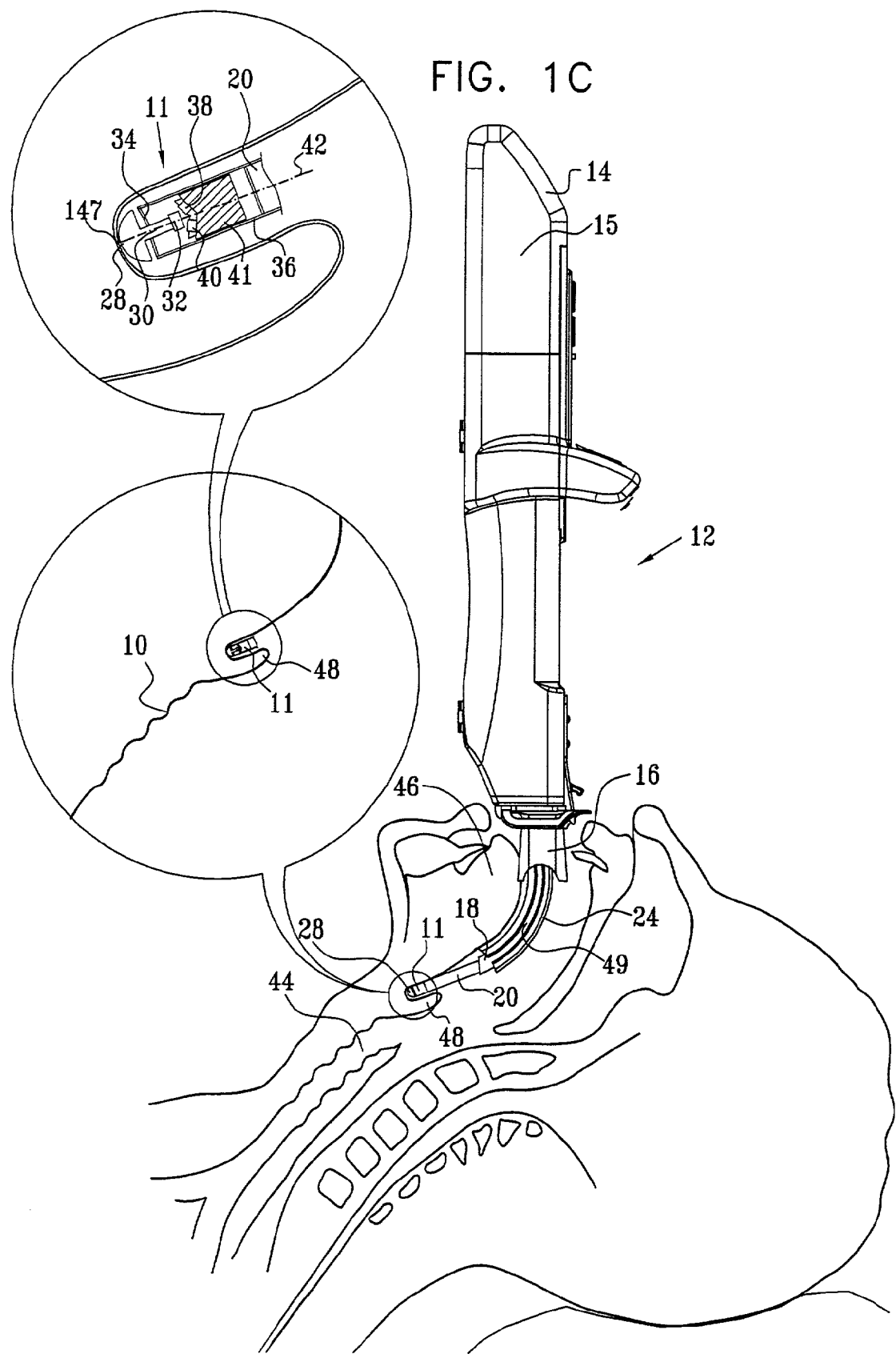

As seen in FIG. 1C, the guide 20 extends further forward until the tip 28 touches the end of the trough beneath the epiglottis 48.

Figure 1D:
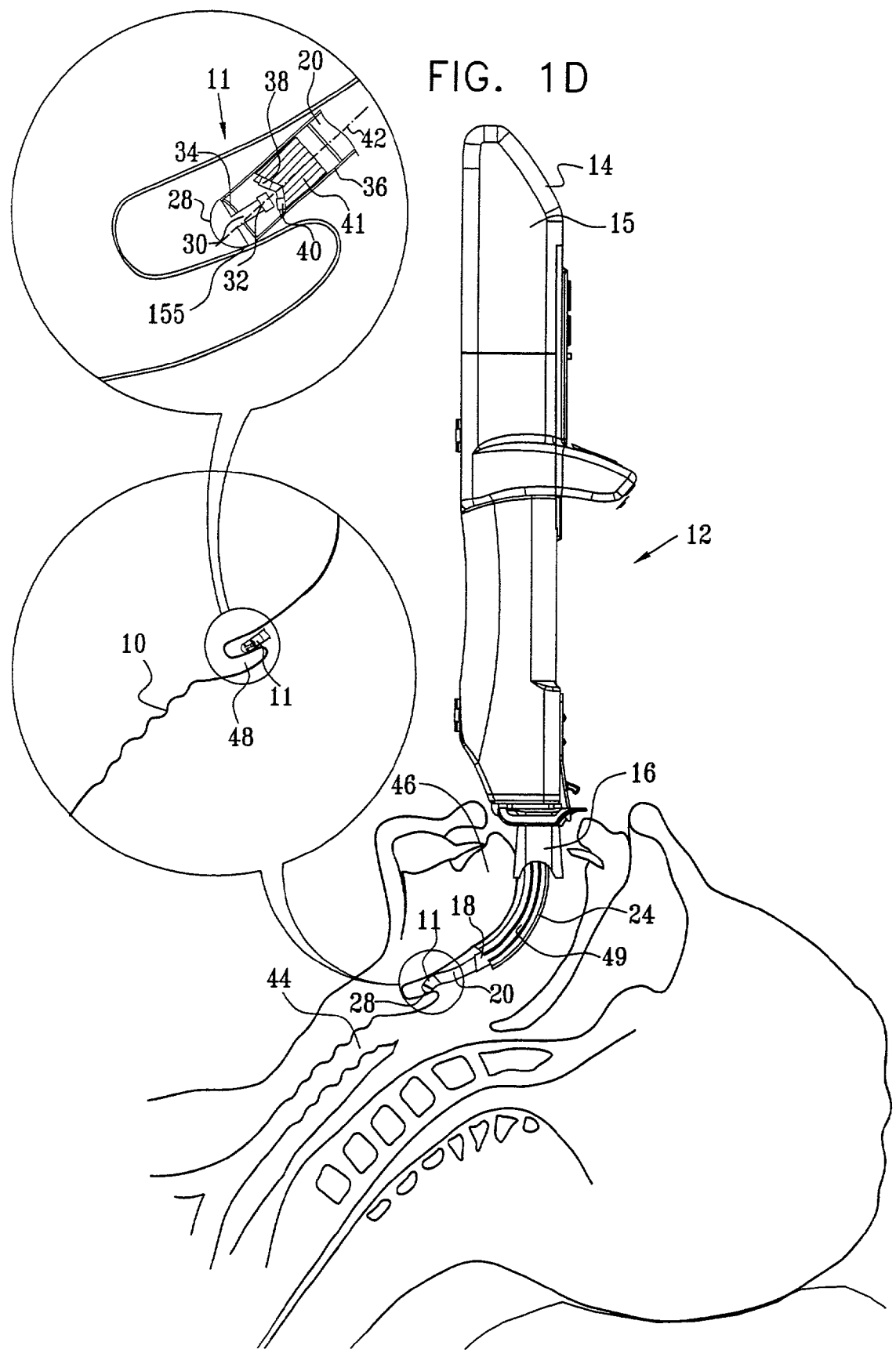

As seen in FIG. 1D, the guide 20 bends counterclockwise and touches the bottom surface of the epiglottis 48. Then the guide 20 retracts a little, while preserving continuous tactile contact between the tip 28 with the bottom surface of the epiglottis 48.

Figure 1E:
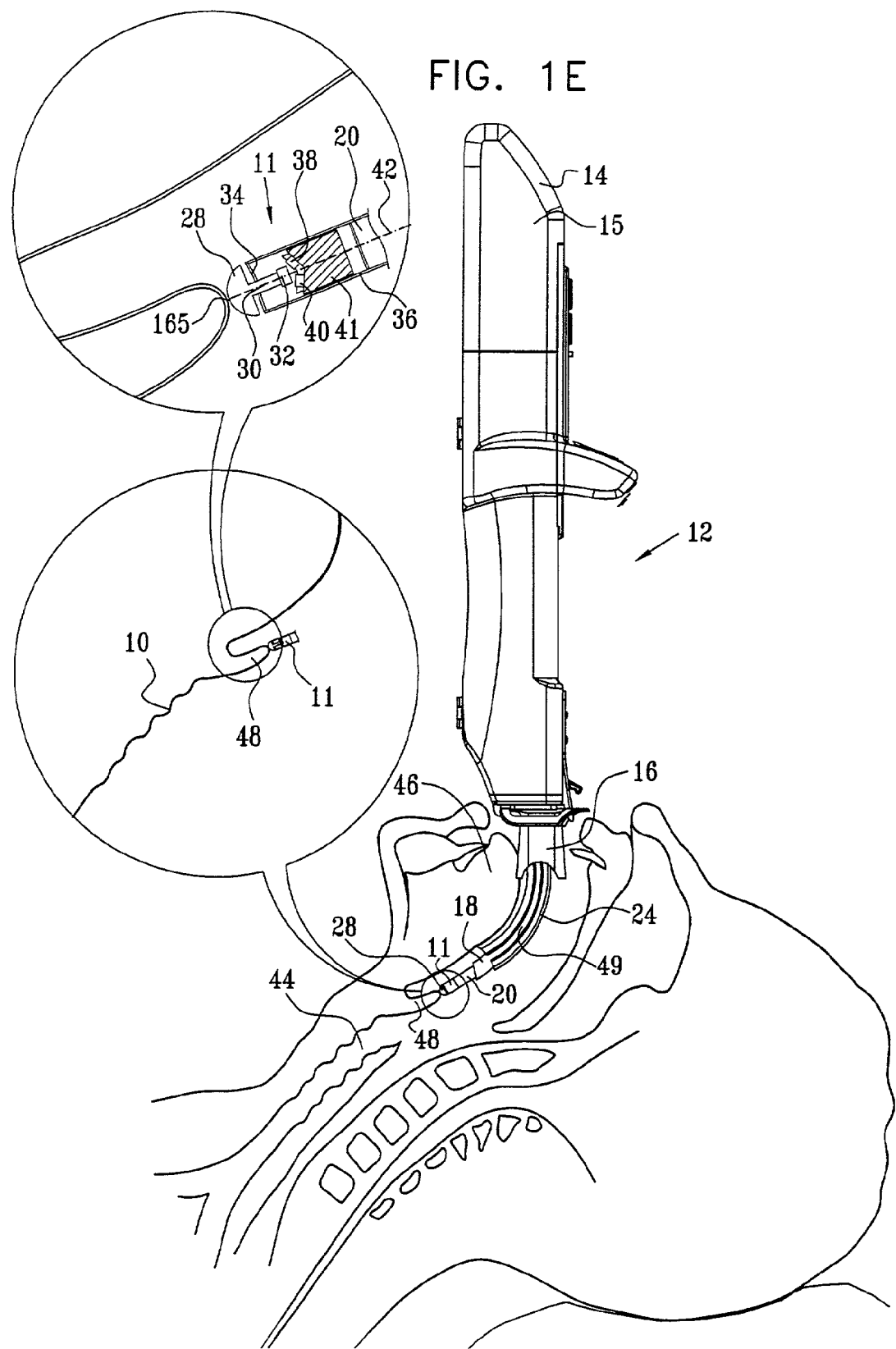

As seen in FIG. 1E, the guide 20 retracts further until the tip 28 of the tip sensor 11 reaches the tip 165 of the epiglottis 48 and then the tip 28 loses tactile contact with the surface of the tip 165 of the epiglottis 48.

Figure 1F:
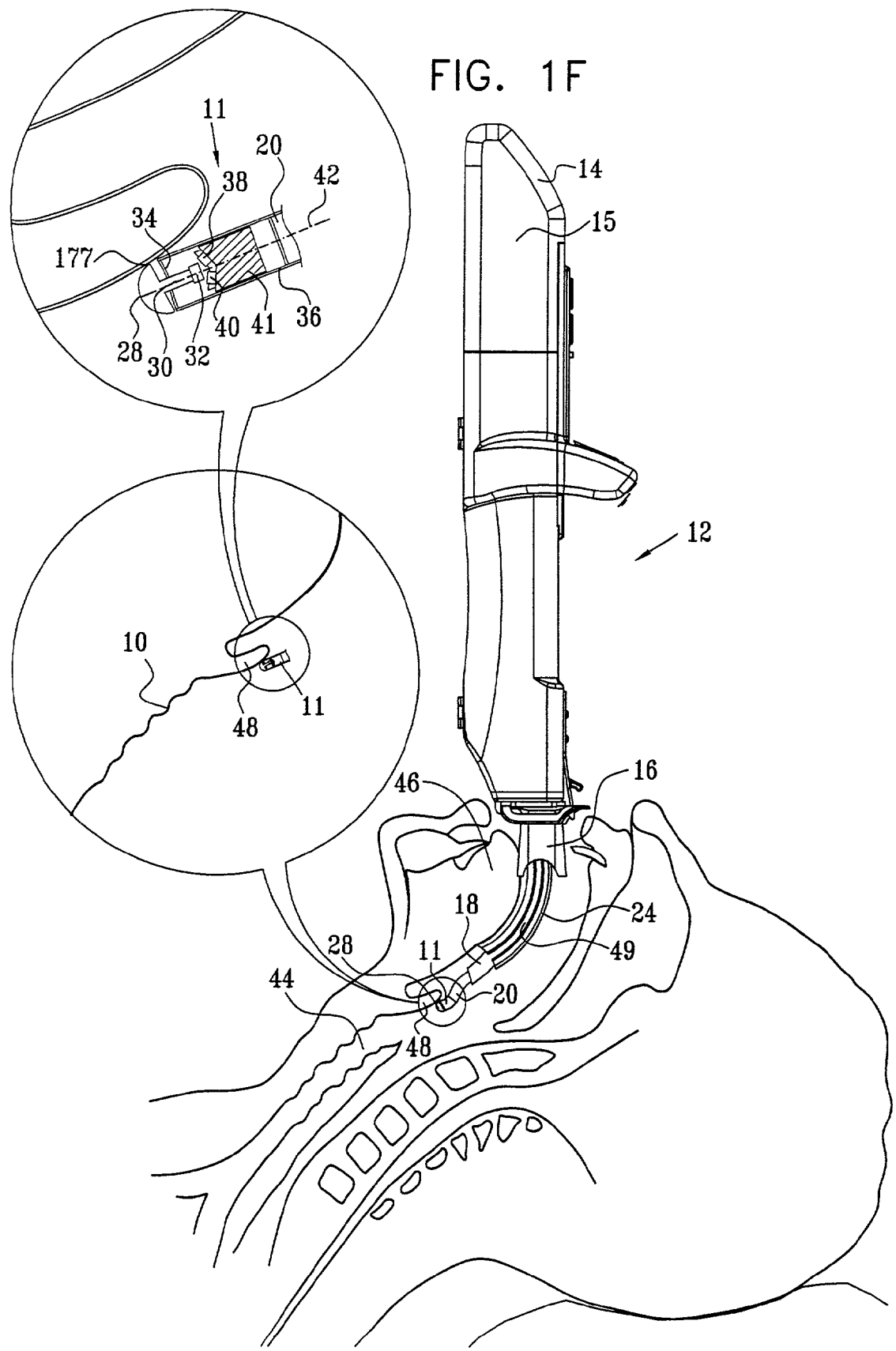

As seen in FIG. 1F, the guide 20 bends further counterclockwise, then extends forward and then bends clockwise until the tip 28 touches the upper surface of the epiglottis 48.

Figure 1G:
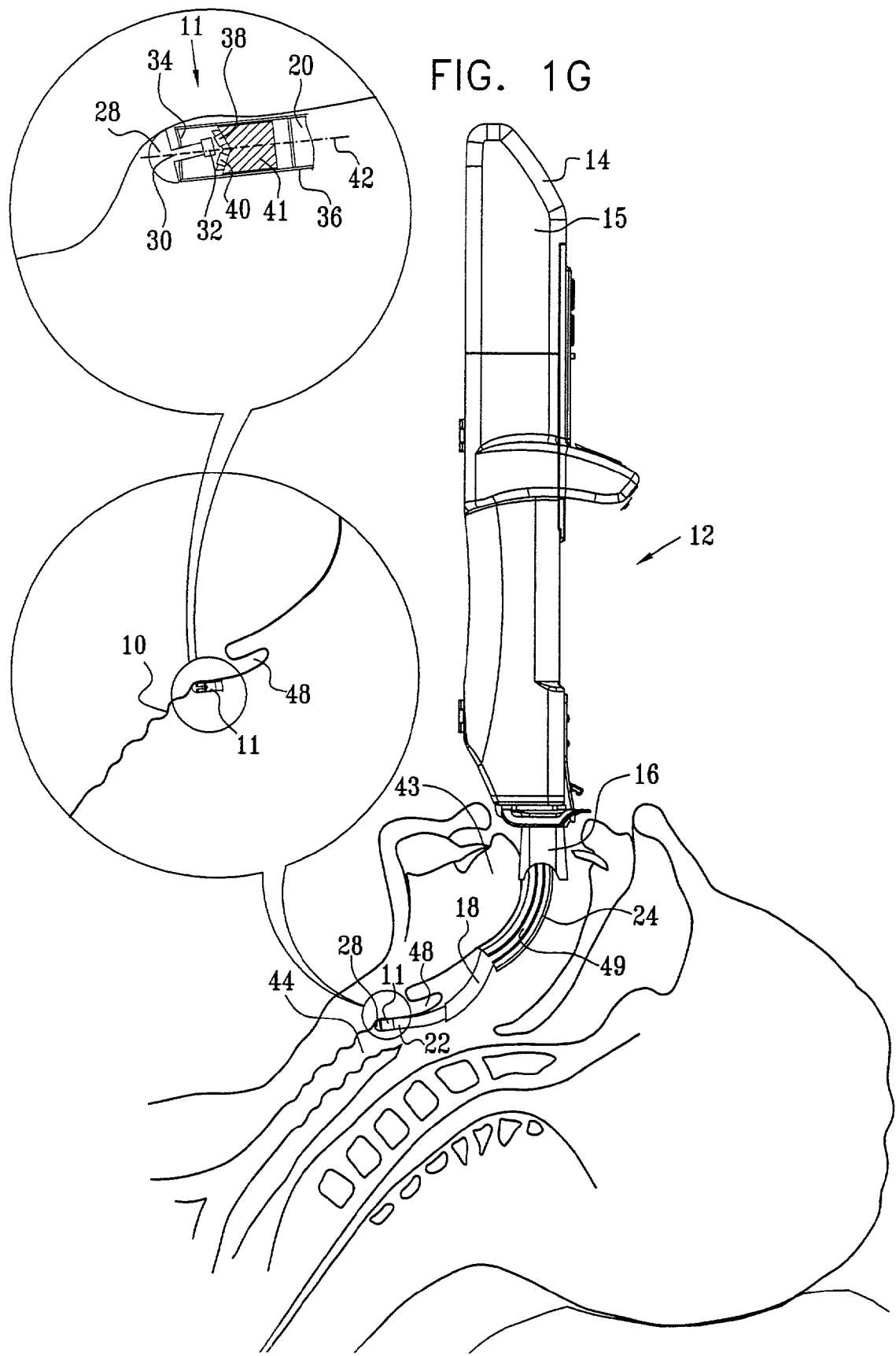

As seen in FIG. 1G, the guide 20 extends forward, preserving continuous tactile contact with the epiglottis 48, until the tip 28 senses the first trough of the trachea 44.

Figure 1H:
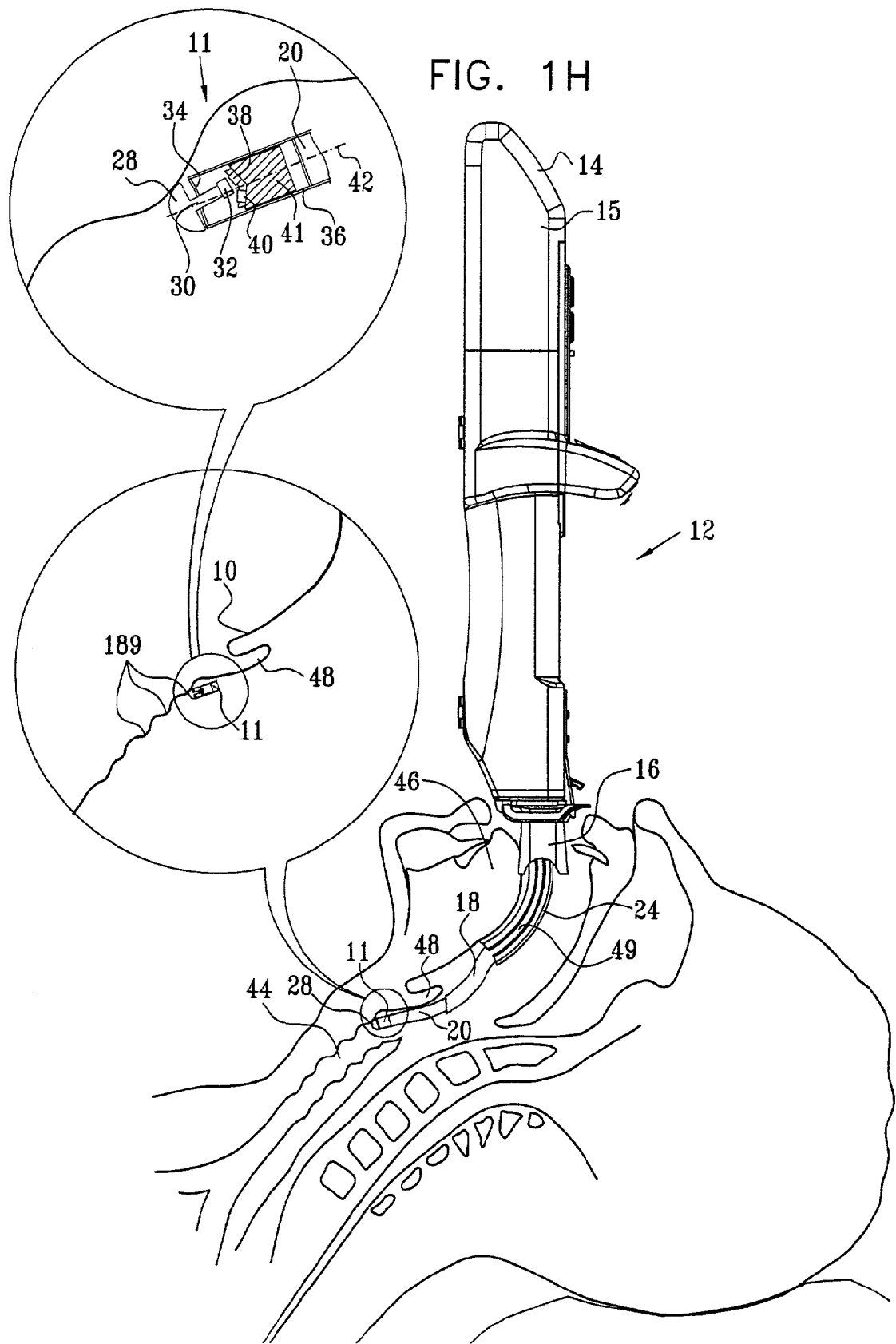

As seen in FIGS. 1H and 1I, the guide 20 extends further forward until the tip 28 senses the second trough of the trachea 44.

Figure 1J:
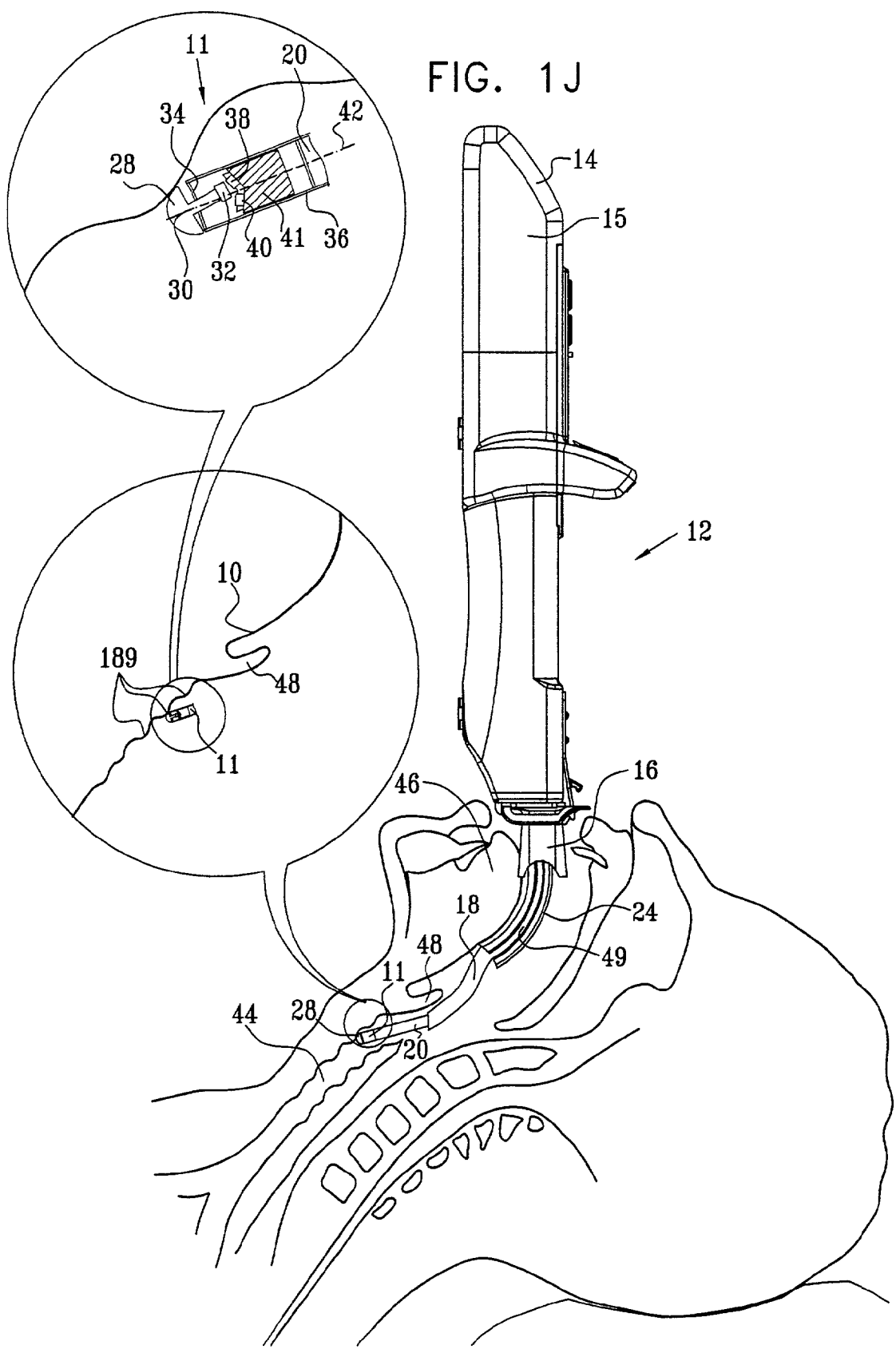
Figure 1K:
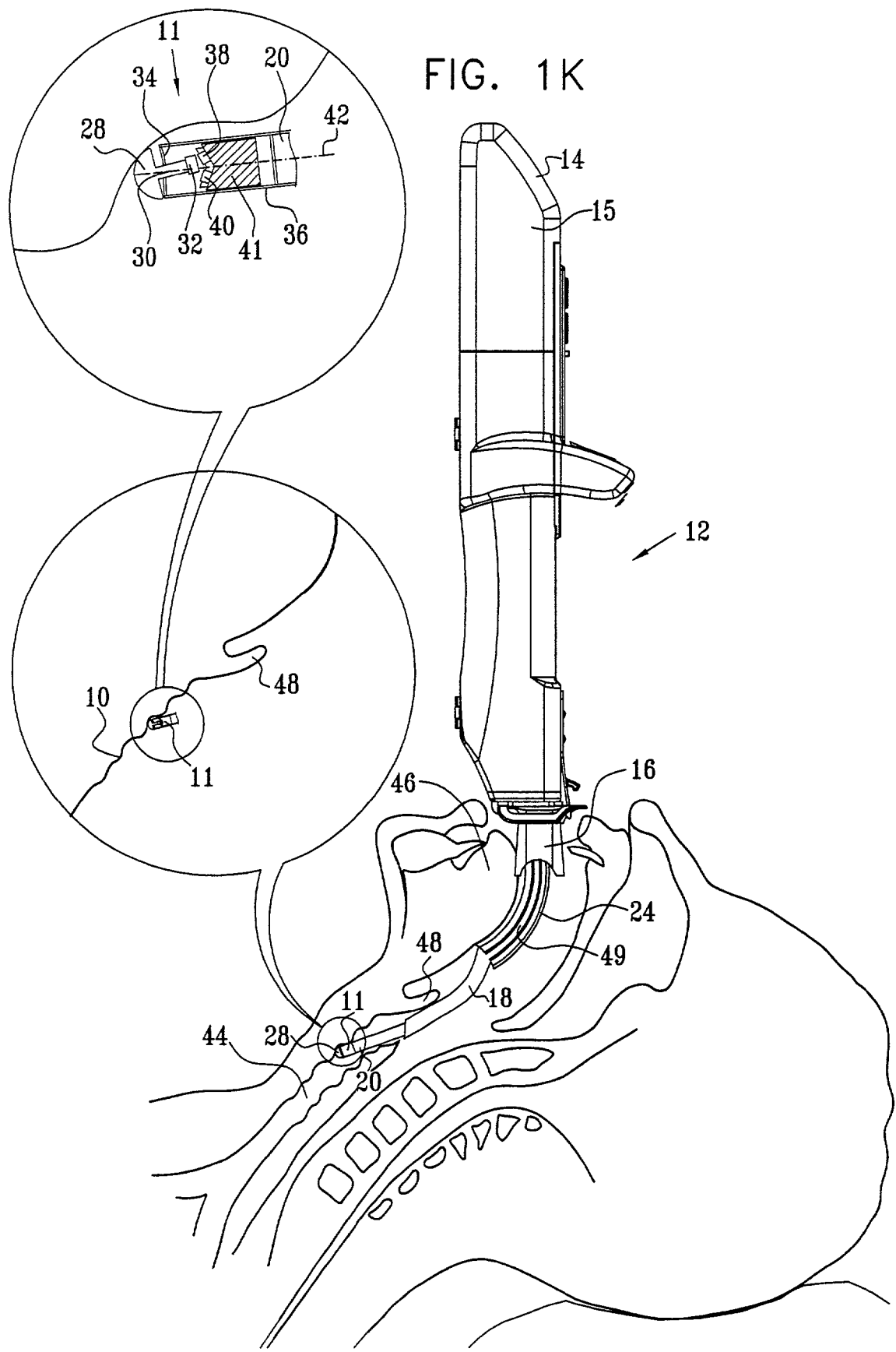

As seen in FIGS. 1J and 1K, the guide 20 extends further forward until the tip 28 senses the trough of the third cartilage of the trachea 44. Then the guide 20 further extends, typically for adults by 5 centimeters, to ensure that the tube 16 reaches to the third cartilage.

Figure 1L:
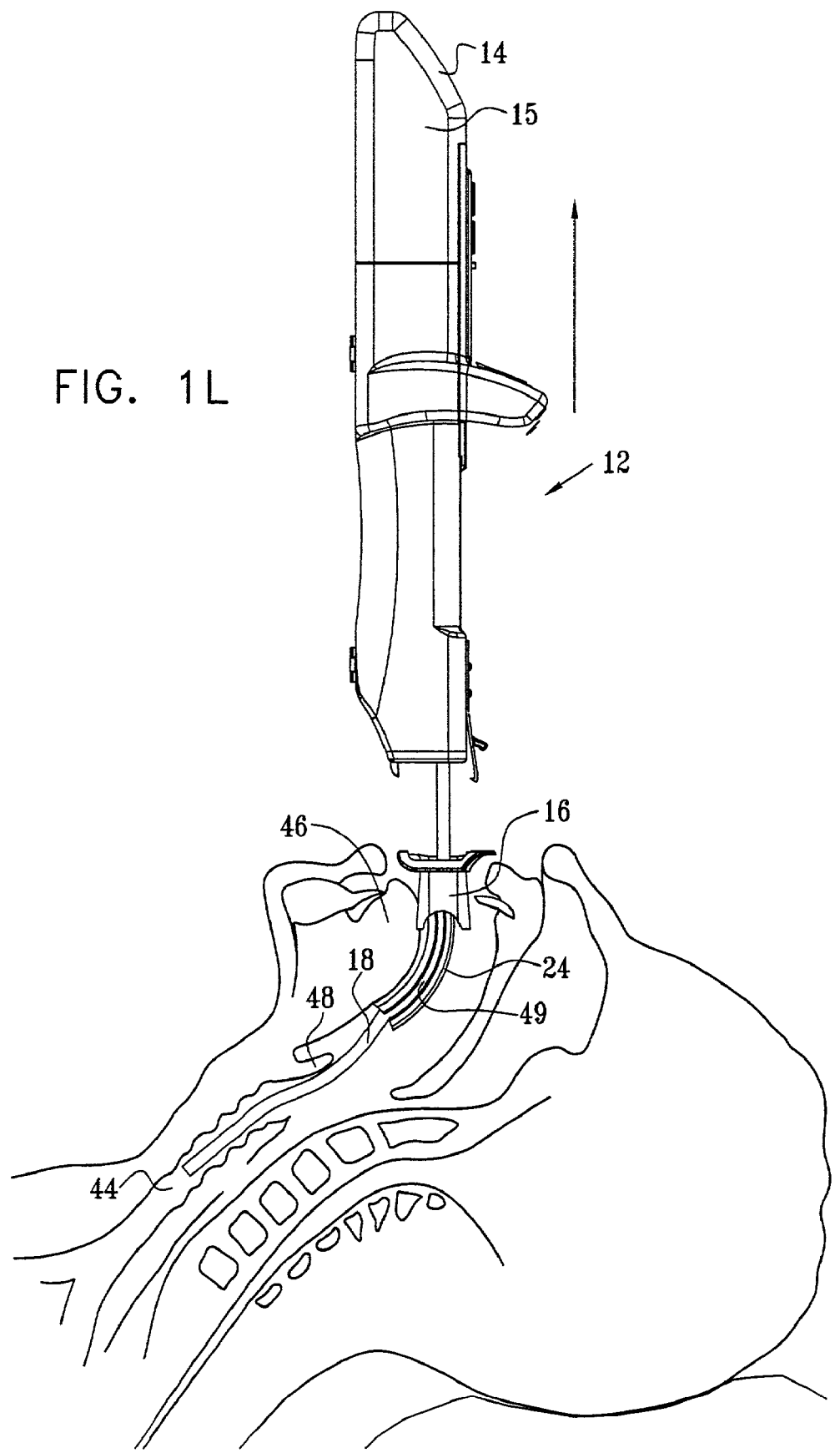

As seen in FIG. 1L, the guide driver 15 is pulled out with the guide 20 leaving the mouthpiece 16 and the tube 18 inside the patient's mouth and trachea 44.

Reference is now made to FIGS. 2A to 2F, which, taken together, are a flowchart of the process of the intubation of a human shown in FIGS. 1A to 1K.

Figure 2A:
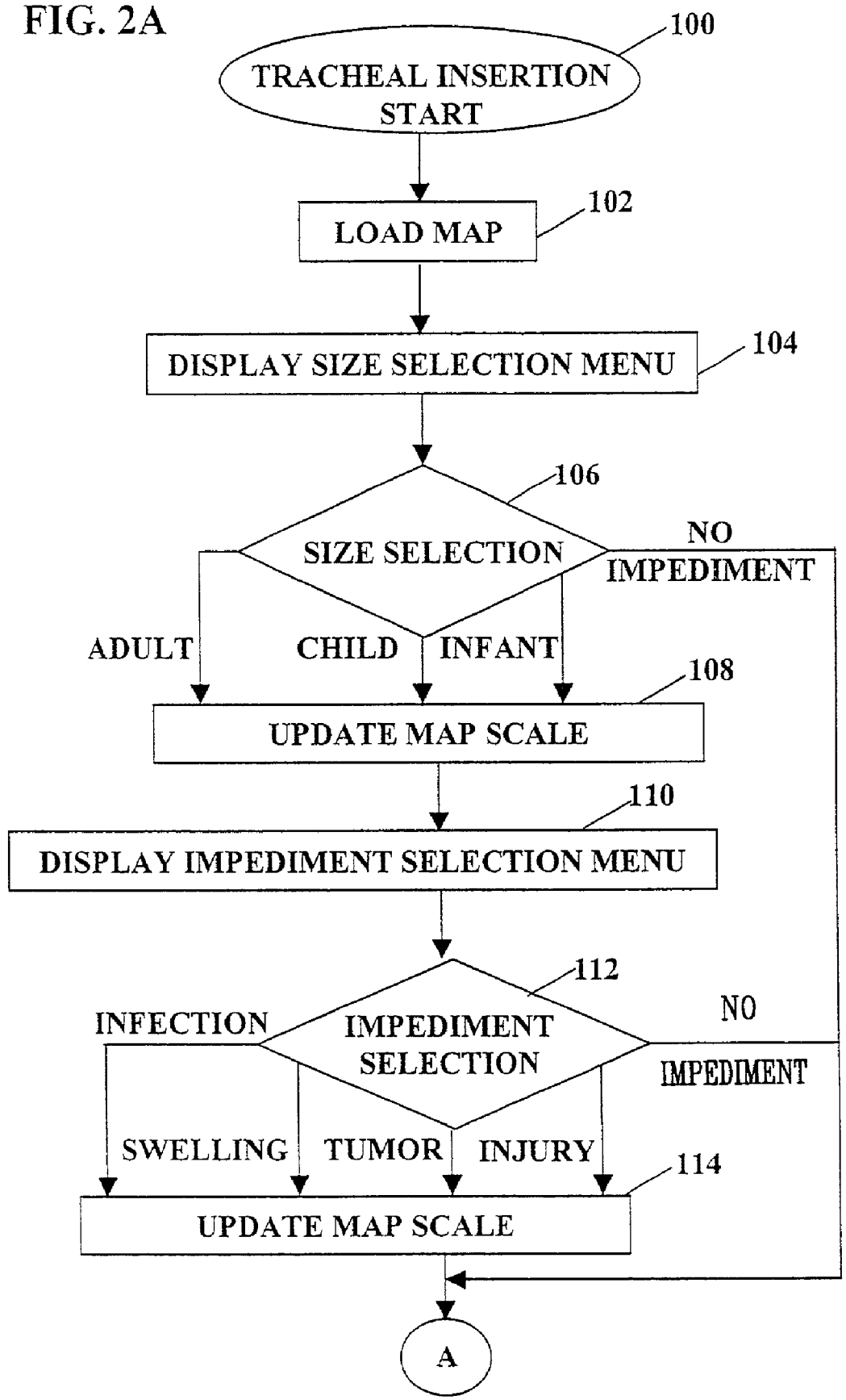
Figure 2B:
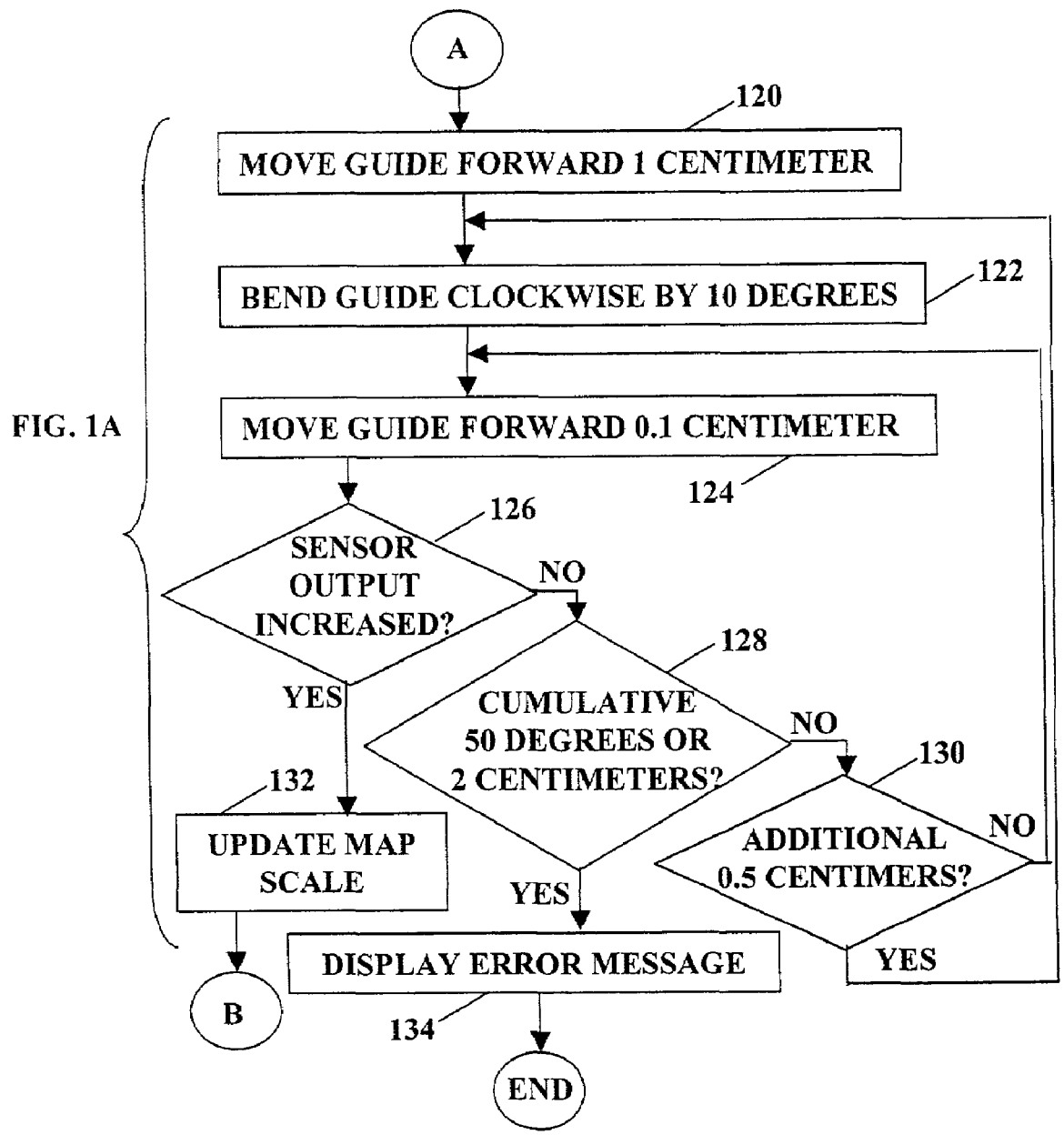

FIGS. 2A and 2B, taken together, correspond to the step of the intubation process shown in FIG. 1A.

In step 100 of FIG. 2A the intubator assembly 12 is set to perform intubation.

In step 102 the intubator loads an intubation pattern map 10 from its memory.

In steps 104, 106 and 108 the intubator enables the operator to set the scale of the intubation pattern map to the corresponding size of the patient by selecting between an infant, a child and an adult.

In steps 110, 112 and 114 the intubator enables the operator to adapt the intubation pattern map 10 to a type of intubation impediment, preferably by selecting from a menu. As seen in FIG. 2A the menu typically provides the operator with four optional impediments: an infection, a swelling, a tumor and an injury, and a fifth option not to select any impediment. It is appreciated that various types of impediments can be defined as is typical for a specific organ.

As seen in FIG. 2B, steps 120, 122, 124, 126, 128 and 130 cause the guide 20 to extend in the direction of the throat and simultaneously bend clockwise until the tip sensor is depressed against the surface of the tongue or until extension and bending limits are reached. As seen in step 128, the bending limit is preferably 50 degrees and the extension limit is preferably 2 centimeters. If the tip sensor is depressed, the scale of the intubation pattern map 10 is preferably updated (step 132) to match the particular scale or size of the intubated patient. If at least one of the extension limit and the bending limit is reached an error message is displayed (step 134) and the intubation process is stopped.

Reference is now made to FIG. 2C, which corresponds to FIGS. 1B and 1C. As illustrated in FIG. 2C, the guide driver 15 performs sequential steps 140, 142, 144 and 146 in a loop, extending (step 140) guide 20 further into the patient's throat and along the throat surface, following the intubation pattern map 10 and keeping the tip in contact with the surface (steps 144, 146). When the output electric currents from both Hall effect sensors 38 and 40 increase, the intubator assumes (step 142) that the tip 28 has reached the end of the trough beneath the epiglottis 48. The point of engagement between the tip 28 and the body is designated in FIG. 1C by reference numeral 147. The scale of the intubation pattern map 10 is then preferably updated to match the patient's organ structure (step 148).

Figure 2D:
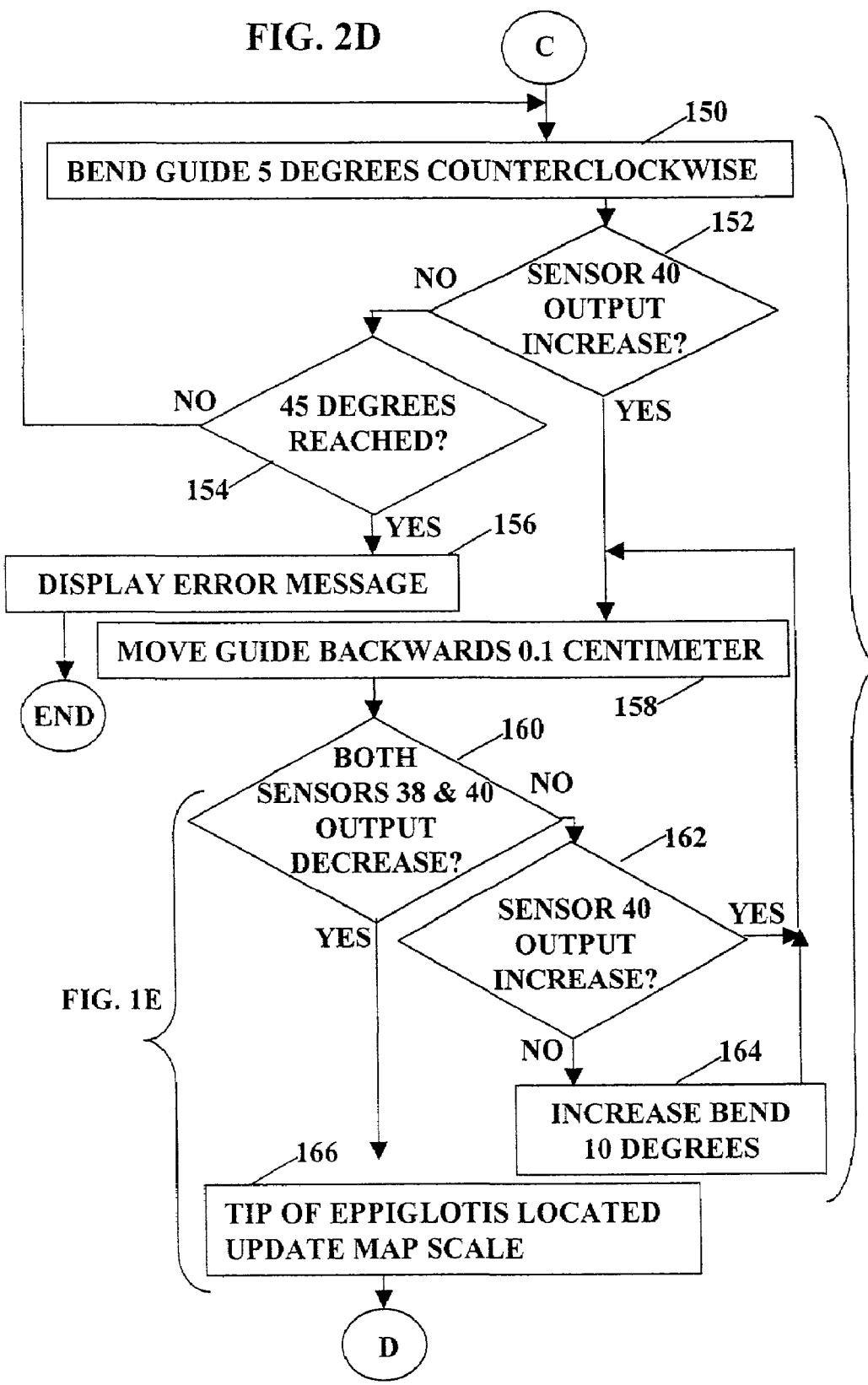

Reference is now made to FIG. 2D, which corresponds to FIGS. 1D and 1E. As seen in FIG. 2D the guide driver 15 performs steps 150, 152 and 154 in a loop, bending the distal end of the guide 20 counterclockwise until the tip 28 touches the epiglottis 48, or until a bending limit, preferably of 45 degrees is reached (step 154) and the intubation stops (step 156). The preferred point of engagement between the tip 28 and the surface of the epiglottis is designated in FIG. 1D by reference numeral 155. After sensing an engagement between the tip 28 and the surface of the epiglottis, the guide driver 15 performs steps 158, 160, 162, and 164 in a loop, retracting the guide 20 further (step 158), and increasing the bending of the guide 20 (step 164), until the tip of the guide reaches the tip of the epiglottis 48, designated in FIG. 1E by reference numeral 165. When the tip 28 reaches the tip of the epiglottis 48, the tip 28 is released and the output electric currents from both Hall effect sensors decrease to a minimum. Preferably the intubation pattern map 10 is updated (step 166) to match the patient's organ structure.

Reference is now made to FIG. 2E, which corresponds to FIGS. 1E and 1F. As seen in FIG. 2E, the guide driver 15 causes the guide 20 to move above and around the tip of the epiglottis 48 by causing the guide 20 to bend counterclockwise, preferably by 45 degrees, then to move forward down the throat by 5 millimeters and then to bend clockwise, preferably by 10 degrees (Step 170). Then the guide driver 15 performs steps 172, 174 and 176 in a loop, bending and extending (step 174) until the tip 28 of the guide touches the upper surface of the epiglottis 48 or until an extension limit, preferably of 1 centimeter, or a bending limit, preferably of 50 degrees, is reached, and the intubation is stopped (step 178). A preferred point of engagement between the tip 28 and the epiglottis is designated in FIG. 1F by reference numeral 177.

Figure 2F:
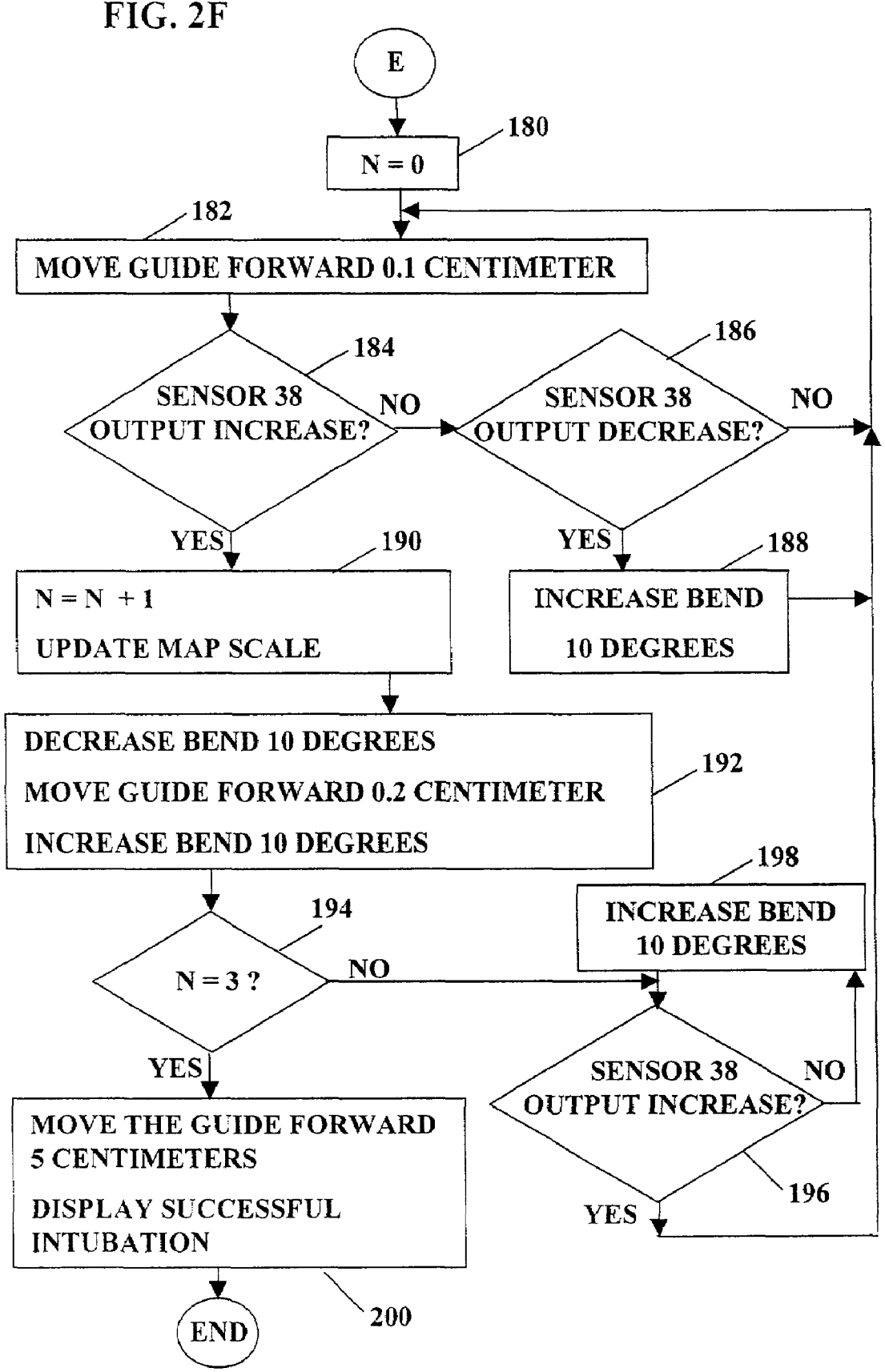

Reference is now made to FIG. 2F, which corresponds to FIGS. 1G to 1K. As seen in FIG. 2F, a "cartilage crest counter N" is first zeroed (step 180). Then the guide driver 15, performing steps 182 to 198 in a loop, causes the guide 20 to move the sensor tip 11 forward (step 182) along the surface of the trachea 44, preserving contact between the tip 28 and the surface of the trachea (steps 186 and 188) by increasing the bend (step 188) as needed. Each time a crest (189 in FIGS. 1H, 1I, 1J) of a cartilage of the trachea 44 is located the "cartilage crest counter" is incremented (step 190), the tip 28 is moved about the crest (steps 192, 194, 196 and 198) and the loop process repeats until the third cartilage is located. Then the guide 20 further extends, typically for adults by 5 centimeters, to ensure that the tube 16 reaches to the third cartilage. The guide driver 15 then signals to the operator that the insertion is completed successfully (step 200).

Figure 3:
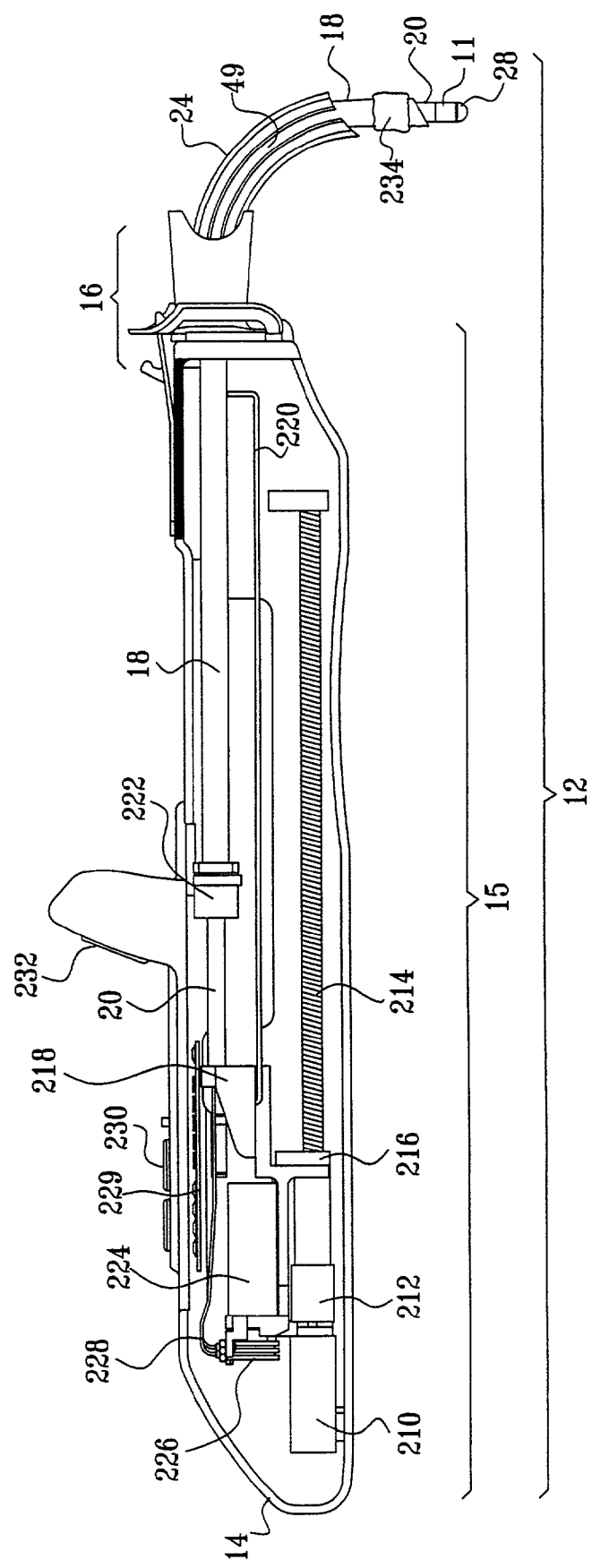
FIG. 3 is a simplified illustration of the internal structure of a preferred embodiment of the present invention for intubation of a human.

Reference is now made to FIG. 3, which is a simplified illustration of the internal structure of a preferred embodiment of the present invention useful for intubation of a human. The intubator assembly 12 preferably comprises the housing 14, the guide driver 15, the mouthpiece 16, the tube 18, the flexible guide 20 inserted inside the tube 18 and the tip sensor 11 mounted at the distal end of the guide 20. Preferably the mouthpiece comprises a curved pipe 24.

Preferably, the guide driver 15 comprises a first motor 210 that drives a gearbox 212 that rotates a threaded rod 214. A floating nut 216 is mounted on the threaded rod 214. As the motor 210 rotates the threaded rod 214, the floating nut 216 is moved forward or backward according to the direction of the rotation. The floating nut 216 is operative to move a carriage 218 along a bar 220 and thus to push or pull the guide 20. When the carriage 218 touches a stopper 222 the stopper 222 moves with the carriage 218 along the bar 220 and pushes the tube 18 forward.

A second motor 224 is connected to a disk 226 to which two guide angulation wires 228 are attached at first end thereof. The guide angulation wires 228 are threaded inside the guide 20 and their other ends are connected to the distal end of the guide just short of the tip sensor 11. When the motor 224 rotates the disk 226 clockwise one of the wires 228 is pulled and the second wire is loosened. The wire that is pulled pulls and bends the distal end of the guide 20 counterclockwise in the sense of FIG. 3. Accordingly, when the motor 224 rotates counter-clockwise the second wire of the two wires 228 is pulled and the first wire is loosened. The wire that is pulled pulls and bends the distal end of the guide 20 clockwise in the sense of FIG. 3.

Electronic circuitry 229 is provided within the housing 14 and is preferably electrically connected to operating switches 230, a display 232, the motors 210 and 224 and to the Hall effect sensors 38 and 40 (FIG. 1A) in the tip sensor 11. Preferably, the electronic circuitry 229 also comprises a microprocessor, operative to execute a program. The program is preferably adapted to control the switches 230, the display 232, motors 210 and 224 and the Hall effect sensors 38 and 40 and to insert and bend the guide inside a living organism, according to a predefined map until the tip of the guide reaches a destination point inside the living organism. Preferably the program is operative to cause the tip 28 of the guide 20 to follow a predefined internal contour of an organ of the living organism. Preferably program is operative employ tactile sensing to measure the position of the tip of the guide relative to the surface organ of the living organism.

It is appreciated that the term "microprocessor" also includes inter alia a "microcontroller".

Electrical batteries (not shown) are preferably provided within the housing 14 to supply electric power to the electronic circuitry, the tip sensor 11, the motors 210 and 224, the display 232 and all other elements of the present invention that consume electricity. It is appreciated that external sources of electricity can also be employed to provide power to the intubator assembly 12.

Communication interface (not shown), preferably employing infra-red communication technology, is provided to enable communication with external data processing equipment.

Preferably, a balloon 234 is provided at the distal end of the tube 18 and a thin pipe (not shown) is inserted through the pipe 18 and is connected, through the side of the pipe, to the balloon. The thin pipe enables an operator to inflate the balloon when the distal end of the pipe 18 reaches the appropriate place in the trachea, thus securing the distal end of the pipe to the trachea.

Figure 4:
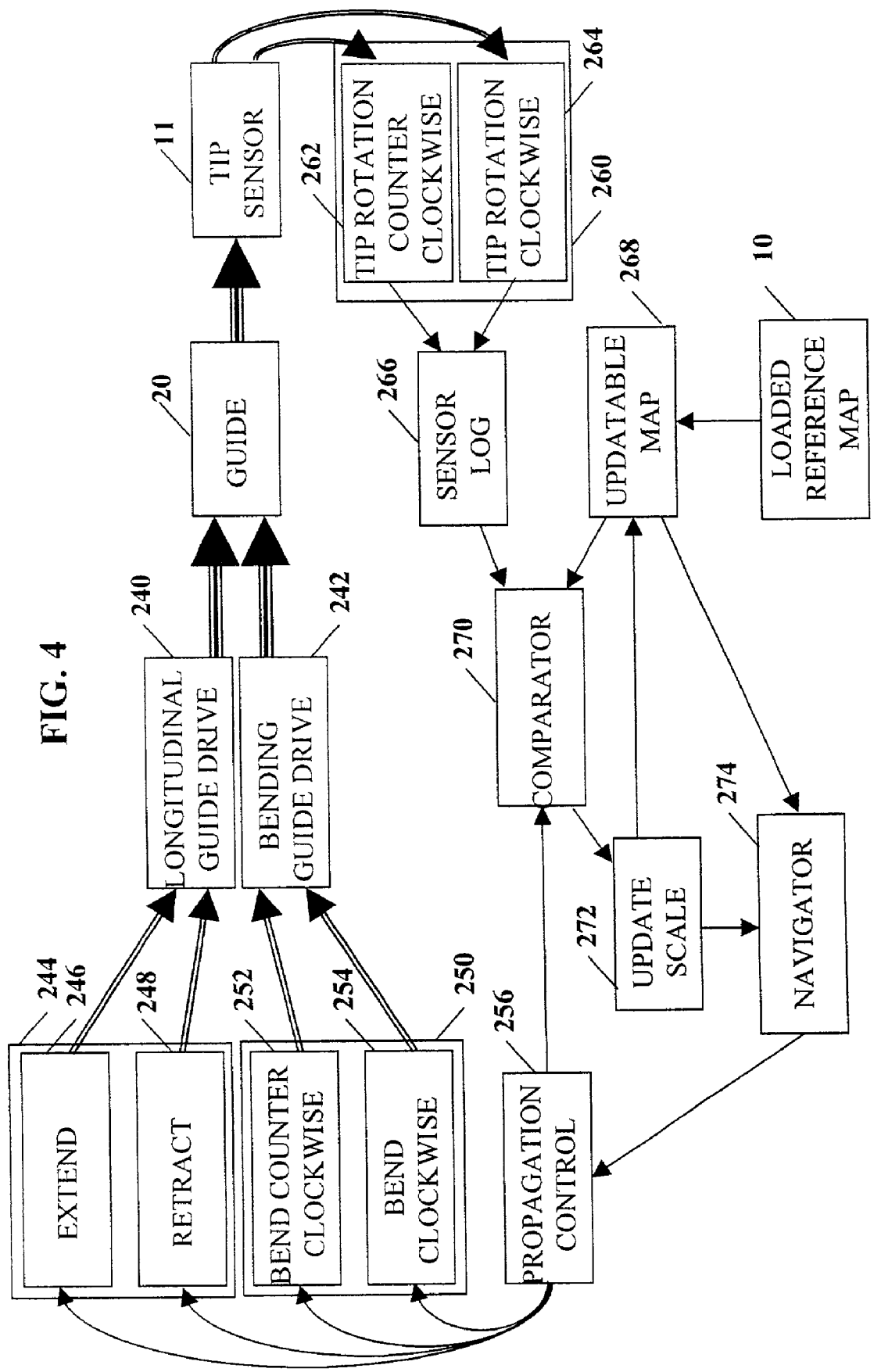
FIG. 4 is a simplified block diagram of a preferred embodiment of the present invention.

Reference is now made to FIG. 4, which is a simplified functional block diagram of a preferred embodiment of the guide driver 15 described hereinabove. In FIG. 4 the guide 20 is driven by two drivers. A longitudinal driver 240 preferably comprises a motor 210, the gear 212, the threaded rod 214, the floating nut 146 and the carriage 218 of FIG. 3. A bending guide driver 242 preferably comprises the motor 224, the disk 226 and wires 228 ((FIG. 3). The longitudinal driver 240 and the bending guide driver 242 are controlled by two software driver modules. A longitudinal software driver module 244 controls the longitudinal driver 240 and comprises two functions: an extend function 246 and a retract function 248. A bending software driver 250 controls the bending guide driver 242 and comprises two functions: a bend counterclockwise function 252 and a bend clockwise function 254. The functions 246, 248, 252 and 254 are operated by a propagation control software module 256.

At the other end of the guide 20, the tip sensor 11 measures the proximity and orientation of an adjacent surface. In a preferred embodiment of the present invention the tip sensor 11 performs the proximity and orientation measurements by measuring the force applied to a tactile tip by a surface of an adjacent tissue. A tip sensor software driver module 260, operative to receive input signals from the tip sensor 11, provides two input functions: a counterclockwise tip rotation function 262 and a clockwise tip rotation function 264. The measurements of the tip positions as provided by the tip sensor software driver module 260 are collected and stored by a sensor log module 266.

The map 10 is loaded into memory and serves as an updatable map 268. A comparator 270 compares the accumulated measurements from the tip sensor 11 with the updated reference map 268. The results of the comparisons are calculated by an update scale module 272 to provide a scaling factor that is applied to update the updated map 268. Consequently a navigation module 274 employs the updated map information to instruct the propagation control 256 to execute the next step of the insertion program.

It is appreciated that a measurement of the electric current drawn by at least one of the longitudinal guide drive and the bending guide drive can also serve as an input to the comparator 270 to evaluate the position of the tip sensor.

Reference is now made to FIGS. 5A to 5H, which are, taken together, an electrical schematic of a preferred embodiment of the present invention useful for intubation of a human. Reference is especially made to microprocessor 278, which is preferably operative to operate a program to control the elements of the intubator assembly 12, such as the operating switches 230, the display 232, the motors 210 and 224 (FIG. 3), and the Hall effect sensors 38 and 40 in the tip sensor 11 (FIG. 1A), and to perform the intubation process, such as the process shown and described hereinabove with reference to FIGS. 2A to 2F.

Reference is now made to FIGS. 6A to 6K, which are a series of simplified pictorial illustrations of ten typical steps in a process of employing a preferred embodiment of the present invention useful for insertion of an element into the intestine of a human.

It is appreciated that some of the organ systems of a living organism are generally similar up to a scale factor, such as the mouth and trachea system. Other organs, such as the intestine system, are generally different from one human body to the other. Therefore, in order to employ the present invention to insert a medical device or apply a medicine to a specific location within a generally variable organ, a map of the organ, at least from the entry point and until the required location, is prepared before the insertion process is activated. The required map is preferably prepared by employing an appropriate medical imaging system, such as an ultrasound scanner, an x-ray imager, a CAT scan system or a MRI system. The map can be a two dimensional map or a three-dimensional map as appropriate for the specific organ. Typically for the intestine system a three dimensional map is required.

It is appreciated that an inserter according to a preferred embodiment of the present invention for use in organs that are variable in three dimensions is similar to the intubator assembly 12, preferably with the following modifications:

(1) The tube 18 may be replaced with a different insertable device;

(2) An additional guide bending system employing elements similar to motor 222, disk 224 and wires 226 is added and mounted perpendicularly to the first system of motor 222, disk 224 and wires 26, so that it is possible to bend the end of the guide in three dimensions. It is appreciated that three-dimensional manipulation is possible also by employing three or more motors; and (3) The tip sensor 11 preferably comprises four Hall effect sensors to sense the motion of the tip 28 in three dimensions. It is appreciated that it is possible to operate the tip sensor in a three-dimensional space also by employing three Hall effect sensors. It is also appreciated that other types of sensors can be employed to measure the proximity and orientation of an adjacent surface in three dimensions.

In a preferred embodiment of the present invention, when the guide 20 performs longitudinal motion, such as insertion or retraction, the guide 20 also performs a small and relatively fast lateral motion. The combined longitudinal and lateral motions are useful for sensing the surface of the organ in three dimensions and hence to better determine the location of the tip sensor 11 in the organ and relative to the map 10.

Due to limitations of the graphical representation, a two-dimensional imaging and map is shown in FIGS. 6A to 6K.

Figure 6A:
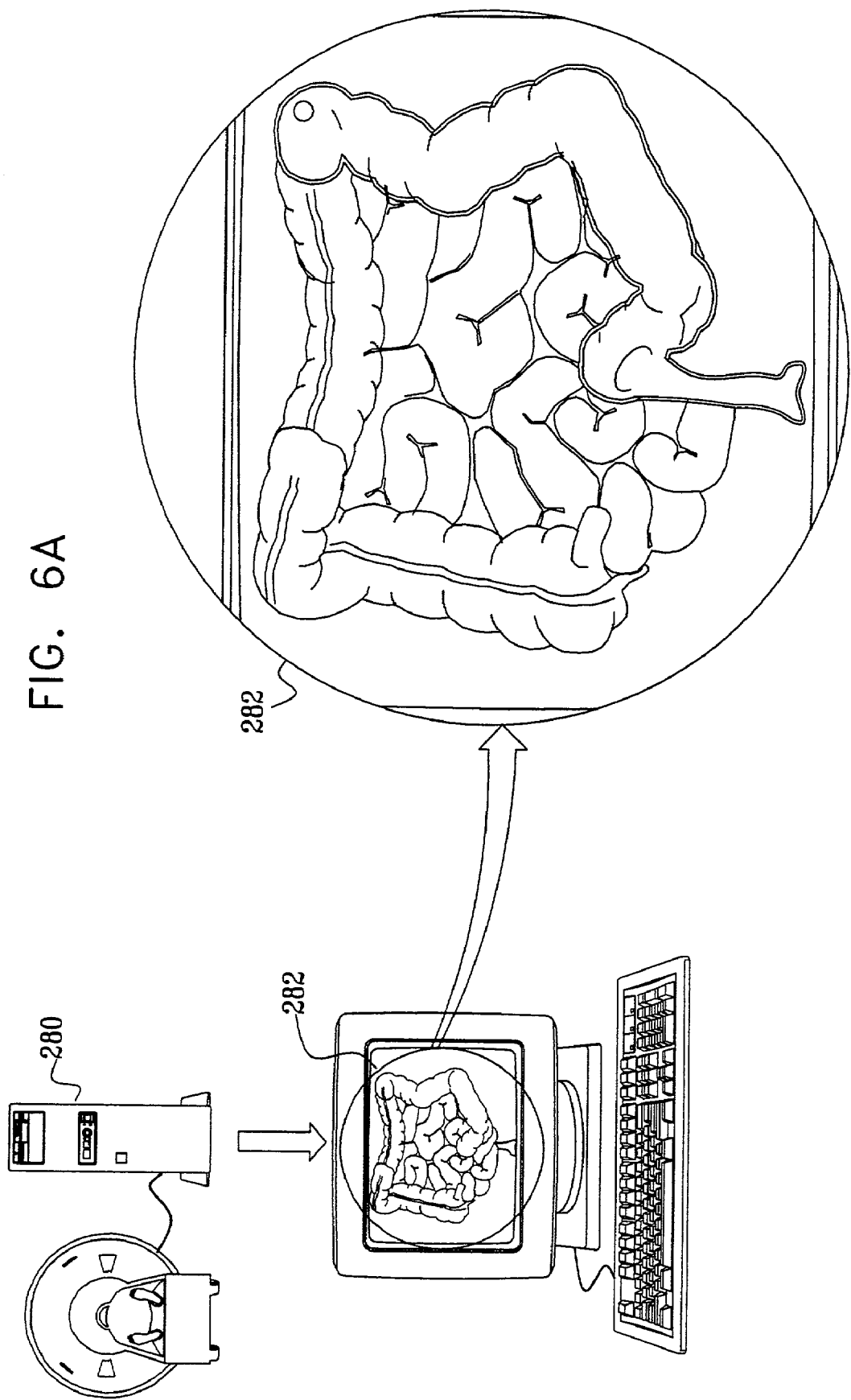

As seen in FIG. 6A, a human organ, the intestine in this example, is imaged, typically by a CAT scan system 280, and an image 282 of the internal structure of the organ is produced.

In FIG. 6B the image 282 of the organ is used to create an insertion map 284. Typically the image 282 is displayed on a computer screen (not shown) and a pointing device, such as a computer mouse or a light pen, is used to draw a preferred path 286 that the tip of the guide is to follow. The path is typically drawn by marking a contour of the organ, and optionally marking the guide bending points, as is shown and described with reference to FIGS. 1A to 1K. Alternatively, a preferred path is created, such as path 286, not necessarily continuously following the contours of the organ. As a further alternative, the map 10 or the path 286 is converted into a set of insertion steps as is shown and described hereinbelow with reference to FIG. 7.

Reference is now made to FIG. 7 together with FIG. 8 and with FIGS. 6C to 6K. As shown in FIG. 7, a table 290 is provided for storage in a computer memory and for processing by a computer processor. The table 290 contains rows 292, wherein each row 292, preferably comprises an instruction to perform one step in the process of insertion of a medical insertion device into a living organism such as shown and described with reference to FIGS. 6C to 6K. Preferably each row 292 contains the expected values or the maximal values for the extension of an insertion guide such as guide 20, the bending of the insertion guide and the electrical outputs from the Hall effect sensors 38 and 40 (FIG. 1A). In a preferred embodiment of the present invention the row 292 contains five sets of values:

(a) Initial bend 294 contains two values for bending the guide from a straight position, in two perpendicular planes.

(b) Initial insertion 295 contains a longitudinal value for extending or retracting the guide in centimeters.

(c) Initial sensor measurements 296 contains expected output values of four sensors such as four Hall effect sensors, for example, Hall effect sensors 38 and 40 of FIG. 1A. The initial sensors measurements 296 are expected to be measured by the time the guide reaches the value of the initial insertion 295.

(d) Insert distance 297 contains a longitudinal value for further extending or retracting the guide in centimeters. Typically the initial sensor measurements 296 are expected to be preserved, while the guide is extended or retracted, by adapting the bending of the guide.

(e) Final sensor measurements 298 contain expected output values of the four sensors of step (c). The initial sensor measurements 298 are expected to be measured by the time the guide reaches the value of the insert distance 297.

It is appreciated that the path drawn in FIG. 6B can be employed to prepare a table of instructions such as table 290 of FIG. 7.

Referring to FIG. 8, which is a flowchart illustrating a preferred implementation of the present invention, operative for a process of insertion of an element into the intestine of a human as shown in FIGS. 6A to 6K. The flowchart of FIG. 8 is a preferred embodiment of a program, operative to be executed by a processor, such as microprocessor 278 of FIG. 5A, comprised in a preferred embodiment of the present invention, for insertion of an element into a living organism, preferably by employing a table 290 shown and described with reference to FIG. 7.

The preferred flowchart shown in FIG. 8 starts by loading the table (step 300) such as the map shown in FIG. 7. The program then reads a first row 292 from the map (step 302) and causes the distal end of the guide 20 to bend according to the initial bending values 294. Then the program causes the guide 20 to extend or retract according to the initial insertion distance 295 of the first row in the map. The program continues to bend and insert the guide 20 until output values of the sensors match the expected initial sensor measurement 296 of the row (steps 304, 306 and 308), or until a limit is surpassed, an error message is displayed and the program is stopped (step 310).

Preferably, the initial values of the sensors are measured and then the program continues to extend or retract the guide 20 (step 312) until the sensors produce the final sensors measurements 298 values (step 314), while keeping in contact with the surface (steps 316 and 318) or until at least one of predefined limits is surpassed (step 320) where the program is stopped (step 310). If the final sensor measurements 298 values are measured the program proceeds to step 320 and loops through steps 302 and 320 until all the rows 292 of the table are processed. Then the program displays an insertion success message on the display 232 and halts (step 322).

As indicated by row No. 1 of FIG. 7 and FIG. 6C the guide is bent, preferably by up to 45 degrees, to the left in the plane of FIG. 6C and, while preserving contact with the left side of the intestine, is extended up to 5 centimeters or until the sensor tip engages the internal surface of the intestine head on at a point in the map 284 designated by reference numeral 330.

As indicated by row No.2 of FIG. 7 and FIG. 6D the guide is bent by up to 45 degrees to the right in the plane of FIG. 6D and, while preserving contact with the left side of the intestine, is extended up to 2.5 centimeters or until the sensor tip does not sense the internal surface of the intestine at a point in the map 284 designated by reference numeral 332.

As indicated by row No. 3 of FIG. 7 and FIG. 6E the guide is bent by up to 110 degrees to the left in the plane of FIG. 6E and, while preserving contact with the left side of the intestine, is extended by 1 centimeter to a point in the map 284 designated by reference numeral 334.

In accordance with row 4 of FIG. 7 and FIG. 6F the guide is bent by up to 45 degrees to the right in the plane of FIG. 6F and is extended by 6 centimeter to a point in the map 284 designated by reference numeral 336.

Figure 5A:
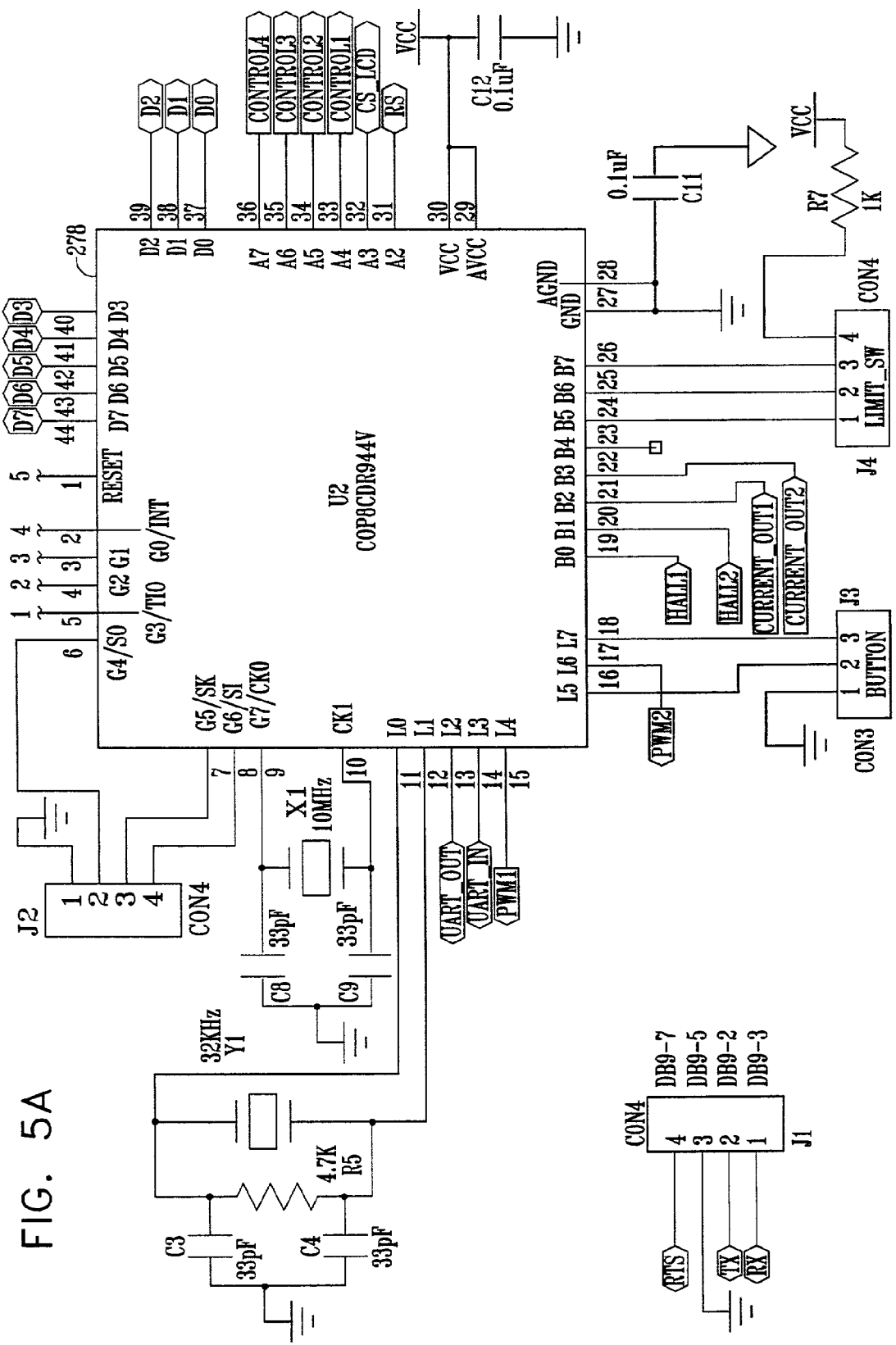
FIGS. 5A to 5H are electrical schematics of a preferred embodiment of the present invention for intubation of a human.
Figure 5B:
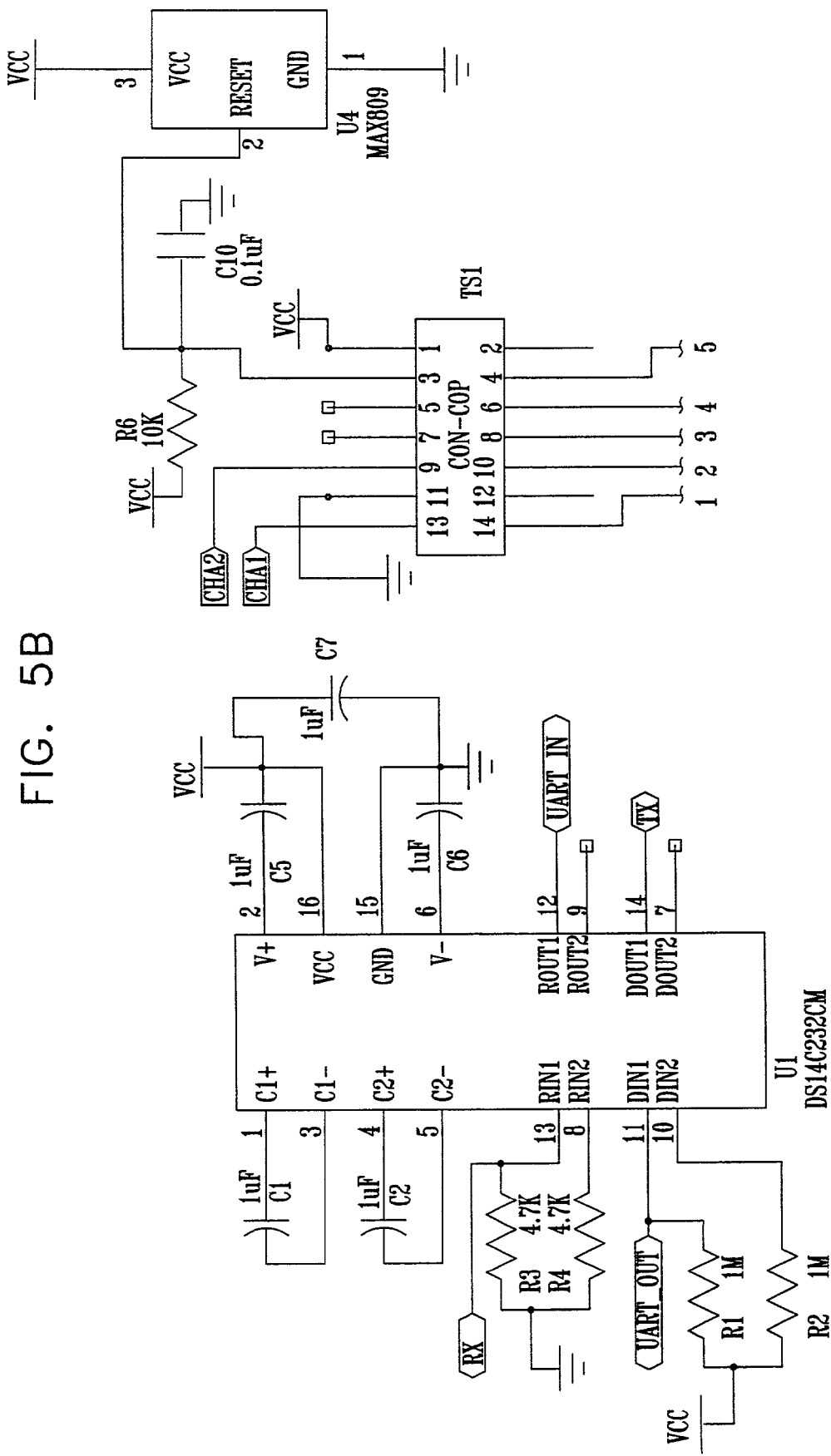
Figure 5C:
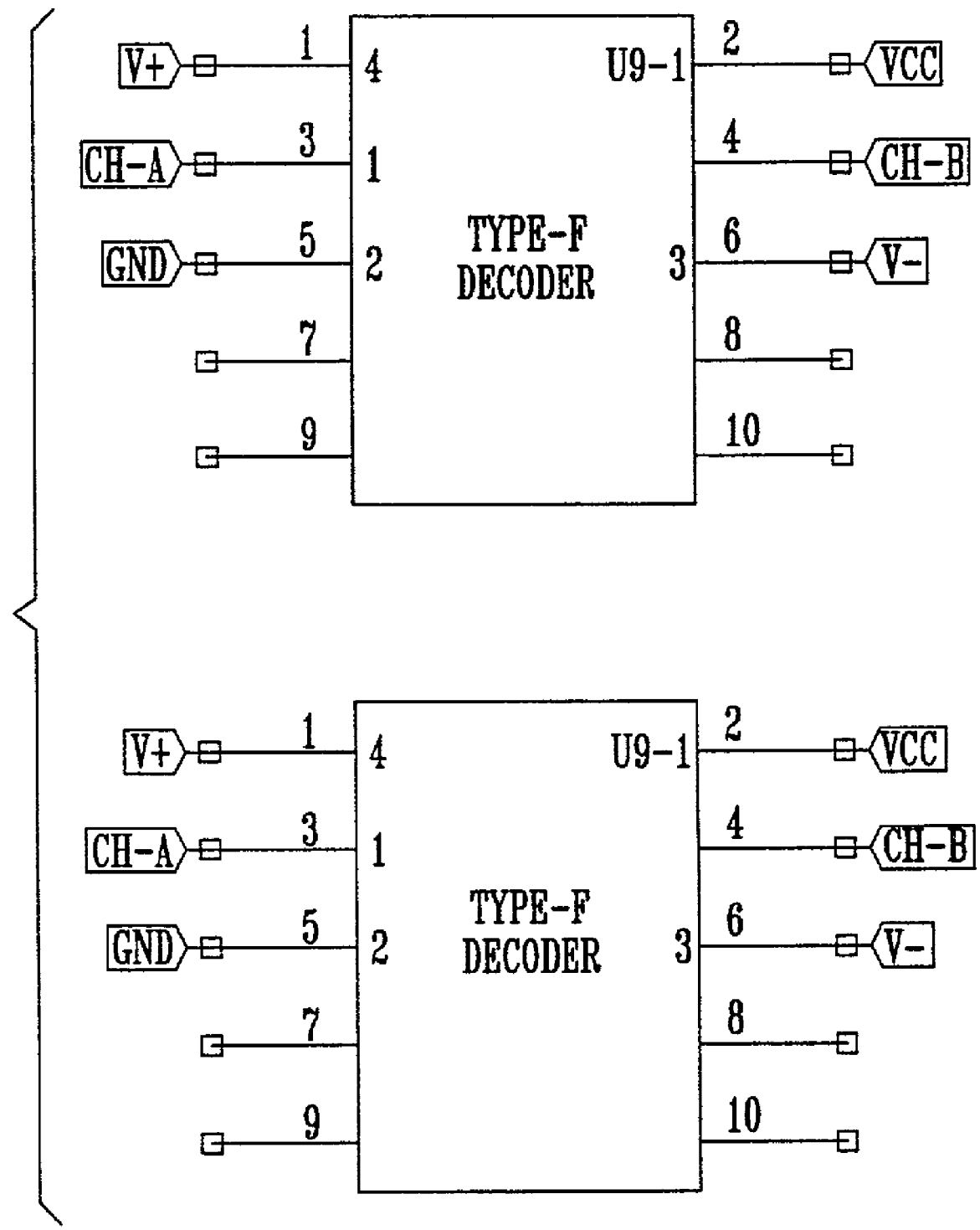
Figure 5D:
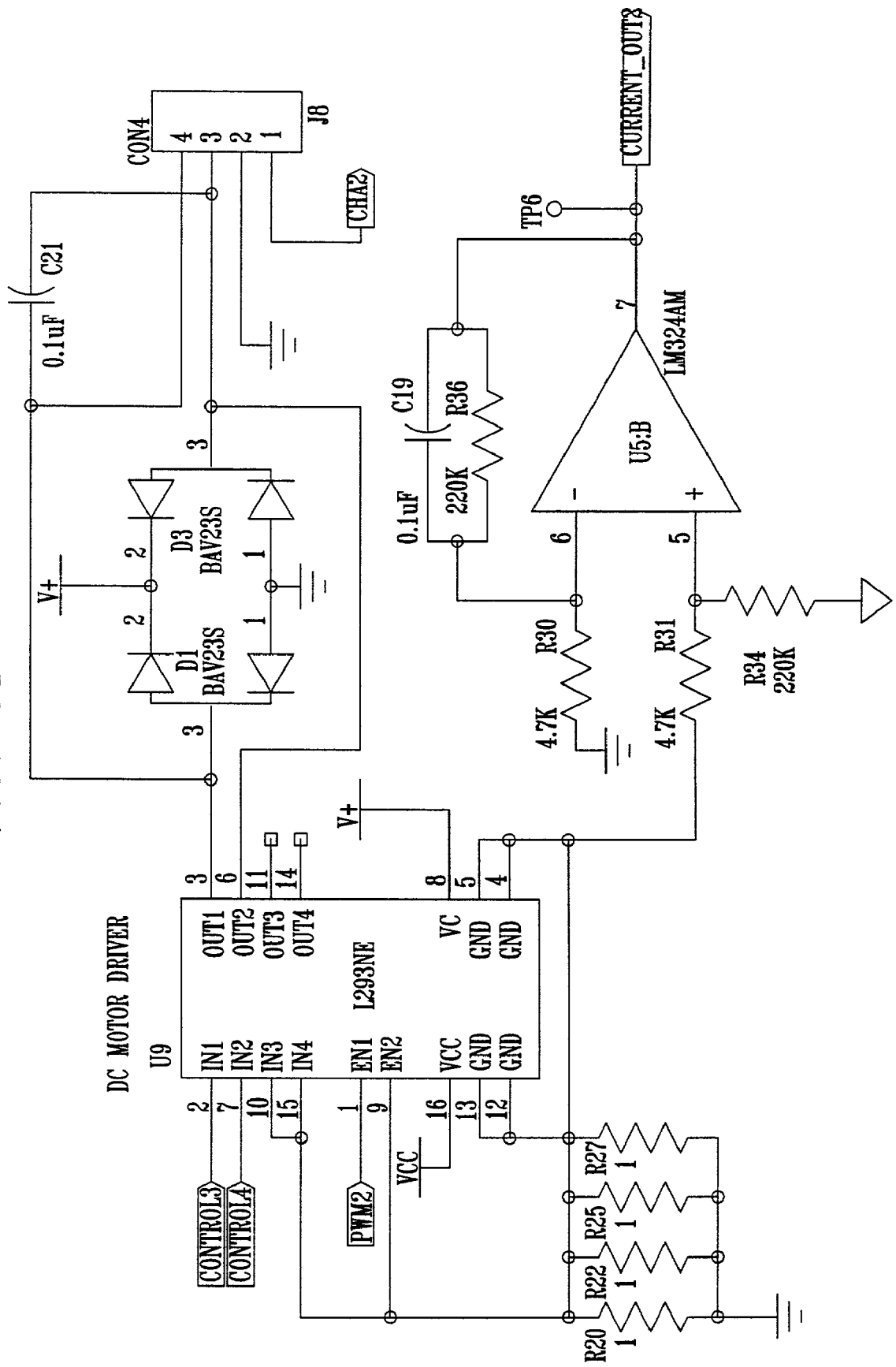
Figure 5E:
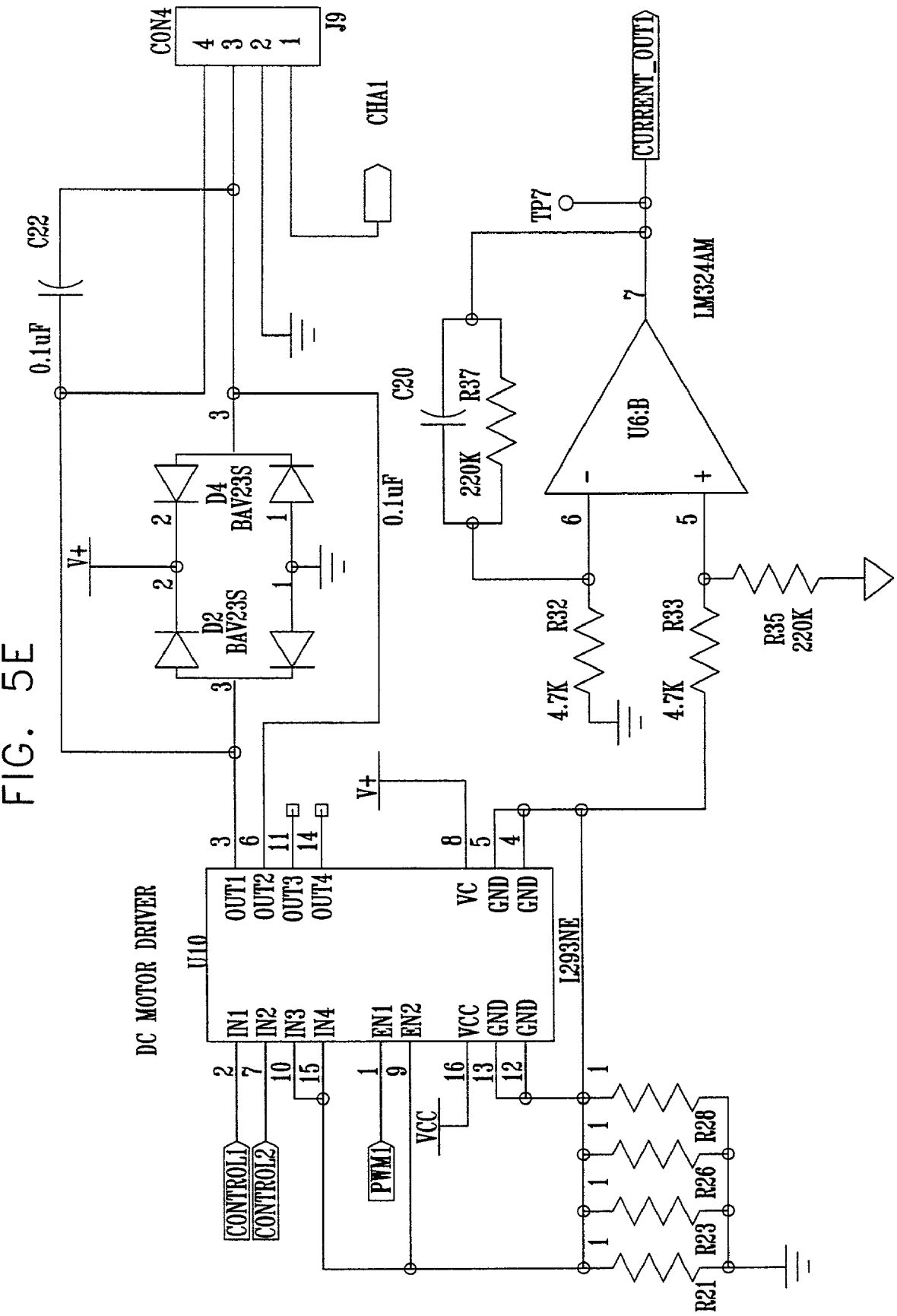
Figure 5F:
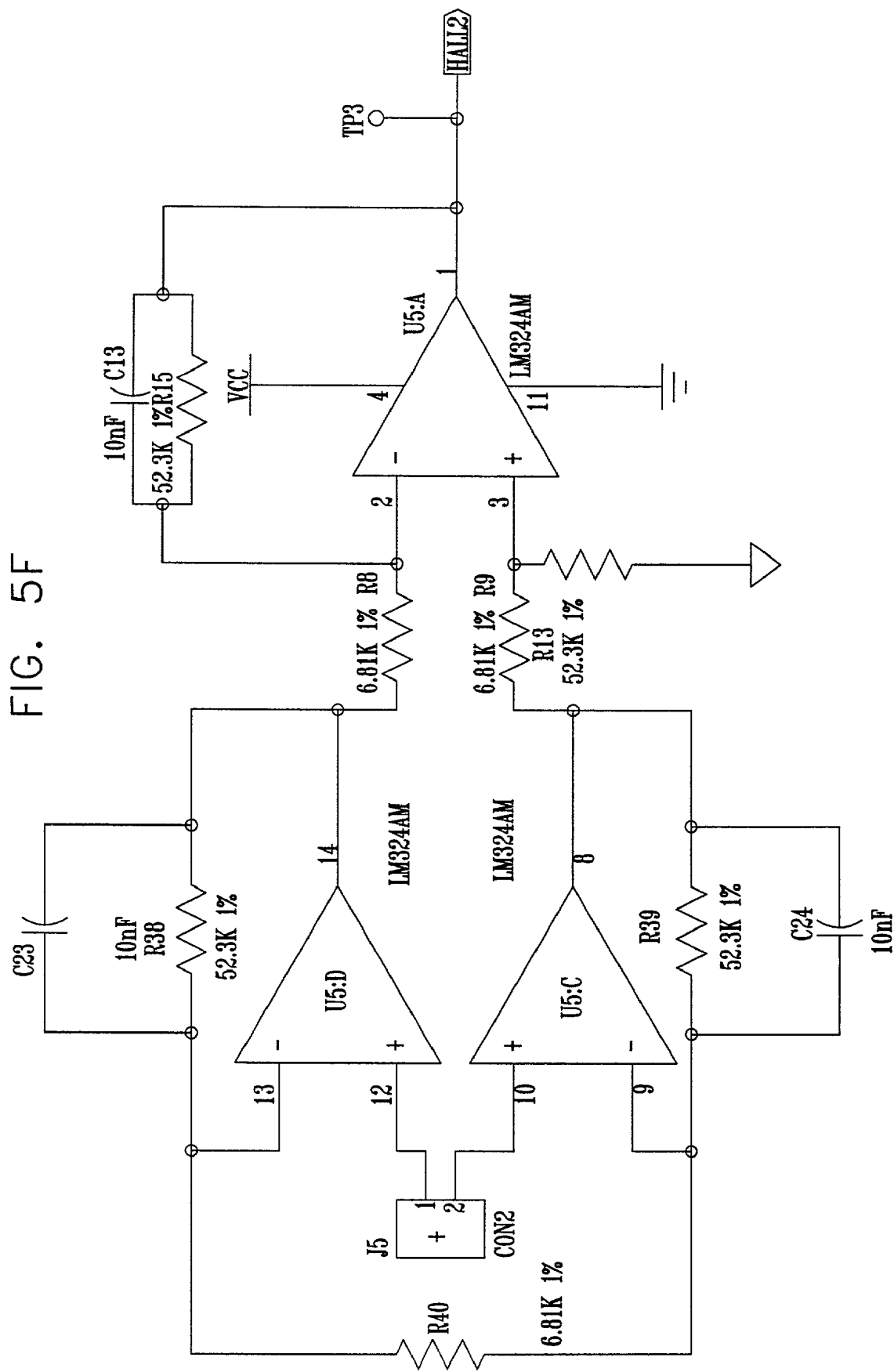
Figure 5G:
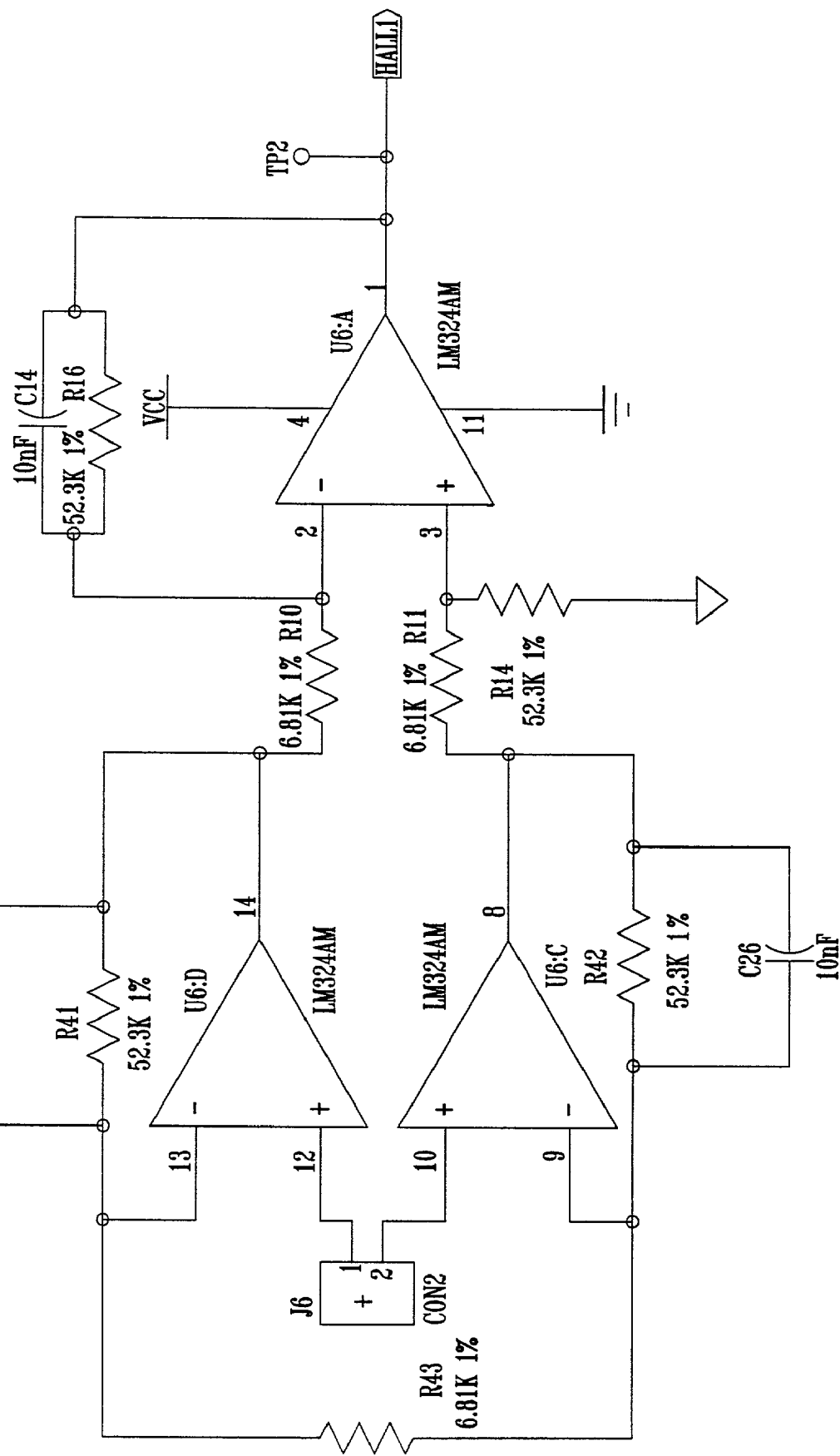
Figure 5H:
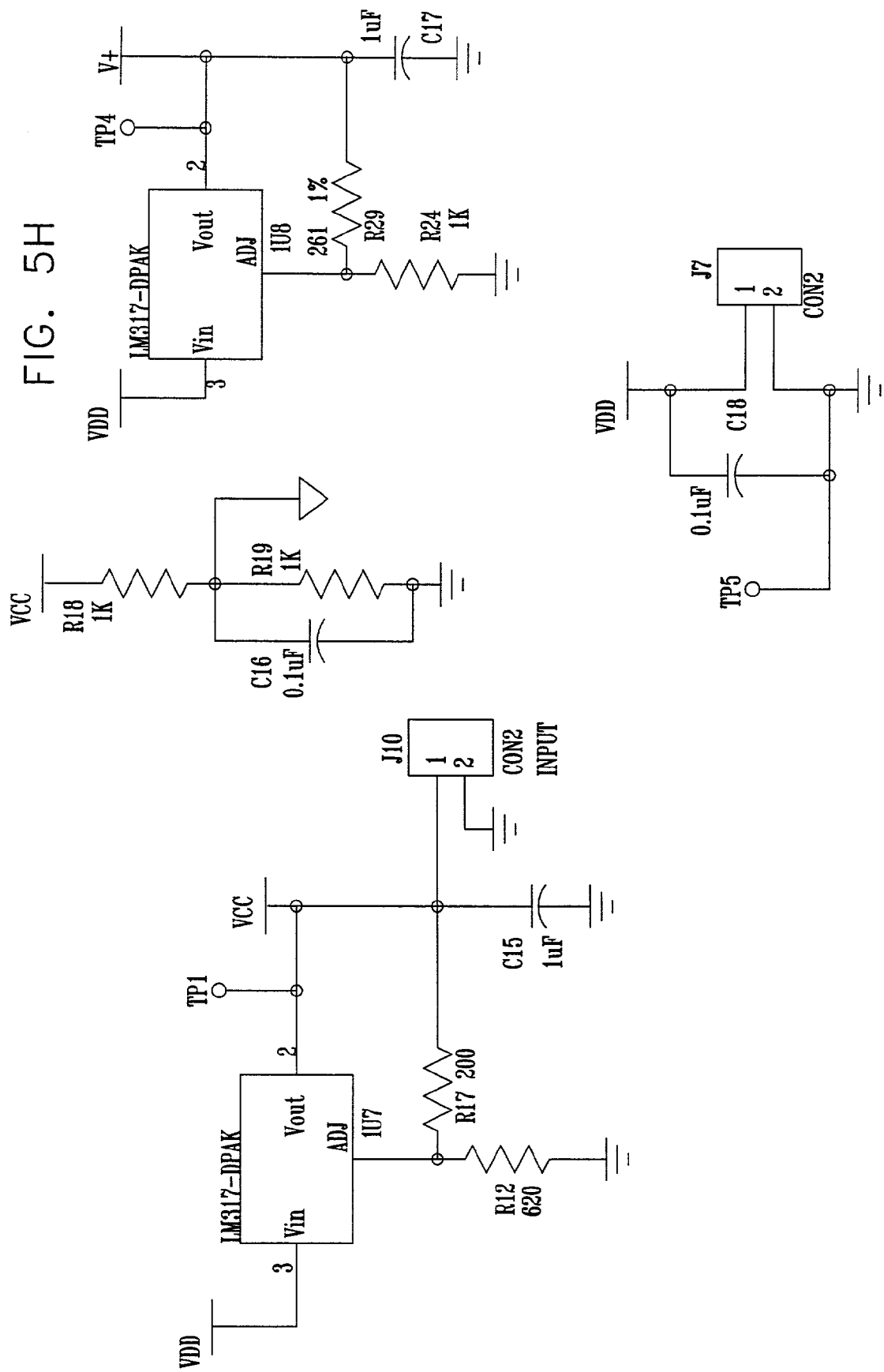

As indicated by row No. 5 of FIG. 7 and FIG. 6G the guide is bent by up to 20 degrees to the right in the plane of FIG. 5G and, while preserving contact with the right side of the intestine, is extended by 4 centimeters to a point in the map 284 designated by reference numeral 338.

As indicated by row No. 6 of FIG. 7 and FIG. 6H the guide is bent by up to 60 degrees to the left in the plane of FIG. 6H and is extended by up to 3 centimeters or until the sensor tip engages the internal surface of the intestine head on at a point in the map 284 designated by reference numeral 340.

As indicated by row No. 7 of FIG. 7 and FIG. 6I the guide is bent by up to 45 degrees to the right in the plane of FIG. 6I and is extended by up to 1 centimeter or until the sensor tip engages the internal surface of the intestine with its right side in a point in the map 284 designated by reference numeral 342.

As indicated by row No. 8 of FIG. 7 and FIG. 6J the guide is extended by up to 1 centimeters or until the sensor tip engages the internal surface of the intestine with its left side at a point in the map 284 designated by reference numeral 344.

As indicated by row No. 9 of FIG. 7 and FIG. 6K the guide is bent by up to 45 degrees to the right in the plane of FIG. 6K and is extended by up to 1 centimeter or until the sensor tip engages the internal surface of the intestine head on at a point in the map 284 designated by reference numeral 346.

In a preferred embodiment of the present invention the system and the method are operative for automatic operation. Alternatively the present invention can be operated manually, by providing to the operator the information collected by the sensor log 266 form the tip sensor 11 and enabling the operator to control manually the guide 20. In another alternative part of the procedure is performed automatically and another part is performed manually. For example, the guide 20 may be inserted automatically and a medical device, such as the tube 18 may be inserted manually.

It is appreciated that a log of the process of insertion of an insertable element into a living organism such as a human body is preferably stored in an internal memory of the present invention and that this log can be transmitted to a host computer. It is appreciated that the host computer can aggregate insertion process logs and thereby continuously improve relevant insertion pattern maps such as the standard contour map 10. Thereafter, from time to time or before starting an insertion process, the present invention is capable of loading an updated map such as standard contour map 10.

It is also appreciated that the accumulated logs of processes of insertions cab be employed to improve the algorithm for processing the maps, such as the algorithms shown and described with reference to FIGS. 2A–2F and FIG. 8. The improved algorithm can be transmitted to the present invention as necessary.

Appendices 1 to 3 are software listings of the following computer files:

Appendix 1: containing file intumed.asm.

Appendix 2: containing file c8cdr.inc.

Appendix 3: containing file ram.inc.

The method for providing the software functionality of the microprocessor 278, in accordance with a preferred embodiment of the present invention includes, the following steps:

1. Provide an Intel compatible computer with a Pentium II CPU or higher, 128 MB RAM, a Super VGA monitor and an available serial port.
2. Install Microsoft Windows 95 or Microsoft Windows 98 Operating System.
3. Install the Testpoint Development kit version 40 available from Capital Equipment Corporation. 900 Middlesex Turnpike, Building 2, Billereca, Mass. 0821, USA.
4. Connect a flash processor loading device COP8EM Flash, COP8 In Circuit Emulator for Flash Based Families to the serial port of the Intel compatible computer. The COP8EM flash processor loading device is available from National Semiconductors Corp. 2900 Semiconductor Dr., P.O. Box 58090, Santa Clara, Calif. 95052-8090, USA
5. Place a COP8CDR9HVA8 microcontroller available from National Semiconductors Corp., 2900 Semiconductor Dr., P.O. Box 58090, Santa Clara, Calif. 95052-8090, USA in the COP8EM Flash.
6. Copy the files intumed.asm, c8cdr.inc, and ram.inc, respectively labeled Appendix 1, Appendix 2 and Appendix 3 to a temporary directory.
7. Load the file intumed.asm by using the operating software available with the COP8EM Flash device from National Semiconductors.
8. To run the intumed.asm; Install the COP8CDR9HVA8 microcontroller in its socket in the electrical circuit, which detailed electronic schematics are provided in FIGS. 5A to 5H, where the microcontroller is designated by reference numeral 278.

It is appreciated that the software components of the present invention may, if desired, be implemented in ROM (read-only memory) form. The software components may, generally, be implemented in hardware, if desired, using conventional techniques.

It is appreciated that the particular embodiment implemented by the Appendix is intended only to provide an extremely detailed disclosure of the present invention and is not intended to be limiting.

It is appreciated that various features of the invention which are, for clarity, described in the contexts of separate embodiments may also be provided in combination in a single embodiment. Conversely, various features of the invention which are, for brevity, described in the context of a single embodiment may also be provided separately or in any suitable subcombination.

It will be appreciated by persons skilled in the art that the present invention is not limited by what has been particularly shown and described hereinabove. Rather the scope of the present invention includes both combinations and subcombinations of the various features described hereinabove as well as variations and modifications which would occur to persons skilled in the art upon reading the specification and which are not in the prior art.

Appendices 1 through 3 are as follows:

Appendix 1
; Files: intumed.asm, ram.inc and c8cdr.inc.

UPPERCASE
   ; verify
   .TITLE intumed
   .LIST 0ff  ;complete listing.  ; X'040
   .CONTRL 3   ; 0- disable all code alteration, 3- re-enable code alteration.

.incld c8cdr.inc  ; File that include all the definitions of cop8cdr.
   .incld ram.inc  ; File that include all the variables, constants, registers and
                  ; bits definitions.

;----------------CONFIGURATION---------------------
.sect option,conf

.db 01  ; 5=0 security dis, 2=0 wdog dis, 1=0 halt dis, 0=1 flex.
         ; flex=1 -execution following reset will be from flash memory.
         ; flex=0 -flash memory is erased. execution following reset will be from
         ;     boot rom with the mictowire plus isp routines.

;-------------------------------------------
.sect begin_rst,rom,abs=0
reset: rpnd ;------------ Clear memory -------------------
   ld s,#0   ; Clean segment0 0-6fH.
   ld b,#0   ;
   ld a,#06f   ; Cleans the memory between
st00: ld [b+],#0  ; b to a
   ifgt a,b  ;
   jmp st00  ;

LD SP,#01e  ; Stack Pointer in Memory 1eH. The stack works in LIFO (last
   ld 01e,#0ff ; in first out) with "push a" and "pop a" instructions.
   ld 01f,#0ff ; The stack starts from 1eH until 0H.

ld s,#1   ; Clean s1 0-7fH.
   ld b,#0   ;
   ld a,#07f   ; Cleans the memory between
st01: ld [b+],#0  : b to a
   ifgt a,b  :

24

```
        jmp st01    ;

ld s,#2       ; Clean s2 0-7fh.
        ld b,#0       ;
        ld a,#07f     ; Cleans the memory between
st02:   ld [b+],#0    ; b to a
        ifgt a,b      ;
        jmp st02      ;

ld 05c,#'E'   ; when the pc send moving command, the cop8 transmit packets of ld 05d,#'D'   ; information every 160 msec. in every packet We have 10 blockes of
                      ; 9 bytes in s1 and 10 in s2. At the end of the packet there is 1
                      ; byte of check sum and then the 2 bytes of 'E','D' to signal
                      ; end of transmition.
        ld s,#0
; --- port  definitions ---    see ram.inc for bits definitions.
        ld pgc,#033; clkdly enabled   ; g2=t1b=cha2,g3=t1a=cha1 - inputs
        ld pg,#0     ; sk idle phase=0
        ld plc,#057
        ld pl,#0af
        ld pbc,#010; b0-3 = a2d(in), b5-7 = limit switches(in)
        ld pb,#0f0
        ld pac,#0ff
        ld pa,#03

; ----- UART initialization -------------
        ld enu,#0       ; no parity, 8 bit data
        ld enur,#0
        ld enui,#022    ; 1 stop bit, Asynch. mode,psr+baud clock
                        ; enable receive int.,disable trans. int.
        ld baud,#4      ; 38400 baud rate.
        ld psr,#060     ; 10MHz*2 /(16*(4+1)*6.5)

; ----- LCD initialization -------------
        jsr init_lcd
        ld temp,#low(wordmm); type in line 1 of lcd "  mm  ", in the left side there is
        jsr type_string0   ; space for 3 digits of mm, and in the right side 3 spaces for
                           ; direction (+/- up/down) and 2 digits of movement.
        ld temp,#low(wordpoweron)
        jsr type_string1

; ----- PWM.T0.interupts initialization -----------
```

```
        ld cntrl,#080      ; timer 1 - pwm mode - stopped.
        ld a,#0ff          ; timer 1 would be used in capture mode, meaning that pulse
        x a,tmr1lo         ; received from linear motor will capture the value of timer1
        ld a,#0ff          ; in timer 1 auto reload A (t1rahi/lo) and pulse from angular
        x a,tmr1hi         ; motor in B (t1rbhi/lo).

ld t2cntrl,#0a0;   timer 2 - pwm toggle mode stopped.
        ld t3cntrl,#0a0;   timer 3 - pwm toggle mode stopped.
        sbit t2a,p1        ; enable linear motor and lock it by putting 0 in control1,2.
        sbit t3a,p1        ; enable angular motor and lock it by putting 0 in control3,4.

sbit t2hs,hstcr
        sbit t3hs,hstcr
        ld cntrl,#060      ; timer 1 - capture mode.

rbit t1pndb,icntrl
        sbit t1enb,icntrl  ; timer 1 - capture mode, t2enB=1
        rbit t1pnda,psw
        sbit t1ena,psw     ; timer 1 - capture mode, t2enA=1
        sbit itsel0,itmr;  8,192 inst. cycles - 4,096 m. sec timer 0 interrupts.
        rbit t0pnd,icntrl
        sbit t0en,icntrl;  start timer0.

; ----- Program initialization ----------- sbit 7,pls_y1      : pls_y=08000H
                           ; over 80 is positive angle and under 80 is negative angel.
        ld data_cntr,#21
        sbit stop2,aflags
    ;   sbit direction,lflags
        sbit stop1,lflags
        sbit en_calc,lflags
        ld pls_x1,#068
        sbit limits_c_en,limits_flags
        sbit home_command,buttons_flags
        sbit gie,psw       ; enable interupts.
        jmp main ;************************************************
        .sect pc_module.rom
main:   ifbit limits_c_en,limits_flags
        jsr limits_check ifbit start_stop,buttons_flags
        jsr autorun_states
```

```
         ifbit stop_command,buttons_flags
         jsr stop_operation 5       ifbit buttons_t_en,buttons_flags
         jsr buttons_test ifbit home_command,buttons_flags
         jsr home_p_states
10       ifbit self_t_command,buttons_flags
         jmp self_t_states main0: jmp linear_states     ; linear_states + angular_states.

15 main1: jsr updatelcd ifbit a2den,flags2     ; a2d check.
         jsr a2d00

20       ld a,#0
         add a,linear_stat
         add a,ang_stat
         add a,autorun_stat
         add a,selft_stat
25       add a,home_stat
         ifeq a,#0
         sbit enddata,flags1    ; if 2 motors are stopped, set enddata bit to stop transmitting
   to PC.
         ld a,buttons_flags
30       and a,#09e             ; if one of the commands flags is set, reset enddata bit.
         ifgt a,#0
         rbit enddata,flags1
         ifbit enddata,flags1
         rbit start,flags1
35       ifbit fix_t_en,flags2
         jsr data_send jmp main
   ;************************************************
40       .sect autorun_select,rom,inpage
   autorun_states:ld a,autorun_stat
         add a,#low(jmp_a_r_stat)
         jid           ; jmp pcu,[a]
```

```
jmp_a_r_stat: .addr
a_r0.a_r1,a_r2,a_r3,a_r4,a_r5,a_r6,a_r7,a_r8,a_r9,a_r10,a_r11,a_r12;,a_r13,a_r14 a_r0: jmp a_r_stat0
a_r1: jmp a_r_stat1
a_r2: jmp a_r_stat2
a_r3: jmp a_r_stat3
a_r4: jmp a_r_stat4
a_r5: jmp a_r_stat5
a_r6: jmp a_r_stat6
a_r7: jmp a_r_stat7
a_r8: jmp a_r_stat8
a_r9: jmp a_r_stat9
a_r10:   jmp a_r_stat10
a_r11:   jmp a_r_stat11
a_r12:   jmp a_r_stat12
;a_r13:  jmp a_r_stat13
;a_r14:  jmp a_r_stat14 end_a_r_stat:ret
;*******************************
.sect autorun,rom
a_r_stat0:ld autorun_stat,#1
      ld home_stat,#0
      sbit home_command,buttons_flags a_r_stat1:ifbit home_command,buttons_flags
      ret ld linear_stat,#1   ; move linear forwards 1mm.
      ld rbyte1,#08    ; 0,1,2=0= speed1   ; 3=1= direction forwards ; 4=0= linear motor.
      ld rbyte2,#136
      ld rbyte3,#0     ; 1mm*136pulse per mm = 136 pulses.
      ld autorun_stat,#2
      ld temp,#low(wordautorun)
      jsr type_string1 a_r_stat1_1:rbit limits_c_en,limits_flags
      rbit stop1,lflags
      rbit stuck,flags1
a_r_stat1_2:sbit fix_t_en,flags2
      jmp end_a_r_stat a_r_stat2:ifeq linear_stat,#0   ; wait until linear motor complete mission.
      jmp a_r_stat2_0
```

```
        jmp end_a_r_stat a_r_stat2_0:ld a.hall1
              x a.zero_h1
              ld a.hall2
              x a.zero_h2
              rbit home.flags1
              ld ang_stat,#1   ; move angular down 2000 pulses.
              ld rbyte1,#010   ; 0,1,2=0= speed1   ; 3=0= direction down   ; 4=1= angular motor.
              ld rbyte2,#low(2000)
              ld rbyte3,#high(2000)
              rbit stop2,aflags
              ld autorun_stat,#3
              rbit stuck,flags1
              jmp a_r_stat1_2 a_r_stat3:ld linear_stat,#1   ; move linear forwards 40mm.
              ld rbyte1,#08    ; 0,1,2=0= speed1   ; 3=1= direction forwards   ; 4=0= linear motor.
              ld rbyte2,#low(5440)
              ld rbyte3,#high(5440)   ; 40mm*136pulse per mm = 5440.
              ld autorun_stat,#4
              jmp a_r_stat1_1 a_r_stat4:jsr epi_check    ; check if epiglotis sensed.
              ifbit epi,flags1
              jmp a_r_stat4_0
              ifeq linear_stat,#0   ; wait until linear motor complete mission.
              jmp a_r_stat7_0
              jmp end_a_r_stat a_r_stat4_0:ld linear_stat,#1   ; move linear backwards 6mm.
              ld rbyte1,#0    ; 0,1,2=speed1    ; 3=0= direction backwards   ; 4=0= linear
        motor.
              ld rbyte2,#low(816)
              ld rbyte3,#high(816); 6mm*136pulse per mm = 816.
              ld autorun_stat,#5
              jmp a_r_stat1_1 a_r_stat5:ifeq linear_stat,#0   ; wait until linear motor complete mission.
              jmp a_r_stat5_0
              jmp end_a_r_stat a_r_stat5_0:ld ang_stat,#1 ; move angular up 70 pulses.
              ld rbyte1,#018   ; 0,1,2=0= speed1   ; 3=1= direction up   ; 4=1= angular motor.
              ld rbyte2,#70
```

```
        ld rbyte3,#0
        ld autorun_stat,#6
        rbit stop2,aflags
        jmp a_r_stat1_2 a_r_stat6:ifeq ang_stat,#0 ; wait until angular motor complete mission.
        jmp a_r_stat6_0
        jmp end_a_r_stat a_r_stat6_0:rbit epi,flags1
        ld linear_stat,#1   ; move linear forwards 10mm.
        ld rbyte1,#08      ; 0,1,2=0= speed1   ; 3=1= direction forwards ; 4=0= linear motor.
        ld rbyte2,#low(1360)
        ld rbyte3,#high(1360)  ; 10mm*136pulse per mm = 1360.
        ld autorun_stat,#7
        jmp a_r_stat1_1 a_r_stat7:ifeq linear_stat,#0  ; wait until linear motor complete mission.
        jmp a_r_stat7_0
        jmp end_a_r_stat a_r_stat7_0:ld ang_stat,#1 ; move angular down 2000 pulses.
        ld rbyte1,#010    ; 0,1,2=0= speed1    ; 3=0= direction down  ; 4=1= angular motor.
        ld rbyte2,#low(2000)
        ld rbyte3,#high(2000)
        ld autorun_stat,#8
        rbit stop2,aflags
        rbit stuck,flags1
        jmp a_r_stat1_2 a_r_stat8:;ld linear_stat,#1    ; move linear forwards 50mm.
        ;ld rbyte1,#08    ; 0,1,2=0= speed1   ; 3=1= direction forwards ; 4=0= linear motor.
        ;ld rbyte2,#low(8160)
        ;ld rbyte3,#high(8160) ; 50mm*136pulse per mm = 6800.
        ld pls_cntr0,#low(6800)
        ld pls_cntr1,#high(6800)  ; 50mm*136pulse per mm = 6800.
        sbit direction,lflags  ; turn motor forwards
        rbit t2c0,t2cntrl
        sbit t2a,p1
        rbit control2,pa
        sbit control1,pa
        ld linear_stat,#6
        rbit en_calc,lflags
        ld autorun_stat,#9
```

```
        jmp a_r_stat1_1 a_r_stat9:ifeq linear_stat,#0  ; wait until linear motor complete mission.
        jmp a_r_stat9_0
        jmp end_a_r_stat a_r_stat9_0:ld ang_stat,#1 ; move angular up 2000 pulses.
        ld rbyte1,#018    ; 0,1,2=0= speed1    ; 3=1= direction up  ; 4=1= angular motor.
        ld rbyte2,#low(2000)
        ld rbyte3,#high(2000)
        ld autorun_stat,#10
        rbit stop2,aflags
        jmp a_r_stat1_2 a_r_stat10:;ld linear_stat,#1   ; move linear forwards 70mm.
        ;ld rbyte1,#08    ; 0,1,2=0= speed1    ; 3=1= direction forwards ; 4=0= linear motor.
        ;ld rbyte2,#low(9520)
        ;ld rbyte3,#high(9520) ; 70mm*136pulse per mm = 9520.

ld pls_cntr0,#low(9520)
        ld pls_cntr1,#high(9520)  ; 70mm*136pulse per mm = 9520.
        sbit direction,lflags  ; turn motor forwards
        rbit t2c0,t2cntrl
        sbit t2a,p1
        rbit control2,pa
        sbit control1,pa
        ld linear_stat,#6 ld autorun_stat,#11
        jmp a_r_stat1_1 a_r_stat11:ifeq linear_stat,#0 ; wait until linear motor complete mission.
        jmp a_r_stat11_0
        jmp end_a_r_stat a_r_stat11_0:sbit stop2,aflags
        rbit t3c0,t3cntrl
        sbit t3a,p1
        sbit control3,pa   ; turn off motor 2
        sbit control4,pa ;ld linear_stat,#1 ; move linear forwards 50mm.
        ;ld rbyte1,#08    : 0,1,2=0= speed1    ; 3=1= direction forwards ; 4=0= linear motor.
```

```
;ld rbyte2,#low(6800)
;ld rbyte3,#high(6800) ; 50mm*136pulse per mm = 6800.

ld pls_cntr0,#low(6800)
      ld pls_cntr1,#high(6800)  ; 50mm*136pulse per mm = 6800.
      sbit direction,lflags  ; turn motor forwards
      rbit t2c0,t2cntrl
      sbit t2a,p1
      rbit control2,pa
      sbit control1,pa
      ld linear_stat,#6 ld autorun_stat,#12
      jmp a_r_stat1_1 a_r_stat12:ifeq linear_stat,#0 ; wait until linear motor complete mission.
      jmp a_r_stat12_0
      jmp end_a_r_stat a_r_stat12_0:ld autorun_stat,#0
      jsr stop2motors
      sbit en_calc,lflags
      rbit start_stop,buttons_flags
      rbit stuck,flags1
      ld temp,#low(wordinplace)
      jsr type_string1
      jmp end_a_r_stat ;***********************************************
epi_check::;ld a,#4
      ;ifgt  a,pls_x1
      ;ret
      sc
      ld a,hall1
      ifgt a,zero_h1
      jmp epi_check0_1
      ld a,zero_h1
      subc a,hall1
      jmp epi_check0_2
epi_check0_1:subc a,zero_h1
epi_check0_2:ifgt a,#20
      sbit epi,flags1 sc
      ld a,hall2
```

```
        ifgt a,zero_h2
        jmp epi_check0_3
        ld a,zero_h2
        subc a,hall2
        jmp epi_check0_4
epi_check0_3:subc a,zero_h2
epi_check0_4:ifgt a,#20
        sbit epi,flags1
        ret
;*****************************************
.sect l_s_select.rom.inpage
linear_states:ld a,linear_stat
        add a,#low(jmp_l_stat)
        jid          ;jmp pcu,[a]

jmp_l_stat: .addr l_s0,l_s1,l_s2,l_s3,l_s4,l_s5,l_s6 l_s0:  jmp l_stat0
l_s1:  jmp l_stat1
l_s2:  jmp l_stat2
l_s3:  jmp l_stat3
l_s4:  jmp l_stat4
l_s5:  jmp l_stat5
l_s6:  jmp l_stat6 end_l_stat:jmp angular_states
;*********************************
.sect linear_states,rom l_stat0:  ifbit pulse,lflags
        jmp l_stat0_01     ; the motor made another pulse after stop order.
        jmp e_l_stat0 l_stat0_01:rbit pulse,lflags ifbit direction,lflags ; x update
        jmp l_stat0_03           ; x forwards ld a,pls_x1      ; before decreasing pls_x, check if pls_x>1
        ifne a,#0
        jmp l_stat0_02
;       ld a,pls_x0
;       ifgt a,#0
;       jmp l_stat0_02
        ifeq pls_x0,#0
```

```
        jmp e_l_stat0      ; do not decrease pls_x if 0.

l_stat0_02:sc
     ld a,pls_x0       ; x downwards
     subc a,#1
     x a,pls_x0
     ld a,pls_x1
     subc a,#0
     x a,pls_x1
     jmp e_l_stat0 l_stat0_03:rc          ; x forwards
     ld a,pls_x0
     adc a,#1
     x a,pls_x0
     ld a,pls_x1
     adc a,#0
     x a,pls_x1 e_l_stat0:jmp end_l_stat      ; ->0

;*******************************************
l_stat1:  ifbit direction,lflags ; check the previous direction.
     jmp l_stat1_02

; the direction was backwards.
     ifbit new_direction,rbyte1 ; check the new direction.
     jmp l_stat1_01
     jmp l_stat3 l_stat1_01:ld nxt_l_stat,#4    ; change direction to forwards.
     jmp l_stat1_05

; the direction was forwards.
l_stat1_02:ifbit new_direction,rbyte1  ; check the new direction.
     jmp l_stat4 ld a,pls_x1       ; before changing diretion to backwards
     ifne a,#0         ; check if pls_x=0.
     jmp l_stat1_04    ; if not then...
     ld a,pls_x0
     ifne a,#0
     jmp l_stat1_04 l_stat1_03:ld linear_stat,#0   ; if 0 then just stop motor.
```

```
        sbit stop1,lflags      ; stop motor 1.
        rbit stop,flags1
        sbit limits_c_en,limits_flags
        sc
        ifbit stop2,aflags
        rc
        ifc
        jmp l_stat1_06
        rbit start,flags1
        sbit end,flags1
        sbit type_end,lcd_flags
        jmp l_stat1_06 l_stat1_04:ld nxt_l_stat,#3    ; stop motor, wait and then
                               ; change direction to backwards.
l_stat1_05:ld linear_stat,#2
        ld cd_dly,#020
l_stat1_06:rbit t2c0,t2cntrl
        sbit t2a,pl
        rbit control1,pa       ; stop motor 1.
        rbit control2,pa
        jmp end_l_stat         ; ->O
;*******************************************************************
l_stat2: ifeq cd_dly,#0        ; delay before changing direction.
        jmp l_stat2_01
        jmp end_l_stat         ; ->O
l_stat2_01:ld a,nxt_l_stat
        x a,linear_stat
        jmp end_l_stat         ; ->O l_stat3: ld a,pls_x1           ; the direction is still backwards.
        ifne a,#0              ; check if pls_x=0
        jmp l_stat3_01         ; if not then...
        ld a,pls_x0
        ifne a,#0
        jmp l_stat3_01
        jmp l_stat1_03         ; if 0 then just stop motor and
                               ; return to linear stat 0.

l_stat3_01:ifbit home_limit,pbi
        jmp l_stat3_02
        jmp l_stat1_03
l_stat3_02:rbit direction,lflags ; turn motor backwards.
        rbit t2c0,t2cntrl
        sbit t2a,pl
```

```
            rbit control1,pa
            sbit control2,pa
            rbit t2a,pl
            jmp l_stat4_02 l_stat4:    ;ld a,pls_x1         ; 255mm*128pulsepermm=7f80H
            ;ifgt a,#0fe         ; if pls_x>7f00H then stop motor1.
            ;jmp l_stat1_03
            ifbit bottom_limit,pbi
            jmp l_stat4_01
            jmp l_stat1_03
   ;        ld linear_stat,#0
   ;        sbit stop1,lflags
   ;        jmp end_l_stat l_stat4_01: sbit direction,lflags  ; turn motor forwards
            rbit t2c0,t2cntrl
            sbit t2a,pl
            rbit control2,pa
            sbit control1,pa
            rbit t2a,pl
l_stat4_02: ld a,rbyte2           ; distanse update
            x a,pls_cntr0
            ld a,rbyte3
            x a,pls_cntr1
            ld a,rbyte1           ; velocity update
            and a,#7
            ifne a,#0
            jmp l_stat4_03
            ld t_ref0,#low(1000)  ; 1000 -> 500u per pulse
            ld t_ref1,#high(1000)
            jmp end_l_stat4
l_stat4_03: ifne a,#1
            jmp l_stat4_04
            ld t_ref0,#low(2000)  ; 2000 -> 1000u per pulse
            ld t_ref1,#high(2000)
            jmp end_l_stat4
l_stat4_04: ifne a,#2
            jmp l_stat4_05
            ld t_ref0,#low(3000)  ; 3000 -> 1500u per pulse
            ld t_ref1,#high(3000)
            jmp end_l_stat4
l_stat4_05: ifne a,#3
            jmp end_l_stat4
            ld t_ref0,#low(4000)  ; 4000 -> 2000u per pulse
```

```
           ld t_ref1,#high(4000)

end_l_stat4:
       ;****************************************************
  5    l_stat5: ifbit t2c0,t2cntrl   ; if motor 1 is already on.
               jmp e_l_stat5 rbit first_pulse,lflags
               rbit t2c1,t2cntrl    ; turn off the toggle output.
 10            rbit t2a,pl ld pt1hi,#020
               ld pt2hi,#080

15            ld tmr2lo,#0ff
               ld tmr2hi,#0ff
               ld t2ralo,#0ff
               ld t2rahi,#0ff
               ld t2rblo,#0ff
 20            ld t2rbhi,#0ff
               rbit t2pndb,t2cntrl
               sbit t2c0,t2cntrl    ; start timer 2 - pwm.
       l_stat5_01:ifbit t2pndb,t2cntrl
               jp l_stat5_02
 25            jp l_stat5_01
       l_stat5_02:rbit t2c0,t2cntrl  ; stop timer 2 - pwm.
               ld tmr2lo,#250       ; 250->t2.
               ld tmr2hi,#0
               ld t2ralo,#low(400)  ; 400->r2a.
 30            ld t2rahi,#high(400)
               ld t2rblo,#low(600)  ; 600->r2b.
               ld t2rbhi,#high(600)
               rbit t2a,pl
               sbit t2c1,t2cntrl    ; turn on the toggle output.
 35            sbit t2c0,t2cntrl    ; start timer 2 - pwm.
       ;       rbit stop1,lflags
       e_l_stat5:ld a,int_cntr
               sc
               subc a,#20
 40            x a,nolpulsetmr
               sbit limits_c_en,limits_flags
               ld linear_stat,#6
               ld nxt_l_stat,#0
               jmp end_l_stat       ; ->O
 45
```

```
l_stat6:   ifbit pulse,lflags
           jmp l_stat6_01
           ld a,nolpulsetmr
           ifne a,int_cntr
           jmp l_stat6_05
       ;   sbit stop1,lflags
       ;   sbit stuck,flags1
           jmp l_stat6_05 l_stat6_01:rbit pulse,lflags
           ld a,int_cntr
           sc
           subc a,#20
           x a,nolpulsetmr
           sbit limits_c_en,limits_flags
           sc              ; dec. pls_cntr
           ld a,pls_cntr0
           subc a,#1
           x a,pls_cntr0
           ld a,pls_cntr1
           subc a,#0
           x a,pls_cntr1
           ld a,pls_cntr1    ; check if pls_cntr=0
           ifne a,#0
           jmp l_stat6_02
           ld a,pls_cntr0
           ifne a,#0
           jmp l_stat6_02
           sbit stop1,lflags l_stat6_02::;ifbit first_pulse,lflags
           sbit en_calc,lflags
           sbit first_pulse,lflags ifbit direction,lflags ; x_update
           jmp l_stat6_04
           ld a,pls_x1       ; check if pls_x>1
           ifne a,#0
           jmp l_stat6_03
           ld a,pls_x0
           ifgt a,#0
           jmp l_stat6_03
       ;   ld pls_x0,#0
```

```
        sbit stop1,lflags
        ld nxt_l_stat,#0
        jmp l_stat6_05 l_stat6_03:sc              ; x_downwards
        ld a,pls_x0
        subc a,#1
        x a,pls_x0
        ld a,pls_x1
        subc a,#0
        x a,pls_x1
        jmp l_stat6_05
l_stat6_04:rc              ; x_forwards
        ld a,pls_x0
        adc a,#1
        x a,pls_x0
        ld a,pls_x1
        adc a,#0
        x a,pls_x1
        ifgt a,#086 ; the lcd can show only 256 mm (= 256*136=34816=08800H).
        sbit stop1,lflags l_stat6_05:ifbit stop1,lflags
        jmp e_l_stat6
        ifbit en1_calc,lflags
        jsr v_calc
        jmp end_l_stat    ; ->O e_l_stat6:rbit t2c0,t2cntrl
        sbit t2a,pl
        rbit control1,pa   ; turn off motor 2.
        rbit control2,pa
        ld a,nxt_l_stat
        x a,linear_stat
        ifbit stop2,aflags
        jmp e_l_stat6_0
        jmp end_l_stat    ; ->O
e_l_stat6_0:rbit start,flags1
        rbit stop,flags1
        ifbit self_t_command,buttons_flags
        jmp end_l_stat    ; ->O
        ifbit start_stop,buttons_flags
        jmp end_l_stat    ; ->O
        ifbit home_command,buttons_flags
```

```
            jmp end_1_stat    ; ->O sbit type_end,lcd_flags
            sbit end,flags1
            jmp end_1_stat    ; ->O ;*********************************************
        .sect a_s_select,rom,inpage
        angular_states:ld a,ang_stat
            add a,#low(jmp_a_stat)
            jid              ; jmp pcu,[a]

jmp_a_stat: .addr a_s0,a_s1,a_s2,a_s3,a_s4,a_s5,a_s6,a_s7 a_s0: jmp a_stat0
        a_s1: jmp a_stat1
        a_s2: jmp a_stat2
        a_s3: jmp a_stat3
        a_s4: jmp a_stat4
        a_s5: jmp a_stat5
        a_s6: jmp a_stat6
        a_s7: jmp a_stat7 end_a_stat:jmp main1
;*********************************
        .sect angular_states,rom
        a_stat0:  ifbit pulse2,aflags
            jmp a_stat0_01
            jmp e_a_stat0 a_stat0_01:rbit pulse2,aflags
            ifbit direction2,aflags   ; y update
            jmp a_stat0_02
            jmp a_stat0_03 a_stat0_02:sc              ; y down
            ld a,pls_y0
            subc a,#1
            x a,pls_y0
            ld a,pls_y1
            subc a,#0
            x a,pls_y1
            jmp e_a_stat0 a_stat0_03:rc              ; y up
```

```
            ld a,pls_y0
            adc a,#1
            x a,pls_y0
            ld a,pls_y1
 5          adc a,#0
            x a,pls_y1 e_a_stat0:jmp end_a_stat      ; ->O
       ;*******************************
10     a_stat1:

;      ld a,pls_y1          ; check if the the probe is not too high or to low.
       ;      ifgt a,#094
       ;      jmp a_stat1_00
15     ;      ld a,#066
       ;      ifgt a,pls_y1
       ;      jmp a_stat1_01
       ;      jmp a_stat1_03
       ;a_stat1_00:ifbit new_direction,rbyte1; if too high enable only down movment.
20     ;      jmp a_stat1_02
       ;      jmp a_stat1_03
       ;a_stat1_01:ifbit new_direction,rbyte1; if too low enable only up movment.
       ;      jmp a_stat1_03
       ;      jmp a_stat1_02
25     ;
       ;a_stat1_02:ld ang_stat,#0    ; just stop motor.
       ;      ld nxt_a_stat,#0
       ;      sbit stop2,aflags      ; stop motor 2.
       ;      sbit type_end,flags2
30     ;      jmp a_stat1_08
       ;
       a_stat1_03:ifbit direction2,aflags    ; check the previous direction.
            jmp a_stat1_05

35          ifbit new_direction,rbyte1 ; the direction was down-check the new direction.
            jmp a_stat1_04
            jmp a_stat3 a_stat1_04:ld nxt_a_stat,#4   ; stop motor, wait and then change direction to up.
40          jmp a_stat1_07 a_stat1_05:ifbit new_direction,rbyte1 ; the direction was up-check the new direction.
            jmp a_stat4

45     a_stat1_06:ld nxt_a_stat,#3   ; stop motor, wait and then change direction to down.
```

```
a_stat1_07:ld ang_stat,#2       ; delay for the motor to make a complete stop.
        ld cd_dly,#17
a_stat1_08:rbit t3c0,t3cntrl
        sbit t3a,pl
        sbit control3,pa        ; stop motor 2.
        sbit control4,pa
        jmp end_a_stat          ; ->O
;************************************************************
a_stat2: ifeq cd_dly,#0         ; delay before changing direction.
        jmp a_stat2_01
        jmp end_a_stat          ; ->O
a_stat2_01:ld a,nxt_a_stat
        x a,ang_stat
        jmp end_a_stat          ; ->O
;************************************************************
a_stat3: rbit direction2,aflags ; turn motor backwards.
        rbit t3c0,t3cntrl
        sbit t3a,pl
        rbit control3,pa
        sbit control4,pa
        rbit t3a,pl
        jmp a_stat4_01
;****************************************
a_stat4: sbit direction2,aflags ; turn motor forwards
        rbit t3c0,t3cntrl
        sbit t3a,pl
        rbit control4,pa
        sbit control3,pa
        rbit t3a,pl
a_stat4_01:ld a,rbyte2          ; distanse update
        x a,plsy_cntr0
        ld a,rbyte3
        x a,plsy_cntr1 ld a,rbyte1             ; velosity update
        and a,#7
        ifne a,#0
        jmp a_stat4_02
        ld at_ref0,#low(6000)   ; 6000 -> 3000u per pulse
        ld at_ref1,#high(6000)
        jmp end_a_stat4
a_stat4_02:ifne a,#1
        jmp a_stat4_03
        ld at_ref0,#low(7000)   ; 7000 -> 3500u per pulse
```

```
            ld at_ref1,#high(7000)
            jmp end_a_stat4
    a_stat4_03:ifne a,#2
            jmp a_stat4_04
            ld at_ref0,#low(8000)   ; 8000 -> 4000u per pulse
            ld at_ref1,#high(8000)
            jmp end_a_stat4
    a_stat4_04:ifne a,#3
            jmp end_a_stat4
            ld at_ref0,#low(9000)   ; 9000 -> 4500u per pulse
            ld at_ref1,#high(9000)

end_a_stat4:ld nxt_a_Stat,#6
    ;***********************************************
    a_stat5:  ;ifbit t3c0,t3cntrl ; if motor 2 is already on.
              ;jmp e_a_stat5 ld apt1hi,#020
            ld apt2hi,#080

;   rbit firsty_pulse,aflags
            rbit t3c1,t3cntrl   ; turn off the toggle output.
            rbit t3a,pl
            ld tmr3lo,#0ff
            ld tmr3hi,#0ff
            ld t3ralo,#0ff
            ld t3rahi,#0ff
            ld t3rblo,#0ff
            ld t3rbhi,#0ff
            rbit t3pndb,t3cntrl
            sbit t3c0,t3cntrl   ; start timer 3 - pwm.
    a_stat5_01:ifbit t3pndb,t3cntrl
            jp a_stat5_02
            jp a_stat5_01
    a_stat5_02:rbit t3c0,t3cntrl    ; stop timer 3 - pwm.
            ld tmr3lo,#250          ; 250->t3.
            ld tmr3hi,#0
            ld t3ralo,#low(500)     ; 500->r3a.
            ld t3rahi,#high(500)
            ld t3rblo,#low(500)     ; 500->r3b.
            ld t3rbhi,#high(500)
            rbit t3a,pl
            sbit t3c1,t3cntrl   ; turn on the toggle output.
            sbit t3c0,t3cntrl   ; start timer 3 - pwm.
```

```
e_a_stat5::ld a,int_cntr
          ;sc
          :subc a,#50
          ;x a,noapulsetmr
          ld a,nxt_a_stat
          x a,ang_stat
          ld nxt_a_stat,#0
          jmp end_a_stat     ; ->0
;*********************************
a_stat6:  ifbit pulse2,aflags
          jmp a_stat6_01

;ld a,noapulsetmr
          ;ifne a,int_cntr
          ;jmp a_stat6_06
          ;sbit stop2,aflags
          :sbit stuck,flags1
          jmp a_stat6_06 a_stat6_01:rbit pulse2,aflags
          ;ld a,int_cntr
          ;sc
          :subc a,#50
          ;x a,noapulsetmr
          sc              ; dec. plsy_cntr
          ld a,plsy_cntr0
          subc a,#1
          x a,plsy_cntr0
          ld a,plsy_cntr1
          subc a,#0
          x a,plsy_cntr1
          ld a,plsy_cntr1      ; check if plsy_cntr=0
          ifne a,#0
          jmp a_stat6_02
          ld a,plsy_cntr0
          ifne a,#0
          jmp a_stat6_02
          sbit stop2,aflags
          ld nxt_a_stat,#0 a_stat6_02::;ifbit firsty_pulse,aflags
          ;    sbit en_calc2,aflags
               sbit firsty_pulse,aflags ifbit direction2,aflags   ; y_update
```

```
        jmp a_stat6_04
        ld a,pls_y1         ; check if pls_y>6500H
        ifgt a,#0           ; 065
        jmp a_stat6_03
        sbit stop2,aflags
        ld nxt_a_stat,#0
        jmp a_stat6_06 a_stat6_03:sc               ; y_down
        ld a,pls_y0
        subc a,#1
        x a,pls_y0
        ld a,pls_y1
        subc a,#0
        x a,pls_y1
        jmp a_stat6_06 a_stat6_04:ld a,#0ff        ; 096
        ifgt a,pls_y1
        jmp a_stat6_05
        sbit stop2,aflags
        ld nxt_a_stat,#0
        jmp a_stat6_06 a_stat6_05:rc               ; y_up
        ld a,pls_y0
        adc a,#1
        x a,pls_y0
        ld a,pls_y1
        adc a,#0
        x a,pls_y1 a_stat6_06:ifbit stop2,aflags
        jmp e_a_stat6
        ifbit en1_calc2,aflags
        jsr v2_calc
        jmp end_a_stat      ; ->O e_a_stat6:
        rbit t3c0,t3cntrl
        sbit t3a,pl
        sbit control3,pa    ; turn off motor 2
        sbit control4,pa
        ld a,nxt_a_stat
        x a,ang_stat
```

```
        ifbit stop1,lflags
        jmp e_a_stat6_0
        jmp end_a_stat    ; ->O
    e_a_stat6_0:rbit start,flags1
5       rbit stop,flags1
        ifbit self_t_command,buttons_flags
        jmp end_a_stat    ; ->O
        ifbit start_stop,buttons_flags
        jmp end_a_stat    ; ->O
10      ifbit home_command,buttons_flags
        jmp end_1_stat    ; ->O sbit end,flags1
        sbit type_end,lcd_flags
15      ifbit stuck,flags1
        sbit type_stuck,lcd_flags
        jmp end_a_stat    ; ->O ;********************************************
20  a_stat7:  ifbit pulse2,aflags
        jmp a_stat7_01
        jmp e_a_stat7 a_stat7_01:rbit pulse2,aflags
25      ifbit direction2,aflags   ; y update
        jmp a_stat0_03 a_stat7_02:sc             ; y down
        ld a,pls_y0
30      subc a,#1
        x a,pls_y0
        ld a,pls_y1
        subc a,#0
        x a,pls_y1
35      jmp e_a_stat7 a_stat7_03:rc             ; y up
        ld a,pls_y0
        adc a,#1
40      x a,pls_y0
        ld a,pls_y1
        adc a,#0
        x a,pls_y1

45  e_a_stat7:jmp end_a_stat  ; ->O
```

```
        ;************************************************
        .sect stop_subroutines,rom
        stop2motors:sbit stop1,lflags ; turn off motor 1
            rbit t2c0,t2cntrl
            sbit t2a,pl
            rbit control1,pa
            rbit control2,pa
            ld linear_stat,#0
            ld nxt_l_stat,#0
            sbit stop2,aflags  ; turn off motor 2
            rbit t3c0,t3cntrl
            sbit t3a,pl
            sbit control3,pa
            sbit control4,pa
            ld ang_stat,#0
            ld nxt_a_stat,#0
            ret
        stop_operation:rbit stop_command,buttons_flags
            jsr stop2motors
            sbit en_calc,lflags
            sbit fix_t_en,flags2
            rbit enddata,flags1
            rbit start,flags1
            rbit end,flags1
            sbit stop,flags1
            sbit type_stop,lcd_flags
            rbit self_t_command,buttons_flags
            ld selft_stat,#0
            rbit start_stop,buttons_flags
            ld autorun_stat,#0
        ;   rbit home_command_pc,buttons_flags
            rbit home_command,buttons_flags
            ld home_stat,#0
            ret
        ;************************************************
        .sect s_t_select,rom,inpage
        self_t_states:ld a,selft_stat
            add a,#low(jmp_st_stat)
            jid          ; jmp pcu,[a]

jmp_st_stat: .addr s_t0,s_t1,s_t2,s_t3,s_t4,s_t5,s_t6 s_t0: jmp self_test0
        s_t1: jmp self_test1
        s_t2: jmp self_test2
```

```
s_t3:   jmp self_test3
s_t4:   jmp self_test4
s_t5:   jmp self_test5
s_t6:   jmp self_test6 end_st_stat:jmp main0
;************************************
.sect self_test,rom
self_test0:ld temp,#low(wordselftest)
        jsr type_string1
        ifbit home_limit,pbi
        jmp self_test0_0    ; 1-micro switch open - not in home position.
        rbit home_command,buttons_flags
        ld home_stat,#0
        jmp self_test1_0    ; 0-micro switch closed - in home position.

self_test0_0:sbit home_command,buttons_flags
        ld home_stat,#0
        ld selft_stat,#1
        jmp end_st_stat self_test1:ifbit home_command,buttons_flags
        jmp end_st_stat self_test1_0:ld linear_stat,#1 ; move linear forwards 50mm.
        ld rbyte1,#08       ; 0,1,2=0= speed1  ; 3=1= direction forwards ; 4=0= linear motor.
        ld rbyte2,#low(6850)
        ld rbyte3,#high(6850) ; 50mm*136pulse per mm = 6800.
        ld selft_stat,#2
self_test1_1:rbit limits_c_en,limits_flags
        rbit stop1,lflags
self_test1_2:jmp end_st_stat self_test2:ifeq linear_stat,#0  ; wait until linear motor complete mission.
        jmp self_test2_0
        jmp end_st_stat self_test2_0:ld ang_stat,#1    ; move angular up 150 pulses.
        ld rbyte1,#018      ; 0,1,2=0= speed1  ; 3=1= direction up      ; 4=1= angular motor.
        ld rbyte2,#150
        ld rbyte3,#0
        ld selft_stat,#3
        rbit stop2,aflags
        sbit en_calc2,aflags
        jmp self_test1_2
```

```
self_test3:ifeq ang_stat,#0 ; wait until angular motor complete mission.
        jmp self_test3_0
        jmp end_st_stat self_test3_0:rbit en_calc2,aflags
        ld ang_stat,#1 ; move angular down 400 pulses.
        ld rbyte1,#010   ; 0,1,2=0= speed1   ; 3=0= direction down  ; 4=1= angular motor.
        ld rbyte2,#low(300)
        ld rbyte3,#high(300)
        ld selft_stat,#4
        rbit stop2,aflags
        jmp self_test1_2 self_test4:ifeq ang_stat,#0 ; wait until angular motor complete mission.
        jmp self_test4_0
        jmp end_st_stat self_test4_0:ld ang_stat,#1   ; move angular again up 150 pulses.
        ld rbyte1,#018   ; 0,1,2=0= speed1   ; 3=1= direction up       ; 4=1= angular motor.
        ld rbyte2,#150
        ld rbyte3,#0
        ld selft_stat,#5
        rbit stop2,aflags
        sbit en_calc2,aflags
        jmp self_test1_2 self_test5:ifeq ang_stat,#0 ; wait until angular motor complete mission.
        jmp self_test5_0
        jmp end_st_stat self_test5_0:rbit en_calc2,aflags
        ld linear_stat,#1 ; move linear backwards 50mm.
        ld rbyte1,#0     ; 0,1,2=0= speed1   ; 3=0= direction backwards  ; 4=0= linear motor.
        ld rbyte2,#low(6850)
        ld rbyte3,#high(6850) ; 50mm*136pulse per mm = 6800.
        ld selft_stat,#6
        jmp self_test1_1 self_test6:ifeq linear_stat,#0 ; wait until linear motor complete mission.
        jmp self_test6_0
        jmp end_st_stat
```

49

```
self_test6_0:ld selft_stat,#0
        rbit self_t_command,buttons_flags
        rbit stuck,flags1
        ld temp,#low(wordready)
        jsr type_string1
        jmp end_st_stat ;******************************************************
.sect h_p_select,rom,inpage
home_p_states:ld a,home_stat
        add a,#low(jmp_h_stat)
        jid              ; jmp pcu,[a]

jmp_h_stat: .addr h_p0,h_p1 h_p0:jmp home_p0
h_p1:jmp home_p1

;*************************************************************************
**
.sect home_positioning,rom
home_p0:  ifbit home_limit,pbi ; 0-micro switch closed - in home position,
        jmp home_p0_2            ; 1-micro switch open - not in home position.
        jmp home_p1_0 home_p0_2:jsr stop2motors
        ld lcd_flags,#0
        rbit direction,lflags  ; so the bottom wouldn't shut down the motor.
        ld linear_stat,#1   ; move linear backwards 200mm.
        ld rbyte1,#0     ; 0,1,2=0= speed1    ; 3=0= direction backwards   ; 4=0= linear motor.
        ld rbyte2,#low(27200)
        ld rbyte3,#high(27200) ; 200mm*136pulse per mm = 27200.
        rbit stop1,lflags
        sbit fix_t_en,flags2
        rbit start,flags1
        rbit stop,flags1
        rbit end,flags1
        rbit enddata,flags1
        ld home_stat,#1
        ifbit self_t_command,buttons_flags
        ret
```

```
        ld temp,#low(wordhome)
        jsr type_string1 home_p1: ifeq linear_stat,#0   ; wait until linear motor complete mission.
        jmp home_p1_0
        ret home_p1_0:ld home_stat,#0
        rbit home_command,buttons_flags
        rbit epi,flags1
    ;   ifbit stuck,flags1
    ;   jmp home_p1_1
        ld pls_x0,#0
        ld pls_x1,#0
        ld pls_y0,#0
        ld pls_y1,#080
home_p1_1:ifbit self_t_command,buttons_flags
        ret ifbit stuck,flags1
        ret
        ld temp,#low(wordready)
        jsr type_string1
        ret
;***************************************************
        .sect limits_check,rom
limits_check:ld a,pbi      ; general limits check (limits = b5,b6,b7).
        and a,#060    ; 0e0 - if the angular limit switch is on.
        ifne a,#060
        jmp limits_check0_0
        rbit home,flags1  ; signal to the pc that we are not in home position.
        rbit bottom,flags1    ; signal to the pc that we are not in buttom position.
        ret limits_check0_0:x a,b
        ifbit home_limit,b
        jmp limits_check1_0 sbit home.flags1   ; signal to the pc that we are in home position.
        rbit bottom.flags1    : signal to the pc that we are not in buttom position.
        ifbit direction,lflags
        jmp limits_check0_1
        sbit stop1,lflags    ; turn off motor 1
        rbit t2c0,t2cntrl
```

```
                sbit t2a,p1
                rbit control1,pa
                rbit control2,pa
                ld linear_stat,#0
 5              ifbit stop2,aflags
                rbit start,flags1
                ld temp,#low(wordready)
                jsr type_string1
        limits_check0_1:
10              ld pls_x1,#0
                ld pls_x0,#0
                ld pls_y0,#0
                ld pls_y1,#080
                jmp limits_check2_1
15
        limits_check1_0:rbit home,flags1    ; signal to the pc that we are not in home position.
                ifbit bottom_limit,b
                jmp limits_check2_0
                sbit bottom,flags1          ; signal to the pc that we are in buttom position.
20              ifbit direction,lflags
                jmp limits_check1_1
                jmp limits_check1_2 limits_check1_1:jsr stop2motors
25              rbit start,flags1
                ld temp,#low(wordbottom)
                jsr type_string1 limits_check1_2:ld pls_x1,#066 ; to be calibrated.
30              ld pls_x0,#088
                jmp limits_check2_1 limits_check2_0:rbit bottom,flags1    ; signal to the pc that we are not in buttom position.
        limits_check2_1:
35              ;ifbit angular_limit,b
                ret

;************************************************

40      buttons_test:rbit buttons_t_en,buttons_flags
                ld a,p1i
                and a,#0a0
                x a,b
                ifeq b,#0a0
45              jmp b_t0_01
```

```
            jmp b_t0_03 b_t0_01:    ifeq ritut,#0      ; no key was pressed.
            jmp b_t0_02
            ld a,ritut
            dec a
            x a,ritut
    b_t0_02:    ld start_stop_cntr,#0
            ld home_position_cntr,#0
            jmp end_b_test b_t0_03:    ifeq ritut,#0      ; a key was pressed. ritut checks if it is a real press on
            jmp b_t1_00        ; a key, or just a vibration of the key.
    b_t0_04:    ld ritut,#5
    ;       ld start_stop_cntr,#0
    ;       ld home_position_cntr,#0
            jmp b_t0_02 b_t1_00:    ifbit start_stop,b
            jmp b_t2_00        ; start-stop key was not pressed.
            ifbit start_stop,buttons_flags ; start-stop key was pressed to stop operatio.
            jmp b_t1_02
            ifbit home_command,buttons_flags
            jmp b_t1_02
            ifbit self_t_command,buttons_flags
            jmp b_t1_02
            ld a,start_stop_cntr ; start-stop key was pressed to start operation.
            inc a
            x a,start_stop_cntr
            ifgt a,#150
            jmp b_t1_01
            jmp b_t2_00
    ;--------------- start/stop autorun key was pressed ------------------
    b_t1_01:    ifbit start_stop,buttons_flags
            jmp b_t1_02
            sbit start_stop,buttons_flags  ; start button was pressed to start operation.
            ld autorun_stat,#0
            jmp b_t0_04 b_t1_02:    sbit stop_command,buttons_flags; start button was pressed again to stop operation.
            rbit start_stop,buttons_flags
            ld autorun_stat,#0
            jmp b_t0_04
```

```
b_t2_00:    ifbit home_position,b
            jmp end_b_test
            ld a,home_position_cntr
            inc a
            x a,home_position_cntr
            ifgt a,#150
            jmp b_t2_01
            jmp end_b_test
;--------------- home positon/self test  key was pressed -----------------
b_t2_01:    ifbit home_limit,pbi    ; 0-micro switch closed - in home position,
            jmp b_t2_03
b_t2_02:    rbit home_command,buttons_flags ; not in home position - go to home position.
            sbit self_t_command,buttons_flags
            ld selft_stat,#0
            sbit fix_t_en,flags2
            ld data_cntr,#21
            ld save_ptr,#0
            ld send_ptr,#0
            rbit enddata,flags1
            rbit start,flags1
            rbit end,flags1
            rbit stop,flags1
            jmp b_t0_04 b_t2_03:    ld a,pls_x0
            ifgt a,#0
            jmp b_t2_04
            ifeq pls_x1,#0
            jmp b_t2_02
b_t2_04:    sbit home_command,buttons_flags ; not in home position - go to home position.
            ld home_stat,#0
            sbit fix_t_en,flags2
            ld data_cntr,#21
            ld save_ptr,#0
            ld send_ptr,#0
            rbit enddata,flags1
            rbit start,flags1
            rbit end,flags1
            rbit stop,flags1
            jmp b_t0_04 end_b_test:ret
;****************************************************
.sect interups.rom.abs=0ff ;interrupts address
            push a
```

```
           ld a,s
           push a
           ld a,b
           push a
 5         ld a,x
           push a
           ld a,psw
           push a
           ld s,#0
10         vis end_intr:  rc
           rbit hc,psw
           pop a
15         and a,#0c0      ;save only c and hc
           or a,psw
           x a,psw pop a
20         x a,x
           pop a
           x a,b
           pop a
           x a,s
25         pop a
           reti
;***************************
.sect int_addres,rom,abs=01e0
           .addrw reset    ;vis without any interrupt
30         .addrw reset    ;port 1 or wake up interupts
           .addrw reset    ;t3 b
           .addrw reset    ;t3 a
           .addrw reset    ;t2 b
           .addrw reset    ;t2 a
35         .addrw trns0    ;transmit
           .addrw rec0     ;receive
           .addrw reset    ;reserved
           .addrw reset    ;micro wire
           .addrw tmr1b    ;tmr1      ;t1b
40         .addrw tmr1a    ;tmr1      ;t1a
           .addrw tmr0     ;timer0
           .addrw reset    ;external interrupt-g0
           .addrw reset    ;reserved
           .addrw reset    ;software intr interrupt
45         ;***************************
```

```
.sect timer0,rom tmr0:   rbit t0pnd,icntrl
        drsz lcd_cntr      ; lcd counter to enable lcd update every 0.1sec (25*4msec).
        jmp tmr0_01
        sbit lcdupdate,flags2 tmr0_01:   ld a,int_cntr    ; timer0 interrupts counter, used to help timing a2d,fix
        dec a              ; transmit, and other actions according to timer0 cycles.
        x a,int_cntr
        ifbit 0,int_cntr ; odd -   ; enable fix transmit.
        jmp tmr0_011
        sbit a2den,flags2 ; even -  ; enable a2d.
        jmp tmr0_02
tmr0_011: sbit fix_t_en1,flags2
        sbit buttons_t_en,buttons_flags tmr0_02:   ifbit stop1,lflags
        jmp tmr0_04 ifbit en_calc,lflags
        jmp tmr0_03
        jmp tmr0_04 tmr0_03:   sc              ; pt=pt2-pt1 =time per pulse
        ld a,pt2lo
        subc a,pt1lo
        x a,ptlo
        ld a,pt2hi
        subc a,pt1hi
        x a,pthi sbit en1_calc,lflags tmr0_04:   ifbit stop2,aflags
        jmp tmr0_06 ifbit en_calc2,aflags
        jmp tmr0_05
        jmp tmr0_06 tmr0_05:   sc              ; pt=pt2-pt1 =time per pulse
        ld a,apt2lo
        subc a,apt1lo
        x a,aptlo
```

```
            ld a,apt2hi
            subc a,apt1hi
            x a,apthi sbit en1_calc2,aflags tmr0_06:
        end_tmr0: ld a,cd_dly ; delay before changing direction.
            ifne a,#0
            dec a
            x a,cd_dly
            drsz uart_tmr
            jmp end_intr
            ld rec_stat,#0
            jmp end_intr
        ;****************************************************
        .sect timer1,rom tmr1a:  rbit t1c0,cntrl ifbit t1pnda,psw
            jmp tmr1a1
            jmp end_tmr1a tmr1a1: rbit t1pnda,psw
            ld a,pt1lo
            x a,pt2lo
            ld a,pt1hi
            x a,pt2hi
            ld a,t1ralo
            x a,pt1lo
            ld a,t1rahi
            x a,pt1hi
            sbit pulse,lflags end_tmr1a:jmp end_intr
        ;****************************************************
        tmr1b:  rbit t1pndb,icntrl
            ld a,apt1lo
            x a,apt2lo
            ld a,apt1hi
            x a,apt2hi
            ld a,t1rblo
            x a,apt1lo
            ld a,t1rbhi
```

```
            x a,apt1hi sbit pulse2,aflags end_tmr1b:jmp end_intr
;************************************************
   .sect uart_transmit,rom,inpage trns0:  ld a,trns_stat
        add a,#low(jmp_t_stat)
        jid              ; jmp pcu,[a]

jmp_t_stat: .addr t_s0,t_s1 t_s0:   jmp t_stat0
t_s1:   jmp t_stat1 end_t_stat:jmp end_intr
;************************************************
t_stat0: rbit eti,enui
        ld trns_stat,#0
        jmp end_t_stat t_stat1:  ld a,send_ptr
        ifgt a,#89       ; 0-89 => 90 bytes
        jmp t_stat1_01
        ld a,send_ptr
        x a,b
        ld s,#1
        ld a,[b+]
        x a,tbuf
        ld s,#0
        ld a,b
        x a,send_ptr
        jmp end_t_stat t_stat1_01:ifgt a,#183   ; 90-179 => 90
bytes+1(buttons_flags)+1(t_check)+2('ED'[=END])
        jmp end_t_stat1
        ld a,send_ptr
        sc
        subc a,#90
        x a,b
        ld s,#2
```

```
        ld a,[b+]
        x a,tbuf
        ld s,#0
        ld a,b
 5      add a,#90
        x a,send_ptr
        jmp end_t_stat end_t_stat1:ld send_ptr,#0
10      rbit eti.enui
        ld trns_stat,#0
        jmp end_t_stat ;*********************************************
15      .sect uart_receive,rom,inpage rec0:   ld a,rbuf       ; receive interrupt.
        x a,b
        ld a,check_sum
20      add a,b
        x a,check_sum
        ld a,rec_stat
        add a,#low(jmp_r_stat)
        jid             ; jmp pcu,[a]
25
jmp_r_stat: .addr r_s0,r_s1,r_s2,r_s3 r_s0:   jmp r_stat0
r_s1:   jmp r_stat1
30 r_s2: jmp r_stat2
r_s3:   jmp r_stat3 end_r_stat:jmp end_intr
;********************************
35      .sect receive_states,rom r_stat0:  ld check_sum,#0
          ld a,b
          ifne a,#0f5
40        jmp e_r_stat0 ld rec_stat,#1
          ld check_sum,#0f5
e_r_stat0:ld uart_tmr,#0ff
45        jmp end_r_stat
```

```
r_stat1: ld a,b
        ifeq a,#'A'      ; (041)   ; Advance - moving command.
        jmp r_stat2_00
        ifeq a,#'S'      ; Stop command.
        jmp r_stat1_01
        ifeq a,#'H'      ; Home position command.
        jmp r_stat1_02
        ifeq a,#'T'      ; Self Test command.
        jmp r_stat1_03
        ifeq a,#'O'      ; Operate auto run command.
        jmp r_stat1_04
        ifeq a,#'P'      ; Ping (test communication) command.
        jmp r_stat1_05
        ld rec_stat,#0
        jmp end_r_stat r_stat1_01:sbit stop_command,buttons_flags   ; 'S' - Stop.
        ld tbyte1,#0f5
        jmp e_r_stat2 r_stat1_02:sbit home_command,buttons_flags   ; 'H' - Home position.
        ld home_stat,#0
e_r_stat1:ld tbyte1,#0f5
        sbit fix_t_en,flags2
        ld data_cntr,#21
        ld save_ptr,#0
        ld send_ptr,#0
        rbit enddata,flags1
        rbit start,flags1
        rbit end,flags1
        rbit stop,flags1
        jmp e_r_stat2 r_stat1_03:sbit self_t_command,buttons_flags ; 'T' - Self Test.
        ld selft_stat,#0
        jmp e_r_stat1 r_stat1_04:sbit start_stop,buttons_flags     ; 'O' - Operate auto run command.
        ld autorun_stat,#0
        jmp e_r_stat1 r_stat1_05:ld tbyte1,#0f5                    ; 'P' - Ping.
        ld pb,#0f0
        jmp e_r_stat2
```

```
r_stat2_00:ld rec_stat,#2
        ld rbyte_num,#4    ; number of bytes to be received
        ld receive_ptr,#rbyte1
        jmp end_r_stat
r_stat2:  ld a,receive_ptr    ; rbuf -> [receive_ptr]
        x a,x
        ld a,b              ; receive_ptr + 1 -> receive_ptr
        x a,[x+]
        ld a,x
        x a,receive_ptr
        drsz rbyte_num
        jmp end_r_stat
        sbit start,flags1
        rbit stop,flags1
        rbit end,flags1
        sbit fix_t_en,flags2
        ifeq trns_stat,#1
        jmp r_stat2_01
        ld data_cntr,#21    ; ************
        ld save_ptr,#0
        ld send_ptr,#0
r_stat2_01:ifbit motor,rbyte1 ; 0-motor1, 1-motor2.
        jmp r_stat2_03 ld a,rbyte3         ; motor 1
        ifne a,#0
        jmp r_stat2_02
        ld a,rbyte2
        ifgt a,#0
        jmp r_stat2_02
        sbit stop1,lflags   ; distance=0 ->Stop motor!!
        rbit start,flags1
        sbit end,flags1
        ld nxt_l_stat,#0
        ld linear_stat,#6
        jmp r_stat2_05
r_stat2_02:ld linear_stat,#1
        sbit type_start,lcd_flags; type 'start' at line 2 of lcd.
        rbit limits_c_en,limits_flags
        rbit enddata,flags1
        rbit stop1,lflags
        jmp r_stat2_05 r_stat2_03:ld a,rbyte3       ; motor 2
```

```
            ifne a,#0
            jmp r_stat2_04
            ld a,rbyte2
            ifgt a,#0
 5          jmp r_stat2_04
            sbit stop2,aflags  ; distance=0 ->Stop motor!!
            rbit start,flags1
            sbit end,flags1
            ld nxt_a_stat,#0
10          ld ang_stat,#6
            jmp r_stat2_05
r_stat2_04:ld ang_stat,#1  ; motor 2
            sbit type_start,lcd_flags; type 'start' at line 2 of lcd.
            rbit enddata,flags1
15          rbit stop2,aflags r_stat2_05:ld a,check_sum    ; load byte to transmit
            x a,tbyte1
20  e_r_stat2:ld a,tbyte1
            ifeq trns_stat,#0
            x a,tbuf
            ld rec_stat,#0
            rbit stuck,flags1
25          jmp end_r_stat r_stat3:  jmp end_r_stat
;***********************************************************
            .sect datasend,rom
30
data_send:ifbit fix_t_en1,flags2
            jmp d_s0
            ret 35  d_s0: rbit fix_t_en1,flags2
            drsz data_cntr
            jmp d_s1

; transmit s2 and s3
40          ld a,#13    ; 13 is the sync. sign.
            x a,tbuf    ; then send the data to the computer
            ld a,buttons_flags
            x a,b
            ld a,t_check
45          ld s,#2
```

```
          x a,05a
          ld a,b
          x a,05b
          ld s,#1
 5        ld a,059
          ld s,#0
      ;   x a,0
      :   ifbit enddata,0
          ifbit enddata.flags1
10        rbit fix_t_en.flags2
          ld t_check.#0
          ld trns_stat.#1
          ld data_cntr.#21
          ld save_ptr.#0
15        ld send_ptr.#0
          sbit eti,enui
          jmp end_d_s d_s1:  ifeq data_cntr,#10
20        ld save_ptr,#0
          ld a,#11
          ifgt a,data_cntr
          jmp d_s2

25        ld b,#flags1        ; load data to stack.
          ld a,[b-]           ; flags1
          push a
          ld a,[b-]           ; pls_y1
          push a
30        ld a,[b-]           ; pls_y0
          push a
          ld a,[b-]           ; pls_x1
          push a
          ld a,[b-]           ; pls_x0
35        push a
          ld a,[b-]           ; hall2
          push a
          ld a,[b-]           ; hall1
          push a
40        ld a,[b-]           ; current2
          push a
          ld a,[b-]           ; current1
          push a
          ld a,save_ptr       ; save data from stack.
45        x a,b
```

```
ld a,b
x a,x
ld s,#1
pop a
x a,[b+]
pop a
x a,[b+]
pop a
x a,[b+]
pop a
x a,[b+]
pop a
x a,[b+]
pop a
x a,[b+]
pop a
x a,[b+]
pop a
x a,[b+]
pop a
x a,[b+]
ld a,t_check    ; compute check sum.
x a,b
ld a,[x+]       ; b=t_check, a = current1
add a,b         ; a = current1 + b
x a,b           ; b = a
ld a,[x+]
add a,b
x a,b
ld a,[x+]
add a,b
x a,b
ld a,[x+]
add a,b
x a,b
ld a,[x+]
add a,b
x a,b
ld a,[x+]
add a,b
x a,b
ld a,[x+]
add a,b
x a,b
ld a,[x+]
```

```
        add a,b
        x a,b
        ld a,[x+]    ; a = flags1
        add a,b      ; a = flags1 + b ld s,#0      ; t_check = a
        x a,t_check
        ld a,x
        x a,save_ptr jmp end_d_s d_s2:   ld b,#flags1  ; load data to stack.
        ld a,[b-]
        push a
        ld a,[b-]
        push a
        ld a,[b-]
        push a
        ld a,[b-]
        push a
        ld a,[b-]
        push a
        ld a,[b-]
        push a
        ld a,[b-]
        push a
        ld a,[b-]
        push a
        ld a,[b-]
        push a
        ld a,save_ptr  ; save data from stack.
        x a,b
        ld a,b
        x a,x
        ld s,#2
        pop a
        x a,[b+]
        pop a
        x a,[b+]
        pop a
        x a,[b+]
        pop a
        x a,[b+]
        pop a
```

```
              x a,[b+]
              pop a
              x a,[b+]
              pop a
        5     x a,[b+]
              pop a
              x a,[b+]
              pop a
              x a,[b+]
       10     ld a,t_check   ; compute check sum.
              x a,b
              ld a,[x+]      ; b=13, a = current1
              add a,b        ; a = current1 + b
              x a,b          ; b = a
       15     ld a,[x+]
              add a,b
              x a,b
              ld a,[x+]
              add a,b
       20     x a,b
              ld a,[x+]
              add a,b
              x a,b
              ld a,[x+]
       25     add a,b
              x a,b
              ld a,[x+]
              add a,b
              x a,b
       30     ld a,[x+]
              add a,b
              x a,b
              ld a,[x+]
              add a,b
       35     x a,b
              ld a,[x+]      ; a = flags1
              add a,b        ; a = flags1 + b ld s,#0        ; t_check = a
       40     x a,t_check
              ld a,x
              x a,save_ptr end_d_s:  ret
       45     ;***************************************************
```

```
        .sect a2d_converter.rom
        a2d00:  rbit a2den,flags2 ; the a2d prog. checks hall1+2 and current1+2
                ld enad,#082     ; c=>adch8=b0, 2=>psr=1=mclk divide by 16.
                sbit adbsy,enad
5       a2d01:  ifbit adbsy,enad
                jmp a2d01
                ld a,adrsth
                x a,hall1
                ld enad,#092     ; c=>adch9=b1, 2=>psr=1=mclk divide by 16.
10              sbit adbsy,enad
        a2d02:  ifbit adbsy,enad
                jmp a2d02
                ld a,adrsth
                x a,hall2
15              ld enad,#0a2     ; c=>adch10=b2, 2=>psr=1=mclk divide by 16.
                sbit adbsy,enad
        a2d03:  ifbit adbsy,enad
                jmp a2d03
                ld a,adrsth
20              x a,current1
                ld enad,#0b2     ; c=>adch11=b3, 2=>psr=1=mclk divide by 16.
                sbit adbsy,enad
        a2d04:  ifbit adbsy,enad
                jmp a2d04
25              ld a,adrsth
                x a,current2
                ret
        ;***********************************************************
        .sect velosity_caculation.rom
30
        v_calc: rbit en1_calc,lflags ld a,t_ref0
                x a,0
35              ld a,t_ref1
                x a,1 ld a,pthi
                ifgt a,1
40              jmp tooslow
                ld a,1
                ifgt a,pthi
                jmp toofast
                ld a,ptlo
45              ifgt a,0
```

```
        jmp tooslow
        ld a,0
        ifgt a,ptlo
        jmp toofast
 5      ret        ; if they are equal the speed is ok tooslow: sc         ; err= (pt - t_ref) => (4,5)
        ld a,ptlo   ; if t2ra + err*k >1000 then pwm=1000 (fastest)
        subc a,0
10      x a,4
        ld a,pthi
        subc a,1
        x a,5
        ld a,t2ralo
15      x a,2
        ld a,t2rahi
        x a,3
        jsr mybyk
        ld a,0
20      x a,2
        ld a,1
        x a,3
        ld a,4
        x a,0
25      ld a,5
        x a,1
        jmp end_v_calc toofast: sc         ; err= (t_ref - pt) => (4,5)
30      ld a,0      ; if t2rb + err*k >1000 then pwm=0 (slowest)
        subc a,ptlo
        x a,4
        ld a,1
        subc a,pthi
35      x a,5
        ld a,t2rblo
        x a,2
        ld a,t2rbhi
        x a,3
40      jsr mybyk
        ld a,4
        x a,2
        ld a,5
        x a,3
45
```

```
end_v_calc: ld b,#t2ralo
            ld x,#0
        ;   ld a,#1
        ;   ld tmr2hi,#2
     5  ;loop2:  ifgt a,tmr2hi
        ;   jp loop2
            ld a,[x+]
            x a,[b+]
            ld a,[x+]
    10      x a,[b+]
            ld a,[x+]
            x a,[b+]
            ld a,[x]
            x a,[b]
    15      ret
        ;***********************************************************
        v2_calc: rbit en1_calc2,aflags ld a,at_ref0
    20      x a,0
            ld a,at_ref1
            x a,1 ld a,apthi
    25      ifgt a,1
            jmp atooslow
            ld a,1
            ifgt a,apthi
            jmp atoofast
    30      ld a,aptlo
            ifgt a,0
            jmp atooslow
            ld a,0
            ifgt a,aptlo
    35      jmp atoofast
            ret         ; if they are equal the speed is ok atooslow:  sc       ; err= (pt2 - at_ref) => (4,5)
            ld a,aptlo      ; if t3ra + err*k >1000 then pwm=1000 (fastest)
    40      subc a,0
            x a,4
            ld a,apthi
            subc a,1
            x a,5
    45      ld a,t3ralo
```

```
                x a,2
                ld a,t3rahi
                x a,3
                jsr mybyk
5               ld a,0
                x a,2
                ld a,1
                x a,3
                ld a,4
10              x a,0
                ld a,5
                x a,1
                jmp end_v2_calc 15      atoofast: sc        ; err= (at_ref - pt2) => (4,5)
                ld a,0      ; if t3rb + err*k >1000 then pwm=0 (slowest)
                subc a,aptlo
                x a,4
                ld a,1
20              subc a,apthi
                x a,5
                ld a,t3rblo
                x a,2
                ld a,t3rbhi
25              x a,3
                jsr mybyk
                ld a,4
                x a,2
                ld a,5
30              x a,3 end_v2_calc:ld b,#t3ralo
                ld x,#0
35      ;       ld a,#1
        ;       ld tmr3hi,#2
        ;loop3: ifgt a,tmr3hi
        ;       jp loop3
                ld a,[x+]
40              x a,[b+]
                ld a,[x+]
                x a,[b+]
                ld a,[x+]
                x a,[b+]
45              ld a,[x]
```

```
        x a,[b]
        ret
;*********************************************************
        .sect math_functions,rom mybyk:  ld cntr,#6   ; div. by 64 (=2^6)
dvby2:  rc
        ld a,5
        rrc a
        x a,5
        ld a,4
        rrc a
        x a,4
        drsz cntr
        jmp dvby2
        rc           ; 4.5 <- err*k + t2
        ld a,4
        adc a,2
        x a,4
        ld a,5
        adc a,3
        x a,5 ifeq 5,#0
        jmp lowedge
        ld a,5
        ifgt a,#high(980)
        jmp highedge
        ld a,#high(980)
        ifgt a,5
        jmp end_mybyk  ; not edge
        ld a,4
        ifgt a,#low(980)
        jmp highedge jmp end_mybyk  ; not edge highedge:  ld 4,#low(980)
        ld 5,#high(980)
        ld 0,#20
        ld 1,#0
        ret lowedge:   ld a,4
        ifgt a,#20
```

```
            jmp end_mybyk
            ld 0,#low(980)
            ld 1,#high(980)
            ld 4,#20
 5          ld 5,#0
            ret end_mybyk:sc
            ld a,#low(1000)
10          subc a,4
            x a,0
            ld a,#high(1000)
            subc a,5
            x a,1
15          ld a,1
            ifgt a,#0
            ret
            ld a,0
            ifgt a,#20
20          ret
            ld 0,#20
            ld 4,#low(980)
            ld 5,#high(980)
            ret
25

;****** FDV168 - Fast 16 by 8 division subroutine ******************
; 490 instruction cycles maximum - 245usec.
; dividend in [1,0] (dd)      divisor in [3] (dr)
; quotient in [1,0] (quot)    remainder in [2] (test field)
30 fdv168: ld cntr,#16  ; load cntr with length of dividend field.
            ld 2,#0          ; clear test field.
        fd168s: ld b,#0
        fd168l: rc
35          ld a,[b]
            adc a,[b]        ; left shift dividend lo
            x a,[b+]
            ld a,[b]
            adc a,[b]        ; left shift dividend hi
40          x a,[b+]
            ld a,[b]
            adc a,[b]        ; left shift test field
            x a,[b]
            ld a,[b+]        ; test field to acc
45          ifc              ; test if bit shiefted out of test field****
```

```
          jp fd168b
          sc
          subc a,[b]    ; test subtract divisor from test field
          ifnc          ; test if borrow from subtraction
          jp fd168t
fd168r:   ld b,#2       ; subtraction result to test field
          x a,[b]
          ld b,#0
          sbit 0,[b]    ; set quotient bit
          drsz cntr     ; dectement and test cntr for zero
          jp fd168l
          ret           ; return from subroutine
fd168t:   drsz cntr     ; dectement and test cntr for zero
          jp fd168s
          ret           ; return from subroutine
fd168b:   subc a,[b]    ; subtract divisor from test field***
          jp fd168r
;******* BINDEC - Binary to Decimal (packed BCD) *********************
bindec:   ld cntr,#8    ; Bindec - Binary to Decimal (packed BCD)
          rc            ; 856 cycles * 0.5 ~ 428 cycles = 213usec.
          ld b,#1       ; binary in 0 => decinmal in 1,2
bd1:      ld [b+],#0
          ifbne #3
          jmp bd1
bd2:      ld b,#0
bd3:      ld a,[b]
          adc a,[b]
          x a,[b+]
          ifbne #1
          jmp bd3
bd4:      ld a,[b]
          add a,#066
          adc a,[b]
          dcor a
          x a,[b+]
          ifbne #3
          jmp bd4
          drsz cntr
          jmp bd2
          ret
;*********************************************
          .sect lcd_update,rom
updatelcd:ifbit lcdupdate,flags2
          jmp updatelcd0
          ifeq lcd_flags,#0
```

```
                ret
                jmp updatelcd4 updatelcd0:rbit lcdupdate,flags2
 5              ld lcd_cntr,#50
                ld a,pls_x0
                x a,0
                ld a,pls_x1
                x a,1
10              ld a,#lpulsepermm   ; linear pulses per mm
                x a,3
                jsr fdv168          ; mm = pls_x/linear_pulses_per_mm
                jsr bindec 15              ld pd,#080          ; cursor home - address 0.
                jsr lcd_com
                ld a,2
                and a,#0f
                add a,#'0'
20              x a,pd
                jsr lcd_dat
                ld a,1
                swap a
                and a,#0f
25              add a,#'0'
                x a,pd
                jsr lcd_dat
                ld a,1
                and a,#0f
30              add a,#'0'
                x a,pd
                jsr lcd_dat ld pd,#085          ; cursor address 5.
35              jsr lcd_com
                ifbit epi,flags1
                jmp updatelcd5 ifbit 7,pls_y1
40              jmp updatelcd1
                sc                  ; angel= - 08000-pls_y
                ld a,#0
                subc a,pls_y0
                x a,0
45              ld a,#080
```

```
            subc a,pls_y1
            x a,1
            ld pd,#'-'
            jmp updatelcd2
 5  updatelcd1:ld a,pls_y1        ; angel= + pls_y-08000
            and a,#07f
            x a,1
            ld a,pls_y0
            x a,0
10          ld pd,#'+' updatelcd2:jsr lcd_dat
            ld cntr,#3
    updatelcd3:rc
15          ld a,1
            rrc a
            x a,1
            ld a,0
            rrc a
20          x a,0
            drsz cntr
            jmp updatelcd3
            ld 1,#0
            jsr bindec
25          ld a,1
            swap a
            and a,#0f
            add a,#'0'
            x a,pd
30          jsr lcd_dat
            ld a,1
            and a,#0f
            add a,#'0'
            x a,pd
35          jsr lcd_dat
            jmp updatelcd4
    updatelcd5:ld pd,#'e'
            jsr lcd_dat
            ld pd,#'p'
40          jsr lcd_dat
            ld pd,#'i'
            jsr lcd_dat updatelcd4:ifeq lcd_flags,#0
45          ret
```

```
        ifbit self_t_command,buttons_flags
        ld lcd_flags,#0
        ifbit start_stop,buttons_flags
        ld lcd_flags,#0
 5      ifeq lcd_flags,#0
        ret ifbit type_start,lcd_flags
        ld temp,#low(wordstart); type 'start' at line 2 of lcd.
10      ifbit type_end,lcd_flags
        ld temp,#low(wordend)
        ifbit type_Stuck,lcd_flags
        ld temp,#low(wordstuck)
        ifbit type_stop,lcd_flags
15      ld temp,#low(wordstop)

jsr type_string1
        ld lcd_flags,#0

20
   end_updatelcd:ret

;*******************************************
   .sect lcd_orders,rom
25 clean_lcd:ld pd,#01
        jsr lcd_com
        jmp del16
   ;    ret
   ;*****************************************
30 type_string0:ld pd,#080      ; type string from the start of line 0.
        jsr lcd_com
        jmp type_string
   type_string1:ld pd,#0c0      ; type string from the start of line 0.
        jsr lcd_com
35 type_string:ld a,temp
        inc a
        x a,temp
        jsr get_char
        ifeq a,#'@'
40      ret
        x a,pd
        jsr lcd_dat
        jmp type_string 45 ;********  subrutine to initialize lcd display
```

```
init_lcd:  ld a,#10
init_lcd1: jsr del16
           dec a
           ifne a,#0
           jp init_lcd1 init_lcd2: ld pd,#01   ;display clear
           jsr lcd_com
           jsr del16 ld pd,#06   ;increment cursor (cursor moves: left to right)
           jsr lcd_com ld pd,#0c   ;display on , cursor off
           jsr lcd_com ld pd,#03f  ;8 bits
        ;  jmp lcd_com ;  ret
;********** subrutine to transfer command to lcd display
lcd_com:   rbit rs,pa ;command
end_com_dat:
           sbit cs_lcd,pa
           rbit cs_lcd,pa
           ld cntr,#10
loop1:     drsz cntr
           jp loop1
           ret
;********** subrutine to transfer data to lcd display
lcd_dat:   sbit rs,pa ;command
           jmp end_com_dat ;***** delay ************* del16:     ld cntr,#2
del160:    ld temp,#250 ;1.6 msec delay
del161:    drsz temp
           jmp del161
           ld temp,#150
del162:    drsz temp
           jmp del162
           drsz cntr
           jmp del160
           ret
```

```
;*******************************
.sect string_table.rom.inpage
get_char:laid
        ret
;**** ascii table *******************
wordmm:      .db ' mm  @'
wordstart:  .db 'start @'
wordstop:    .db 'stop  @'
wordpoweron:.db 'power on@'
wordhome:    .db 'home  @'
wordstuck: .db 'stuck  @'
wordend:     .db 'end   @'
wordbottom:  .db 'bottom @'
wordready:.db 'ready  @'
wordselftest:   .db 'selftest@'
wordautorun:  .db 'autorun @'
wordinplace:    .db 'in place@'

.endsect

.END 0
            ;end of program listing of intumed.asm
```

Appendix 2

; This is c8cdr.inc
;*************************************************************
; ****
       ; This file include cop8cdr.inc, cop8.inc, cop8c3r.inc, 8cdr.chp, ports.inc(shortcuts).

;port definitions in cop8 with flash.

ped   =090    ; port e data (output); pe is already taken by parity enable.
         pec   =091    ; port e configuration
         pei   =092    ; port e input pf =094       ; port f data (output)
         pfc   =095    ; port f configuration
         pfi=096       ; port f input pa =0a0       ; port a data (output)
         pac   =0a1    ; port a configuration
         pai   =0a2    ; port a input pb =0a4       ; port b data (output)
         pbc   =0a5    ; port b configuration
         pbi   =0a6    ; port b input pl =0d0       ; port l data (output)
         plc   =0d1    ; port l configuration
         pli=0d2       ; port l input pg =0d4       ; port g data (output)
         pgc   =0d5    ; port g configuration
         pgi   =0d6    ; port g input pc =0d8       ; port c data (output)
         pcc   =0d9    ; port c configuration
         pci   =0da    ; port c input pd =0dc       ; port d data (output)

```
; This is cop8.inc
;***********************************************************
*********/
;* Primary Chip Names with Designators
;***********************************************************
*********/
ANYCOP   = 0
COP912C  = 1     ; Basic Family
COP820   = 2
COP840   = 3
COP880   = 4
COP820CJ = 5
COP840CJ = 6
COP8620  = 7
COP8640  = 8
COP8720  = 9
COP8780  = 10
COP943   = 11

COP888CF = 20    ; Feature Family
COP888CG = 21
COP888CL = 22
COP888CS = 23
COP888EG = 24
COP888EK = 25
COP8ACC  = 26
COP888BC = 27
COP888EB = 28
COP888EW = 29
COP888FH = 30
COP888GD = 31
COP888GG = 32
COP888GW = 33
COP888HG = 34
COP888KG = 35
COP8SAA  = 36
COP8SAB  = 37
COP8SAC  = 38
COP8SGR  = 39
COP8SGE  = 40
COP8SEC  = 41
COP8SER  = 42
COP8AJC  = 43
```

```
COP8AKC  = 44

;--------------- Flash based devices from here on
COP8CBR  = 60
COP8CCR  = 61
COP8CDR  = 62
COP8SBR  = 63
COP8SCR  = 64
COP8SDR  = 65

COPy8 = 99
;
; ---------------- End of COP8.INC ----------------------------------

;***********************************************************
        COPCHIP = COP8CDR      ; Chip Definition ; This is cop8C3R.inc
;
; PLEASE: Consider update for CBR,CDR, and CCR.
;
; Predeclare I/O and control registers frequently used by COP8 programmer.
.macro   setopt
.mloc sec,wd,halt,flex
;
.ifb   @1    ; if null
sec    = 0   ; default value (not secure)
.else
sec    = @1
.endif
.ifb   @2    ; if null
wd     = 0   ; default value (Watchdog enabled)
.else
wd     = @2
.endif
.ifb   @3    ; if null
halt   = 0   ; default value (HALT enabled)
.else
halt   = @3
.endif
.ifb   @4    ; if null
flex   = 1   ; default value (Execute from Flash)
.else
```

```
           flex  =  @4
       .endif

.sect OPTION, CONF
CONFIG:    .db   ((sec shl 3 or wd) shl 1 or halt) shl 1 or flex
       .endm ; ---------------- End of setecon Macro Definition --------------------
;
; ----------------------------------------------------------------
; SFR Names and Register Bit Names Agree with the Feature Family User's
; Manual Redundant names match corresponding functions on Basic Family
; Documentation
;

PORTED  =  0x90:BYTE       ; Port E Data
       PORTEC  =  0x91:BYTE       ; Port E Configuration
       PORTEP  =  0x92:BYTE       ; Port E input pins (read only)
   ;
       PORTFD  =  0x94:BYTE       ; Port F Data
       PORTFC  =  0x95:BYTE       ; Port F Configuration
       PORTFP  =  0x96:BYTE       ; Port F input pins (read only)
   ;
       PORTAD  =  0xA0:BYTE       ; Port A Data
       PORTAC  =  0xA1:BYTE       ; Port A Configuration
       PORTAP  =  0xA2:BYTE       ; Port A input pins (read only)
   ;
       PORTBD  =  0xA4:BYTE       ; Port B Data
       PORTBC  =  0xA5:BYTE       ; Port B Configuration
       PORTBP  =  0xA6:BYTE       ; Port B input pins (read only)
   ;
ISPADLO  =  0xA8:BYTE       ; ISP Address Register Low Byte
ISPADHI  =  0xA9:BYTE       ; ISP Address Register High Byte
ISPRD    =  0xAA:BYTE       ; ISP Read Data Register
ISPWR    =  0xAB:BYTE       ; ISP Write Data Register
   ;
TINTA    =  0xAD:BYTE       ; High Speed Timers Interrupt A
TINTB    =  0xAE:BYTE       ; High Speed Timers Interrupt B
HSTCR    =  0xAF:BYTE       ; High Speed Timers Control Register
   ;
       TMR3LO  =  0xB0:BYTE       ; Timer 3 low byte
       TMR3HI  =  0xB1:BYTE       ; Timer 3 high byte
       T3RALO  =  0xB2:BYTE       ; Timer 3 RA register low byte
       T3RAHI  =  0xB3:BYTE       ; Timer 3 RA register high byte
       T3RBLO  =  0xB4:BYTE       ; Timer 3 RB register low byte
```

```
        T3RBHI  =  0xB5:BYTE       ; Timer 3 RB register high byte
        T3CNTRL=  0xB6:BYTE         ; Timer 3 control register
    ;
        TBUF  =  0xB8:BYTE          ; UART transmit buffer
        RBUF  =  0xB9:BYTE          ; UART receive buffer
        ENU   =  0xBA:BYTE          ; UART control and status register
        ENUR  =  0xBB:BYTE          ; UART receive control and status reg.
        ENUI  =  0xBC:BYTE          ; UART interrupt and clock source reg.
        BAUD  =  0xBD:BYTE          ; BAUD register
        PSR   =  0xBE:BYTE         ; UART prescaler select register
    ;
        TMR2LO  =  0xC0:BYTE        ; Timer 2 low byte
        TMR2HI  =  0xC1:BYTE        ; Timer 2 high byte
        T2RALO  =  0xC2:BYTE        ; Timer 2 RA register low byte
        T2RAHI  =  0xC3:BYTE        ; Timer 2 RA register high byte
        T2RBLO  =  0xC4:BYTE        ; Timer 2 RB register low byte
        T2RBHI  =  0xC5:BYTE        ; Timer 2 RB register high byte
        T2CNTRL=  0xC6:BYTE         ; Timer 2 control register
    ;
        WDSVR  =  0xC7:BYTE        ; Watch dog service register
    ;
        WKEDG  =  0xC8:BYTE        ; MIWU edge select register
        WKEN   =  0xC9:BYTE        ; MIWU enable register
      . WKPND  =  0xCA:BYTE        ; MIWU pending register
    ;
ENAD  =  0xCB:BYTE       ; A/D Converter Control register
ADRSTH  =  0xCC:BYTE     ; A/D Converter Result Register High Byte
ADRSTL  =  0xCD:BYTE     ; A/D Converter Result Register Low Byte
    ;
ITMR  =  0xCF:BYTE       ; Idle Timer Control Register
    ;
        PORTLD  =  0xD0:BYTE       ; Port L data
        PORTLC  =  0xD1:BYTE       ; Port L configuration
        PORTLP  =  0xD2:BYTE       ; Port L pin
    ;
        PORTGD  =  0xD4:BYTE       ; Port G data
        PORTGC  =  0xD5:BYTE       ; Port G configuration
        PORTGP  =  0xD6:BYTE       ; Port G pin
    ;
        PORTCD  =  0xD8:BYTE       ; Port C data
        PORTCC  =  0xD9:BYTE       ; Port C configuration
        PORTCP  =  0xDA:BYTE       ; Port C pin
    ;
        PORTD  =  0xDC:BYTE        ; Port D
    ;
```

```
        PGMTIM  =  0xE1:BYTE     ; E2 and Flash Write Timing Register
        ISPKEY  =  0xE2:BYTE     ; ISP Key Register
        ;
            T1RBLO  =  0xE6:BYTE    ; Timer 1 RB register low byte
            T1RBHI  =  0xE7:BYTE    ; Timer 1 RB register high byte
        ;
            ICNTRL  =  0xE8:BYTE    ; Interrupt control register
        ;
            SIOR    =  0xE9:BYTE    ; SIO shift register
            SIO     =  0xE9:BYTE    ; SIO shift register
        ;
            TMR1LO  =  0xEA:BYTE    ; Timer 1 low byte
            TMR1HI  =  0xEB:BYTE    ; Timer 1 high byte
            T1RALO  =  0xEC:BYTE    ; Timer 1 RA register low byte
            T1RAHI  =  0xED:BYTE    ; Timer 1 RA register high byte
        ;
            CNTRL   =  0xEE:BYTE    ; control register
            PSW     =  0xEF:BYTE    ; PSW register
        ;
        BYTECOUNTLO =  0xF1:BYTE    ; When JSRB Boot Rom used
        ;
            S       =  0xFF:BYTE    ; Segment register, only COP888CG/CS!
        ;

;------------------------------------------------------------------
; Bit Constant Declarations.
;
;----- Alternate function bit definitions on port G INT     =  0       ; Interrupt input
            INTR    =  0       ; Interrupt input
            WDOUT   =  1       ; Watchdog output
            T1B     =  2       ; Timer T1B output
            T1A     =  3       ; Timer T1A output
            SO      =  4       ; Seriell output
            SK      =  5       ; Seriell clock
            SI      =  6       ; Seriell input
            CKO     =  7       ; Halt,restart input
        ;
;----- Alternate function bit definitions on port L
            CKX     =  1       ; ext. clock I/O-pin/UART
            TDX     =  2       ; transmit data/UART
            RDX     =  3       ; receive data/UART
            T2A     =  4       ; Timer T2A output
            T2B     =  5       ; Timer T2B output
```

```
T3A    = 6         ; Timer T3A output
T3B    = 7         ; Timer T3B output
;
:     Alternate function bit definitions on port A
ACH0   = 0         ; A/D-Channel 0
ACH1   = 1         ; A/D-Channel 1
ACH2   = 2         ; A/D-Channel 2
ACH3   = 3         ; A/D-Channel 3
ACH4   = 4         ; A/D-Channel 4
ACH5   = 5         ; A/D-Channel 5
ACH6   = 6         ; A/D-Channel 6
ACH7   = 7         ; A/D-Channel 7
;
;     Alternate function bit definitions on port B
ACH8   = 0         ; A/D-Channel 8
ACH9   = 1         ; A/D-Channel 9
ACH10  = 2         ; A/D-Channel 10
ACH11  = 3         ; A/D-Channel 11
ACH12  = 4         ; A/D-Channel 12
ACH13  = 5         ; A/D-Channel 13
MUXOUTN = 5        ; A/D Mux Negative Output
ACH14  = 6         ; A/D-Channel 14
MUXOUTP = 5        ; A/D Mux Positive Output
ACH15  = 7         ; A/D-Channel 15
ADIN   = 7         ; A/D Converter Input
;
;----- Bit definitions CNTRL register
T1C3   = 7         ; Timer 1 mode control
TC1    = T1C3      ; COP880/840/820 control signal name
T1C2   = 6         ; Timer 1 mode control
TC2    = T1C2      ; COP880/840/820 control signal name
T1C1   = 5         ; Timer 1 mode control
TC3    = T1C1      ; COP880/840/820 control signal name
T1C0   = 4         ; Start/Stop timer in modes 1 and 2
                   ; Underflow interrupt pending in mode 3
TRUN   = T1C0      ; COP880/840/820 control signal name
MSEL   = 3         ; Enable Microwire
IEDG   = 2         ; Selects external interr. edge polarity
SL1    = 1         ; Microwire clock divide select
SL0    = 0         ; Microwire clock divide select
;
;----- Bit definitions PSW register
HC     = 7         ; Half Historical Redundant carry flag
C      = 6         ; Carry flag
T1PNDA = 5         ; Timer T1A interrupt pending
```

```
        TPND  = T1PNDA    ; Historical Redundant
        T1ENA = 4         ; Timer T1A interrupt enable
        ENTI  = T1ENA     ; Historical Redundant
        EXPND = 3         ; External interrupt pending
        IPND  = EXPND     ; Historical Redundant
        BUSY  = 2         ; Microwire busy shifting
        EXEN  = 1         ; External interurpt enable
        ENI   = EXEN      ; Historical Redundant
        GIE   = 0         ; Global interr. enable
        ;
        ;----- Bit definitions ICNTRL register
        LPEN    = 6       ; L-Port interr. enable
        T0PND   = 5       ; Timer T0 interr. pending
        T0EN    = 4       ; Timer T0 interr. enable
        WPND    = 3       ; Microwire interr. pending
        WEN     = 2       ; Microwire interr. enable
        T1PNDB  = 1       ; Timer T1B interr. pending flag
        T1ENB   = 0       ; Timer T1B interr. enable
        ;
        ;----- Bit definitions T2CNTRL register
        T2C3    = 7       ; Timer T2 mode control
        T2C2    = 6       ; Timer T2 mode control
        T2C1    = 5       ; Timer T2 mode control
        T2C0    = 4       ; Timer T2A start/stop
        T2PNDA  = 3       ; Timer T2A interr. pending flag
        T2ENA   = 2       ; Timer T2A interr. enable
        T2PNDB  = 1       ; Timer T2B interr. pending flag
        T2ENB   = 0       ; Timer T2B interr. enable
        ;
        ;----- Bit definitions T3CNTRL register
        T3C3    = 7       ; Timer T3 mode control
        T3C2    = 6       ; Timer T3 mode control
        T3C1    = 5       ; Timer T3 mode control
        T3C0    = 4       ; Timer T3A start/stop
        T3PNDA  = 3       ; Timer T3A interr. pending flag
        T3ENA   = 2       ; Timer T3A interr. enable
        T3PNDB  = 1       ; Timer T3B interr. pending flag
        T3ENB   = 0       ; Timer T3B interr. enable
        ;
        ;    Bit definitions HSTCR register
        T9HS    = 7       ; Timer T9 High Speed Enable
        T8HS    = 6       ; Timer T8 High Speed Enable
        T7HS    = 5       ; Timer T7 High Speed Enable
        T6HS    = 4       ; Timer T6 High Speed Enable
        T5HS    = 3       : Timer T5 High Speed Enable
```

```
T4HS   = 2        ; Timer T4 High Speed Enable
T3HS   = 1        ; Timer T3 High Speed Enable
T2HS   = 0        ; Timer T2 High Speed Enable
;
;      Bit definitions TINTA register
T9INTA= 7         ; Timer 9 Interrupt A
T8INTA= 6         ; Timer 8 Interrupt A
T7INTA= 5         ; Timer 7 Interrupt A
T6INTA= 4         ; Timer 6 Interrupt A
T5INTA= 3         ; Timer 5 Interrupt A
T4INTA= 2         ; Timer 4 Interrupt A
T3INTA= 1         ; Timer 3 Interrupt A
;
;      Bit definitions TINTB register
T9INTB= 7         ; Timer 9 Interrupt B
T8INTB= 6         ; Timer 8 Interrupt B
T7INTB= 5         ; Timer 7 Interrupt B
T6INTB= 4         ; Timer 6 Interrupt B
T5INTB= 3         ; Timer 5 Interrupt B
T4INTB= 2         ; Timer 4 Interrupt B
T3INTB= 1         ; Timer 3 Interrupt B
;
;      Bit definitions ENAD register
       ADCH3 = 7      ; A/D Convertor Channel Select bit 3
ADCH2 = 6              ; A/D Convertor Channel Select bit 2
       ADCH1 = 5       ; A/D Convertor Channel Select bit 1
       ADCH0 = 4       ; A/D Convertor Channel Select bit 0
       ADMOD= 3        ; A/D Convertor Mode Select bit
ADMUX  = 2         ; A/D Mux Out Control
       PSC  = 1        ; A/D Convertor Prescale Select bit
ADBSY= 0           ; A/D Convertor Busy Bit
;
;----- Bit definitions ENU register
       PEN   = 7       ; Parity enable
       PSEL1 = 6       ; Parity select
       PSEL0 = 5       ; Parity select
       XBIT9 = 5       ; 9th transmission bit in 9bit data mode
       CHL1  = 4       ; Select character frame format
       CHL0  = 3       ; Select character frame format
       ERR   = 2       ; Error flag
       RBFL  = 1       ; Received character
       TBMT  = 0       ; Transmited character
;
;----- Bit definitions ENUR register
       DOE   = 7       ; Data overrun error
```

```
        FE    = 6        ; Framing error
        PE    = 5        ; Parity error
        BD    = 4        ; Break Detect
        RBIT9 = 3        ; Contains the ninth bit (nine bit frame!)
        ATTN  = 2        ; Attention mode
        XMTG  = 1        ; indicate transmitting mode
        RCVG  = 0        ; indicate framing error
;
;----- Bit definition ENUI register
        STP2  = 7        ; Select number of stop bits
        BRK   = 6        ; Holds TDX low to Generate a BREAK
        ETDX  = 5        ; Select transmit-pin 12
        SSEL  = 4        ; Select UART-mode
        XRCLK = 3        ; Select clock source for the receiver
        XTCLK = 2        ; Select clock source for the transmitter
        ERI   = 1        ; Enable interr. from the receiver
        ETI   = 0        ; enable interr. from the transmitter
;
;  Bit Definitions for ITMR Register
        LSON   = 7       ; Low Speed Oscillator Enable
        HSON   = 6       ; High Speed Oscillator Enable
        DCEN   = 5       ; Dual Clock Enable - Switches T0 To
                         ; Low Speed Clock
        CCKSEL = 4       ; Core Clock Select - Switches Instr
                         ; Execution To Low Speed Clock
        ITSEL2 = 2       ; IDLE Timer Period Select bit 2
        ITSEL1 = 1       ; IDLE Timer Period Select bit 1
        ITSEL0 = 0       ; IDLE Timer Period Select bit 0
;
        KEY = 0x98 ; Required Value for ISP Key
;
;--------------- End of COP8C3R.INC ---------------------------------

;******************************************************************
*****
;This is 8cdr.chip .CHIP 8CDR       ; specifies max. ROM address 7FFF
                         ; RAM = 1K ;CHIP_SPEC (chip_table) for COP8CDR9xxxx parts
; PLEASE: Consider also update of files for CBR and CCR when modifying this file.

; 0 value if undefined, address value otherwise
```

```
mole     = 0
romsize  = 0x8000     ; ROM size
ramhi    = 0x6F       ; segment 0 high address
eelo     = 0          ; on-chip eerom range
eehi     = 0
t3lo     = 0xB0       ; timer 3 registers
t3hi     = 0xB6
comp     = 0          ; comparator
uartlo   = 0xB8       ; uart registers
uarthi   = 0xBE
t2lo     = 0xC0       ; timer 2 registers
t2hi     = 0xC6
wdog     = 0xC7       ; watch dog service register
miwulo   = 0xC8       ; miwu registers
miwuhi   = 0xCA
a2dlo    = 0xCB       ; a/d registers
a2dhi    = 0xCD
lportlo  = 0xD0       ; l port registers
lporthi  = 0xD2
gportlo  = 0xD4       ; g port registers
gporthi  = 0xD6
iport    = 0          ; i port
cportlo  = 0xD8       ; c port
cporthi  = 0xDA
dport    = 0xDC       ; d port
eecr     = 0          ; eerom control register
eromdr   = 0          ; eerom data register
eearlo   = 0          ; eerom address registers
eearhi   = 0
;icntrl  = 0xE8       ; icntrl register    ; already defined
microwire = 0xE9      ; uWire SIO
t1alo    = 0xE6       ; t1 auto ld t1rb
t1ahi    = 0xE7
t1blo    = 0xEA       ; t1 reg
t1bhi    = 0xED
;cntrl   = 0xEE       ; cntrl reg    ; already defined
;psw     = 0xEF       ; psw reg      ; already defined
rnlo     = 0xF0       ; RAM reg range
rnhi     = 0xFF
segramlo = 0x0100     ; segments low to high
segramhi = 0x077F
cntrl2   = 0
wdogctr  = 0
modrel   = 0
econ     = 0x7FFF     ; econ hex-file location
```

```
cfgsize  =  1           ; econ array cell address.

;family = 0 for basic family, family = 1 for feature family family   =  1
```

Appendix 3

```
;*********** Constants definitions ******************
       lpulsepermm=136    ; 16 * 22 / 2.54 = 138.58  = linear pulse per mm
 5     ;************ Register Definitions *****************
       f0      =0f0      ; not used
       uart_tmr =0f1     ; used as receive watch dog - when 0, return rec_stat(receiving state) to 0.
       rbyte_num =0f2    ; number of bytes to be received.
       tbyte_num =0f3    ; number of bytes to be transmitted.
10     temp    =0f4      ; used for temporary calculations as variable or counter.
       ;       =0f5      ; not used
       cntr    =0f6      ; used for temporary calculations as counter.
       lcd_cntr =0f7     ; used to refresh lcd every 0.1 sec (according to timer0 - 25*4msec)
       f8      =0f8      ; not used
15     data_cntr =0f9    ; used to count 20 data packets.
       fa      =0fa      ; not used
       fb      =0fb      ; not used
       ;********** bits definitions  *****************
       rs=2           ; pa      ; determines if the LCD gets command(0) or data(1).
20     cs_lcd=3       ; pa      ; send the information in the lcd data pins upon rise and fall(_/\_) of
       cs_lcd.
       control1=4 ; pa         ; \
       control2=5 ; pa         ; / control 1+2 determine the direction of motor 1
       control3=6 ; pa         ; \
25     control4=7 ; pa         ; / control 3+4 determine the direction of motor 2
       ;home_position=5; pl
       ;start_stop=7  ; pl
       home_limit=5 ; pb
       bottom_limit=6   ; pb
30     angular_limit=7; pb
       ;**********   flags *****************************************
       direction=0 : lflags   ; direction of motor 1
       first_pulse=1  ; lflags   ; if set then there was already 1 pulse.
       en_calc=2      ; lflags   ; enables calculation of time per pulse.
35     en1_calc=3 ; lflags    ; enables calculation of velocity every.
       stop1=4        ; lflags   ; signals that motor1 sould be stopped
       pulse=5        ; lflags   ; signals that there was a pulse from motor 1 direction2=0   : aflags   ; direction of motor 2
40     firsty_pulse=1; aflags    ; if set then there was already 1 pulse.
       en_calc2=2; aflags        ; enables calculation of time per pulse.
       en1_calc2=3    ; aflags   ; enables calculation of velocity every.
       stop2=4        ; aflags   ; signals that motor2 sould be stopped
       pulse2=5       ; aflags   ; signals that there was a pulse from motor 2
45
```

```
     start=0     ; flags1 ; 1 when start command is received, 0 when stop command is issued.
     home=1      ; flags1 ; 1 when home micro switch (Normally Closed) is closed, o when
                 open.
     bottom=2    ; flags1 ; 1 when bottoming micro switch (NO) is closed, o when open.
 5   epi=3       ; flags1 ; 1 when Epiglottis is sensed.
     stop=4      ; flags1 ; 1 when stop command is received, 0 when start command is issued.
     end=5       ; flags1 ; 1 when planned mission ends.
     stuck=6     ; flags1 ; 1 when a motor is stuck.
     enddata=7   ; flags1 ;   additional bit for the PC to know when the micro stops sending
10   data.

fix_t_en=0  ; flags2 ; generatl enable for saving and transmitting the blockes of data.
     fix_t_en1=1 ; flags2 ; enable 1 block saving, and set every 8msec by timer0.
     a2den=2     ; flags2 ; enables a/d
15   lcdupdate=3 ; flags2 ; being set every 0.1sec by timer 0 to refresh lcd.

type_start=0  ; lcd_flags ; if set lcd sould type "start" in line2.
     type_stop=1   ; lcd_flags ; if set lcd sould type "stop" in line2.
20   type_end=2;   lcd_flags ; if set lcd sould type "end" in line2.
     type_stuck=3  ; lcd_flags ; if set lcd sould type "stuck" in line2.

new_direction=3; rbyte1 ; the new direction for the motors as received from the pc.
     motor=4     ; rbyte1 ; 0 - motor1, 1 - motor2.
25 buttons_t_en=0      ; buttons_flags
     home_command=1      ; buttons_flags
     home_command_pc=2   ; buttons_flags
30   self_t_command=3    ; buttons_flags
     stop_command=4      ; buttons_flags
     home_position=5;    buttons_flags   + pl
     start_stop=7        ; buttons_flags   + pl 35   limits_c_en=0 ; limits_flags _____ to be shifted if it is the only bit in this
     byte.
     ;****** s=0 *******bytes definitions *************************
     lflags =020  ; flags that belongs to linear motor (motor1).
     aflags =021  ; flags that belongs to angular motor (motor2).
40   ang_stat =022  ; angular motor work states.
     nxt_a_stat=023  ; save the next ang_stat that come after a subroutine or an ang_stat.
     plsy_cntr0=024  ; lsb ; angular distance that motor 2 sould do in start command.
     plsy_cntr1=025  ; msb
     pls_cntr0 =026  ; lsb ; linear distance that motor 1 sould do in start command.
45   pls_cntr1 =027  ; msb
```

92

```
linear_stat =028    ; linear motor work states.
nxt_l_stat=029      ; save the next linear_stat that come after a subroutine or an linear_stat.
flags2   =02a       ; save flags of lcd, a/d and fix_t_en.
cd_dly   =02b       ; delay before changing direction to alow the motor to reach a complete
                      stop.
rec_stat =02c       ; usart receiving work state.
trns_stat=02d       ; usart transmitting work state.
int_cntr =02e       ; counter to help with timming. decreased by 1 every 4msec.

current1 =030       ; digital current from motor 1.
current2 =031       ; digital current from motor 2.
hall1    =032       ; digital hall senssor from motor 1.
hall2    =033       ; digital hall senssor from motor 2.
pls_x0   =034 ; lsb ; total linear distance in pulses.
pls_x1   =035       ; msb
pls_y0   =036 ; lsb ; total angular distance in pulses.
pls_y1   =037       ; msb
flags1   =038       ;
t_check  =039       ; check sum of 1 packet of 20 blocks of current1+...+flags1
check_sum =03a      ; check sum of received bytes in 1 command from the pc.
save_ptr =03b       ; pointer to show where the next byte should be saved in the packet of 20
                      blocks (s1,s2).
send_ptr =03c       ; pointer to show from where the next byte should be sent in the packet of
                      20 blocks (s1,s2).
zero_h1  =03d
zero_h2  =03e pt1lo =040    ; lsb ; save the capture time of motor 1 last pulse.       ; timer 1a
pt1hi =041    ; msb
pt2lo =042    ; lsb ; save the capture time of 1 pulse before motor 1 last pulse.
pt2hi =043    ; msb
ptlo  =044    ; lsb ; save the time between the last 2 pulses of motor 1. calculated in
                      timer0.
pthi  =045    ; msb
t_ref0 =046   ; lsb ; the desired time between pulses of motor 1 as received from the
                      pc.
t_ref1 =047   ; msb apt1lo =048   ; lsb ; save the capture time of motor 2 last pulse.       ; timer 1b
apt1hi =049   ; msb
apt2lo =04a   ; lsb ; save the capture time of 1 pulse before motor 2 last pulse.
apt2hi =04b   ; msb
aptlo  =04c   ; lsb ; save the time between the last 2 pulses of motor 2. calculated in
                      timer0.
apthi  =04d   ; msb
```

```
at_ref0  =04e   : lsb  : the desired time between pulses of motor 2 as received from the
                pc.
at_ref1  =04f   : msb receive_ptr=050 ; pointer where to store the byte that will be received next.
rbyte1   =051   ;
rbyte2   =052   ;   received bytes.
rbyte3   =053   ;
rbyte4   =054   ;
rbyte5   =055   ;
trns_ptr =056   ; pointer where the next byte to be transmitted is stored.
tbyte1   =057   ;
tbyte2   =058   ;   bytes to be transmitted.
tbyte3   =059   ;
tbyte4   =05a   ;
tbyte5   =05b   ;
tbyte6   =05c   ;
tbyte7   =05d   ;

packet_cntr=05f ; counts the packets that are send every 160msec untill the micro returns
                to work state 0.

limits_flags=060 ; micro(limit) switches - normally closed.
buttons_flags =061 ; buttons - normally closed.
ritut    =062 ; ritut - counter to prevent buttons vibrations, only 3sec push is considered a
              prese.
start_stop_cntr=063 ; counter of 3 sec.
home_position_cntr=064  ; counter of 3 sec.
selft_stat=065     ; work states of self test.
autorun_stat=066; work states of auto run.
lcd_flags=067     ; lcd flags - if set, something should be typed.
nolpulsetmr=068 : timer to turn off motor if no pulses received - assuming the motor is
                 stuck.
noapulsetmr=069
home_stat=06a      ; work states of home position.
```

The invention claimed is:

1. An automatically operative medical insertion device comprising:
   an insertable element which is adapted to be inserted within a living organism in vivo,
   a surface following element, physically associated with said insertable element and being arranged to follow a physical surface within said living organism in vivo;
   a driving subsystem operative to at least partially automatically direct said insertable element along said physical surface; and
   a navigation subsystem operative to control said driving subsystem based at least partially on a perceived location of said surface following element along a reference pathway stored in said navigation subsystem.

2. An automatically operative medical insertion device according to claim 1 and wherein said driving subsystem is operative to fully automatically direct said insertable element along said physical surface.

3. An automatically operative medical insertion device according to claim 1 and wherein said driving subsystem is operative to automatically and selectably direct said insertable element along said physical surface.

4. An automatically operative medical insertion device according to claim 1 and wherein said navigation subsystem receives surface characteristic information relating to said physical surface from said surface following element and employs said surface characteristic information to perceive the location of said surface following element along said reference pathway.

5. An automatically operative medical insertion device according to claim 4 and wherein said surface characteristic information comprises surface contour information.

6. An automatically operative medical insertion device according to claim 4 and wherein said surface characteristic information comprises surface hardness information.

7. An automatically operative medical insertion device according to claim 5 and wherein said surface contour information is three-dimensional.

8. An automatically operative medical insertion device according to claim 5 and wherein said surface contour information is two-dimensional.

9. An automatically operative medical insertion device according to claim 1 and wherein said insertable element is a endotracheal tube and wherein said physical surface comprises surfaces of the larynx and trachea.

10. An automatically operative medical insertion device according to claim 1 and wherein said insertable element is a gastroscope and wherein said physical surface comprises surfaces of the intestine.

11. An automatically operative medical insertion device according to claim 1 and wherein said insertable element is a catheter and wherein said physical surface comprises interior surfaces of the circulatory system.

12. An automatically operative medical insertion device according to claim 1 and also comprising a reference pathway generator operative to image at least a portion of said living organism and to generate said reference pathway based at least partially on an image generated thereby.

13. An automatically operative medical insertion device according to claim 1 and wherein said reference pathway comprises a standard contour map of a portion of the human anatomy.

14. An automatically operative medical insertion device according to claim 13 and wherein said standard contour map is precisely adapted to a specific patient.

15. An automatically operative medical insertion device according to claim 14 and wherein said standard contour map is automatically precisely adapted to a specific patient.

16. An automatically operative medical insertion device according to claim 1 and wherein said reference pathway is operator adaptable to designate at least one impediment.

17. An automatically operative medical insertion device according to claim 1 and wherein said insertable element comprises a housing in which is disposed said driving subsystem; a mouthpiece, a tube inserted through the mouthpiece and a flexible guide inserted through the tube, said surface following element being mounted at a front end of said guide.

18. An automatically operative medical insertion device according to claim 17 and wherein said mouthpiece comprises a curved pipe through which said tube is inserted.

19. An automatically operative medical insertion device according to claim 18 and wherein said driving subsystem is operative to move said guide in and out of said housing, through said curved pipe and through said tube.

20. An automatically operative medical insertion device according to claim 19 and wherein said driving subsystem is also operative to selectably bend a front end of said guide.

21. An automatically operative medical insertion device according to claim 18 and wherein said surface following element comprises a tip sensor including a tip integrally formed at one end of a short rod having a magnet on its other end, said rod extends through the center of a spring disk and is firmly connected thereto, said spring disk being mounted on one end of a cylinder whose other end is mounted on a front end of said insertable element.

22. An automatically operative medical insertion device according to claim 21 and wherein said tip sensor also comprises two Hall effect sensors which are mounted inside said cylinder on a support and in close proximity to said magnet, said Hall effect sensors being spaced in the plane of the curvature of the curved pipe, each Hall effect sensor having electrical terminals operative to provide electric current representing the distance of the magnet therefrom, said tip sensor being operative such that when a force is exerted on the tip along an axis of symmetry of said cylinder, said tip is pushed against said spring disk, causing said magnet to approach said Hall effect sensors and when a force is exerted on said tip sideways in the plane of said Hall effect sensors, said tip rotates around a location where said rod engages said spring disk causing said magnet to rotate away from one of said Hall effect sensors and closer to the other of the Hall effect sensors.

23. An automatically operative medical insertion device according to claim 22 and wherein said navigation subsystem is operative to measure the changes in the electrical outputs produced by the Hall effect sensors indicating the direction in which the tip is bent.

24. An automatically operative medical insertion device according to claim 23 and wherein said navigation subsystem is operative to sense the position of said tip and the past history of tip positions and to determine the location of said tip in said living organism and relative to said reference pathway.

25. An automatically operative medical insertion device according to claim 23 and wherein said navigation subsystem is operative to navigate said tip according to said reference pathway.

26. An automatically operative medical insertion device according to claim 25 and wherein said navigation subsystem is operative to sense that said tip touches the end of the trough beneath the epiglottis.

27. An automatically operative medical insertion device according to claim 23 and wherein said navigation subsystem is operative to sense that said tip reaches the tip of the epiglottis.

28. An automatically operative medical insertion device according to claim 23 and wherein said navigation subsystem is operative to sense that the tip reached the first cartilage of the trachea.

29. An automatically operative medical insertion device according to claim 28 and wherein said navigation subsystem is operative to sense that the tip reached the second cartilage of the trachea.

30. An automatically operative medical insertion device according to claim 29 and wherein said navigation subsystem is operative to sense that the tip reached the third cartilage of the trachea.

31. An automatically operative medical insertion device according to claim 17 and wherein said driving subsystem is operative, following partial insertion of said insertable element into the oral cavity, to cause the guide to extend in the direction of the trachea and bend the guide clockwise until said surface following element engages a surface of the tongue, whereby this engagement applies a force to said surface following element.

32. An automatically operative medical insertion device according to claim 17 and wherein said driving subsystem is operative to push said tube forward.

33. An automatically operative medical insertion device according to claim 17 and wherein said driving subsystem is operative to at least partially automatically direct said guide in a combined motion comprising a longitudinal motion and lateral motion.

34. An automatically operative medical insertion device according to claim 1 and wherein said driving subsystem is operative to move said insertable element in and out of said living organism.

35. An automatically operative medical insertion device according to claim 1 and wherein said driving subsystem is also operative to selectably bend a front end of said insertable element.

36. An automatically operative medical insertion device according to claim 1 and wherein said surface following element comprises a tactile sensing element.

37. An automatically operative medical insertion device according to claim 1 also comprising a memory and wherein said navigation subsystem is operative to load said reference pathway from said memory.

38. An automatically operative medical insertion device according to claim 1 and wherein said driving subsystem comprises: a first motor operative to selectably move said insertable element forward or backward; a second motor operative to selectably bend said insertable element; and electronic circuitry operative to control said first motor, said second motor and said surface following element.

39. An automatically operative medical insertion device according to claim 38 and wherein said electronic circuitry comprises a microprocessor operative to execute a program, said program operative to control said first and second motors and said surface following element and to insert and bend said insertable element inside said living organism along said reference pathway.

40. An automatically operative medical insertion device according to claim 38 and wherein said driving subsystem is operative to measure the electric current drawn by at least one of said first and second motors to evaluate the position of said surface following element.

41. An automatically operative medical insertion device according to claim 1 and wherein said reference pathway is operative to be at least partially prepared before an insertion process is activated.

42. An automatically operative medical insertion device according to claim 41 and wherein said medical insertion device comprises a medical imaging system and wherein said medical imaging system is operative to at least partially prepare said reference pathway.

43. An automatically operative medical insertion device according to claim 42 and wherein said medical imaging system comprises at least one of: an ultrasound scanner, an x-ray imager, a CAT scan system and an MRI system.

44. An automatically operative medical insertion device according to claim 42 and wherein said medical imaging system is operative to prepare said reference pathway by marking at least one contour of at least one organ of said living organism.

45. An automatically operative medical insertion device according to claim 42 and wherein said medical imaging system is operative to prepare said reference pathway by creating an insertion instruction table comprising at least one insertion instruction.

46. An automatically operative medical insertion device according to claim 45 and wherein said at least one insertion instruction comprises an instruction to at least one of extend, retract and bend said insertable element.

47. An automatically operative medical insertion device according to claim 45 and wherein said navigation subsystem is operative to control said driving subsystem based at least partially on a perceived location of said surface following element and according to said insertion instruction table.

48. An automatically operative medical insertion device according to claim 1 and wherein said operative medical insertion device is operative to at least partially store at least one log of a process of insertion of said insertable element.

49. An automatically operative medical insertion device according to claim 48 and wherein said medical insertion device comprises a computer and wherein said medical insertion device is operative to transmit said at least one log of a process of insertion of said insertable element.

50. An automatically operative medical insertion device according to claim 49 and wherein said computer is operative to aggregate said at least one log of a process of insertion of said insertable element.

51. An automatically operative medical insertion device according to claim 50 and wherein said computer is operative to prepare said reference pathway based at least partially on said aggregate.

52. An automatically operative medical insertion device according to claim 51 and wherein said computer transmits said reference pathway to said medical insertion device.

53. An automatically operative medical insertion device according to claim 1 and wherein said insertable element comprises a guiding element and a guided element.

54. An automatically operative medical insertion device according to claim 53 and wherein said driving subsystem is operative to direct said guiding element and said guided element at least partially together.

55. An automatically operative medical insertion device comprising:
   an insertable element which is adapted to be inserted within a living organism in vivo;
   a surface following element, physically associated with said insertable element and being arranged to follow a physical surface within said living organism in vivo;

a driving subsystem operative to at least partially automatically direct said insertable element along said physical surface; and a navigation subsystem operative to control said driving subsystem based at least partially on a perceived location of said surface following element along a reference pathway stored in said navigation subsystem, said insertable element comprising a disposable mouthpiece.

56. An automatically operative medical insertion method comprising:

inserting an insertable element within a living organism in vivo;

physically associating a surface following element with said insertable element and causing said surface following element to follow a physical surface within said living organism in vivo;

automatically and selectably directing said insertable element along said physical surface; and controlling direction of said insertable element based at least partially on a perceived location of said surface following element along a reference pathway stored in a navigation subsystem.

57. An automatically operative medical insertion method according to claim 56 and wherein said controlling comprises receiving surface characteristic information relating to said physical surface from said surface following element and employing said surface characteristic information to perceive the location of said surface following element along said reference pathway.

58. An automatically operative medical insertion method according to claim 57 and wherein said surface characteristic information comprises surface contour information.

59. An automatically operative medical insertion method according to claim 58 and wherein said surface contour information is three-dimensional.

60. An automatically operative medical insertion method according to claim 59 and wherein said automatically and selectably directing comprises automatically and selectably directing said insertable element in a combined motion comprising a longitudinal motion and a lateral motion.

61. An automatically operative medical insertion method according to claim 58 and wherein said surface contour information is two-dimensional.

62. An automatically operative medical insertion method according to claim 57 and wherein said surface characteristic information comprises surface hardness information.

63. An automatically operative medical insertion method according to claim 56 and wherein said insertable element is an endotracheal tube and wherein said physical surface comprises surfaces of the larynx and trachea.

64. An automatically operative medical insertion method according to claim 56 and wherein said insertable element is a gastroscope and wherein said physical surface comprises surfaces of the intestine.

65. An automatically operative medical insertion method according to claim 56 and wherein said insertable element is a catheter and wherein said physical surface comprises interior surfaces of the circulatory system.

66. An automatically operative medical insertion method according to claim 56 and also comprising generating said reference pathway based at least partially on an image generated by imaging at least a portion of said living organism.

67. An automatically operative medical insertion method according to claim 56 and also comprising generating said reference pathway based at least partially on a standard contour map of a portion of the human anatomy.

68. An automatically operative medical insertion method according to claim 67 and also comprising precisely adapting said standard contour map to a specific patient.

69. An automatically operative medical insertion method according to claim 68 and also comprising automatically precisely adapting said standard contour map to a specific patient.

70. An automatically operative medical insertion method according to claim 56 and also comprising adapting said reference pathway to designate at least one impediment.

71. An automatically operative medical insertion method according to claim 56 and also comprising:

mounting said surface following element at a front end of a flexible guide;

providing a housing in which is disposed a driving subsystem; a mouthpiece and a tube;

inserting said flexible guide through said tube;

inserting said tube through said mouthpiece; and driving said flexible guide employing said driving subsystem.

72. An automatically operative medical insertion method according to claim 71 and wherein said mouthpiece comprises a curved pipe through which said tube is inserted.

73. An automatically operative medical insertion method according to claim 72 and also comprising moving said guide in and out of said housing, through said curved pipe and through said tube employing said driving subsystem.

74. An automatically operative medical insertion method according to claim 73 and also comprising selectably bending a front end of said guide employing said driving subsystem.

75. An automatically operative medical insertion method according to claim 72 and wherein said physically associating a surface following element with said insertable element comprises integrally forming a tip at one end of a short rod having a magnet on its other end; extending said rod through the center of a spring disk; firmly connecting said spring disk to said rod; mounting said spring disk on one end of a cylinder; mounting another end of said cylinder on a front end of said insertable element.

76. An automatically operative medical insertion method according to claim 75 and wherein said surface following element also comprises two Hall effect sensors, each Hall effect sensor having electrical terminals operative to provide electric current representing the distance of the magnet therefrom and also comprising: mounting said Hall effect sensors inside said cylinder on a support and in close proximity to said magnet; spacing said Hall effect sensors in the plane of the curvature of the curved pipe; said tip being operative such that when a force is exerted on the tip along an axis of symmetry of said cylinder, said tip is pushed against said spring disk causing said magnet to approach said Hall effect sensors and when a force is exerted on said tip sideways in the plane of said Hall effect sensors, said tip rotates around a location where said rod engages said spring disk, causing said magnet to rotate away from one of said Hall effect sensors and closer to the other of the Hall effect sensors.

77. An automatically operative medical insertion method according to claim 76 and also comprising measuring the changes in the electrical outputs produced by the Hall effect sensors indicating the direction in which the tip is bent.

78. An automatically operative medical insertion method according to claim 77 and also comprising sensing the position of said tip and determining the location of said tip in said living organism and relative to said reference pathway based on the past history of tip positions.

79. An automatically operative medical insertion method according to claim 77 and also comprising navigating said tip according to said reference pathway employing said navigation subsystem.

80. An automatically operative medical insertion method according to claim 79 and also comprising sensing said tip touching the end of the trough beneath the epiglottis.

81. An automatically operative medical insertion method according to claim 77 and also comprising sensing said tip reaching the tip of the epiglottis.

82. An automatically operative medical insertion method according to claim 77 and also comprising sensing the tip reaching the first cartilage of the trachea.

83. An automatically operative medical insertion method according to claim 82 and also comprising sensing the tip reaching the second cartilage of the trachea.

84. An automatically operative medical insertion method according to claim 83 and also comprising sensing the tip reaching the third cartilage of the trachea.

85. An automatically operative medical insertion method according to claim 71 and also comprising moving said insertable element in and out of said living organism employing said driving subsystem.

86. An automatically operative medical insertion method according to claim 71 and also comprising:
   partially inserting said insertable element into the oral cavity;
   causing the insertable element to extend in the direction of the trachea; and
   bending the guide clockwise until said surface following element engages a surface of the tongue, whereby this engagement applies a force to said surface following element.

87. An automatically operative medical insertion method according to claim 71 and also comprising pushing said tube forward employing said driving subsystem.

88. An automatically operative medical insertion method according to claim 71 and wherein said driving subsystem comprises a first motor operative to selectably move said insertable element forward or backward and a second motor operative to selectably bend said insertable element, said method further comprising controlling said first motor, said second motor and said surface following element by employing electronic circuitry.

89. An automatically operative medical insertion method according to claim 88 and wherein said electronic circuitry comprises a microprocessor, said method also comprising executing a program, said executing a program comprising:
   controlling said first and second motors and said surface following element; and
   controlling insertion and bending of said insertable element inside said living organism along said reference pathway.

90. An automatically operative medical insertion method according to claim 88 and also comprising:
   measuring the electric current drawn by at least one of said first and second motors; and
   evaluating the position of said surface following element by employing said driving subsystem.

91. An automatically operative medical insertion method according to claim 71 and also comprising preparing said reference pathway by creating an insertion instruction table comprising at least one insertion instruction.

92. An automatically operative medical insertion method according to claim 91 and wherein said at least one insertion instruction comprises an instruction to at least one of extend, retract and bend said insertable element.

93. An automatically operative medical insertion method according to claim 91 and also comprising controlling said driving subsystem based at least partially on a perceived location of said surface following element and according to said insertion instruction table.

94. An automatically operative medical insertion method according to claim 71 and wherein said insertable element comprises a guiding element and a guided element.

95. An automatically operative medical insertion method according to claim 94 and wherein said driving subsystem is operative to direct said guiding element and said guided element at least partially together.

96. An automatically operative medical insertion method according to claim 56 and also comprising selectably bending a front end of said insertable element.

97. An automatically operative medical insertion method according to claim 56 and wherein said surface following element comprises a tactile sensing element.

98. An automatically operative medical insertion method according to claim 56 and also comprising loading said reference pathway from a memory to said navigation subsystem.

99. An automatically operative medical insertion method according to claim 56 and also comprising preparing said reference pathway at least partially before the insertion process is activated.

100. An automatically operative medical insertion method according to claim 99 and also comprising:
   providing a medical imaging system; and
   preparing said reference pathway at least partially by employing said medical imaging system.

101. An automatically operative medical insertion method according to claim 100 and wherein said medical imaging system comprises at least one of an ultrasound scanner, an x-ray imager, a CAT scan system and an MRI system.

102. An automatically operative medical insertion method according to claim 99 and also comprising preparing said reference pathway by marking at least one contour of at least one organ of said living organism.

103. An automatically operative medical insertion method according to claim 56 and also comprising storing at least partially at least one log of a process of insertion of said insertable element.

104. An automatically operative medical insertion method according to claim 103 and also comprising:
   providing a computer; and
   transmitting said at least one log of a process of insertion of said insertable element to said computer.

105. An automatically operative medical insertion method according to claim 104 and also comprising aggregating said at least one log of a process of insertion of said insertable element by employing said computer.

106. An automatically operative medical insertion method according to claim 105 and also comprising preparing said reference pathway based at least partially on said aggregate.

107. An automatically operative medical insertion method according to claim 106 and also comprising transmitting said reference pathway from said computer to said navigation subsystem.

108. An automatically operative medical insertion method comprising:

inserting an insertable element within a living organism in vivo;

physically associating a surface following element with said insertable element and causing said surface following element to follow a physical surface within said living organism in vivo;

automatically and selectably directing said insertable element along said physical surface; and controlling direction of said insertable element based at least partially on a perceived location of said surface following element along a reference pathway stored in a navigation subsystem, said insertable element comprising a disposable mouthpiece.

* * * * *